(12) United States Patent
Andersen et al.

(10) Patent No.: US 12,233,103 B2
(45) Date of Patent: *Feb. 25, 2025

(54) INDOLEAMINE 2,3-DIOXYGENASE BASED IMMUNOTHERAPY

(71) Applicant: IO BIOTECH APS, Copenhagen (DK)

(72) Inventors: Mads Hald Andersen, Naerum (DK); Per Thor Straten, Hvidovre (DK)

(73) Assignee: IO Biotech ApS, Copenhagen (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/298,263

(22) Filed: Apr. 10, 2023

(65) Prior Publication Data
US 2023/0233657 A1    Jul. 27, 2023

Related U.S. Application Data

(63) Continuation of application No. 17/721,577, filed on Apr. 15, 2022, now Pat. No. 11,648,302, which is a continuation of application No. 17/697,732, filed on Mar. 17, 2022, now abandoned, which is a continuation of application No. 16/261,114, filed on Jan. 29, 2019, now Pat. No. 11,324,813, which is a continuation of application No. 15/231,075, filed on Aug. 8, 2016, now Pat. No. 10,258,678, which is a continuation of application No. 12/988,124, filed as application No. PCT/DK2009/000095 on Apr. 17, 2009, now Pat. No. 9,433,666.

(30) Foreign Application Priority Data

Apr. 17, 2008   (DK) .................................. 2008 00565

(51) Int. Cl.
```
A61K 38/20   (2006.01)
A61K 38/19   (2006.01)
A61K 39/00   (2006.01)
A61K 45/06   (2006.01)
C12N 9/02    (2006.01)
```

(52) U.S. Cl.
CPC ........ *A61K 38/2013* (2013.01); *A61K 38/193* (2013.01); *A61K 39/001154* (2018.08); *A61K 45/06* (2013.01); *C12N 9/0069* (2013.01); *C12Y 113/11052* (2013.01); *A61K 2039/5158* (2013.01); *A61K 2039/55566* (2013.01); *A61K 2039/572* (2013.01)

(58) Field of Classification Search
None
See application file for complete search history.

(56) References Cited

U.S. PATENT DOCUMENTS

| | | | |
|---|---|---|---|
| 6,451,840 B1 | 9/2002 | Munn et al. |
| 6,482,416 B2 | 11/2002 | Munn et al. |
| 8,058,416 B2 | 11/2011 | Prendergast et al. |
| 8,507,434 B2 | 8/2013 | Popel et al. |
| 9,433,666 B2 | 9/2016 | Andersen et al. |
| 10,258,678 B2 | 4/2019 | Andersen et al. |
| 11,324,813 B2 | 5/2022 | Andersen et al. |
| 11,648,302 B2 | 5/2023 | Andersen et al. |
| 2003/0194803 A1 | 10/2003 | Mellor et al. |
| 2004/0234623 A1 | 11/2004 | Munn et al. |
| 2005/0186289 A1 | 8/2005 | Munn et al. |
| 2005/0250723 A1 | 11/2005 | Hoerr et al. |
| 2006/0292618 A1 | 12/2006 | Mellor et al. |
| 2007/0026503 A1 | 2/2007 | Lacey |
| 2007/0048769 A1 | 3/2007 | Mellor et al. |
| 2007/0173524 A1 | 7/2007 | Prendergast et al. |
| 2019/0201512 A1 | 7/2019 | Andersen et al. |

FOREIGN PATENT DOCUMENTS

| | | |
|---|---|---|
| EP | 2280721 B1 | 11/2017 |
| WO | WO-9747271 A2 | 12/1997 |
| WO | WO-0066764 A1 | 11/2000 |
| WO | WO-02059377 A2 | 8/2002 |
| WO | WO-02071928 A2 | 9/2002 |
| WO | WO-03012061 A2 | 2/2003 |
| WO | WO-03020884 A2 | 3/2003 |

(Continued)

OTHER PUBLICATIONS

Atkins, 2002, Seminars in Oncology, vol. 29: 12-17.*
Amar-Costesec et al.: "The Tumor Protein MAGE 1 is located in the cytosol of human melanoma cells." Biochem Biophys Res Commun. Vol. 204, No. 2. pp. 710-715. (Oct. 28, 1994).
Andersen, M. et al., "Identification of a Cytotoxic T Lymphocyte Response to the Apoptosis Inhibitor Protein Surviving in Cancer Patients," Cancer Res, vol. 61: 869-872 (2001).
Andersen MH et al., "Phosphorylated Peptides can be Transported by TAP Molecules, Presented by Class I MHC Molecules, and Recognized by Phosphopeptide-Specific Ctl," J Immunol, 163: 3812-3818, 1999.
Andersen MH, Pederson LO, Capeller B, Brocker Eb, Becker JC, Thor Straten P.: Spontaneous cytotoxic T-cell responses against survivin-derived MHC class-1-restricted T-cell epitopes in situ as well as ex vivo in cancer patients, Cancer Res: 61(16): 5964-5968, 2001.

(Continued)

*Primary Examiner* — Amy E Juedes
(74) *Attorney, Agent, or Firm* — COOLEY LLP

(57) ABSTRACT

The invention relates to the field of prophylaxis and therapy of cancer. Provided is a Indoleamine 2,3-dioxygenase (IDO) or peptide fragments hereof that are capable of eliciting anti-cancer immune responses. Specifically, the invention relates to the use of IDO or peptides derived herefrom or IDO specific T-cells for treatment of cancer. The invention thus relates to an anti-cancer vaccine which optionally may be used in combination with other immunotherapies and to IDO specific T-cells adoptively transferred or induced in vivo by vaccination as a treatment of cancer. The invention also provides that the medicaments herein provided may be used in combination with cancer chemotherapy treatment. The invention further provides the prophylaxis and therapy of infections by the same means as described above. The use of IDO and immunogenic peptide fragments hereof in cancer and infection treatment, diagnosis and prognosis is also provided.

19 Claims, 17 Drawing Sheets

Specification includes a Sequence Listing.

(56) References Cited

FOREIGN PATENT DOCUMENTS

| WO | WO-03087347 A1 | 10/2003 |
|---|---|---|
| WO | WO-2004048938 A2 | 6/2004 |
| WO | WO-2004053075 A2 | 6/2004 |
| WO | WO-2004054615 A1 | 7/2004 |
| WO | WO-2004056873 A1 | 7/2004 |
| WO | WO-2004093871 A1 | 11/2004 |
| WO | WO-2004094409 A1 | 11/2004 |
| WO | WO-2005017163 A2 | 2/2005 |
| WO | WO-2005036127 A2 | 4/2005 |
| WO | WO-2006056304 A2 | 6/2006 |
| WO | WO-2006081826 A2 | 8/2006 |
| WO | WO-2006122150 A1 | 11/2006 |
| WO | WO-2007034188 A2 | 3/2007 |
| WO | WO-2007095050 A2 | 8/2007 |
| WO | WO-2007115068 A2 | 10/2007 |

OTHER PUBLICATIONS

Andersen MH, Tan L, Sondergarrd I, et al: Poor correspondence between predicted and experimental binding of peptides to class I MHC molecules, Tissue Antigens 55: 519-531, 2000.

Asemissen AM, Keilholz U, Tenzer S, Muller M, Walters, Stevanovic Setal.: Identification of a highly immunogenic HLA-A*01-binding T cell epitope of WTI, Clin Cancer Res; 12(24):7476-7482, 2006.

Baban et al., "A Minor Population of Splenic Dendritic Cells Expressing CD19 Mediates IDO-Dependent T Cell Suppression Via Type I IFN Signaling Following B7 Ligation," Int. Immunol., 17:909-919 (2005).

Bauer TM, Jiga LP, Chuang JJ, et al.: Studying the immunosuppressive role of indoleamine 2,3-dioxygenase: tryptophan metabolites suppress rat allogeneic T-cell responses in vitro and in vivo, Transpl Int 18:95-1 00, 2005.

Beck KE, Blansfield JA, Tran KQ, et al.: Enterocolitis in patients with cancer after antibody blockade of cytotoxic T-lymphocyte-associated antigen 4, J Clin Oncol %20; 24: 2283-2289, 2006.

Bijker, et al., "CD8+ CTL Priming by Exact Peptide Epitopes in Incomplete Freund's Adjuvant Induces a Vanishing CTL Response, whereas Long Peptides Induce Sustained CTL Reactivity," J Immunol., vol. 179:5033-5040 (2007).

Boasso A, Herbeuval JP, Hardy AW, et al: HIV inhibits CD4+ T-cell proliferation by inducing indoleamine 2,3-dioxygenase in plasmacytoid dendritic cells, Blood 109:3351-3359, 2007.

Brandacher et al.: "Prognostic Value of Indoleamine 2,3-Dioxygenase Expression in Colorectal Cancer: Effect on Tumor-Infiltrating T Cells." Clin. Cancer Res. Vol. 12, No. 4. pp. 1144-1151 (Feb. 16, 2006).

Castelli C, Rivoltini L, Andreola G, Carrabba M, Renkvist N, Parmiani G: T-cell recognition of melanoma- associated antigens, J Cell Physiol; 182(3):323-331, 2000.

Certified Copy of Denmark Priority Application No. PA 200800565 filed Apr. 17, 2008 (102 pages).

Cho HI, Kim EK, Park SY, Lee SK, Hong YK, Kim TG: Enhanced induction of anti- tumor immunity in human and mouse by dendritic cells pulsed with recombinant TAT fused human survivn protein, Cancer Lett: 258(2): 189-198, 2007.

Choi BK, Kim YH, Kang WJ, et al: Mechanisms involved in synergistic anticancer immunity of anti-4-1 BB and anti-CD4 therapy, Cancer Res 67:8891-8899, 2007.

Clay TM, Morse M, Lyerly HK: Redirecting cytotoxic T lymphocyte responses with T-cell receptor transgenes, Expert Opin Bioi Ther; 2(4):353-360, 2002.

Dai et al., "Molecular Cloning, Sequencing and Expression of Human Interferon-γ-Inducible Indoleamine 2,3-Dioxygenase cDNA," Biochemical and Biophysical Research Communications, 168(1):1-8 (1990).

Elvin J, Cemndolo V, Elliott T, et al: A quantitative assay of peptide-dependent class I assembly, EurJ Immunol21:2025-2031, 1991.

English Translation of Japanese Office Action for JP Application No. 2011-504314 mailed Oct. 3, 2013 (5 pages).

English Translation of Japanese Office Action for JP Application No. 2015-05288 mailed Jan. 5, 2016 (6 pages).

Fujigaki Hidetsugu et al: "Nitration and inactivation of IDO by peroxynitdrite", J. Immunology, vol. 176, No. 1, 372-379, Jan. 1, 2006.

Herr W. Ranieri E, Gambotto A, et al: Identification of naturally processed and HLA-presented Epstein-Barr vims peptides recognized by CD4(+) or CDS(+) T lymphocytes from human blood, Proc Natl Acad Sci USA 96: 12033-12038, 1999.

Hu et al.: "Enhancement of Cytolytic T Lymphocyte Precursor Frequency in Melanoma Patients following Immunization with MAGE-I Peptide Loaded Antigen Presenting Cell-Based Vaccine." Cancer Research. Vol. 56. pp. 2479-2483. (Jun. 1, 1996).

Hwang SL, Chung NP, Chan JK et al: Indoleamine 2,3-dioxygenase (I DO) is essential for dendritic cell activation and chemotactic responsiveness to chemokines, Cell Res 15:167-175, 2005.

Hwu et al., "Indoleamine 2,3-Dioxygenase Production by Human Dendritic Cells Results in the Inhibition of T Cell Proliferation," J. Immunol. 2000; 164:3596-3599.

Keilholz, U. et al., "Immunologic monitoring of cancer vaccine therapy: results of a workshop sponsored by the Society for Biological Therapy," J Immunolher., vol. 25: 97-138 (2002).

Keilholz U, Letsch A, Busse A, Asemissen AM, Bauers, Blau IW et al.: A clinical and immunologic phase 2 trial of Wilms tumor gene product 1 (WT1) peptide vaccination in patients with AML and MDS, Blood; 113(26):6541-6548; 2009.

Krug LM, Dao T, Brown AB, Maslak P, Travis W, Bekele S, et al.: WTI peptide vaccinations induce CD4 and CDS T cell inunune responses in patients with mesothelioma and non-small cell lung cancer, Cancer Immunol Immunother. Oct. 2010;59(10):1467-79.

Lob S, Konigsrainer A, Schafer R, et al: Levo-but not dextro-1-methyltryptophan abrogates the IDO activity of human dendritic cells, Blood: 2007.

Lob Stefan et al.: Is IDO a key enzyme bridging the gap between tumor escape and tolerance induction; Langenbeck's Archivs of Surgery, vol. 393, No. 6, 4, 995-1003, Dec. 2007.

Maecker HT, Frey T, Nomura LE, et al: Selecting fluorochrome conjugates for maximum sensitivity, Cytometry A, 62: 169-173, 2004.

Makala, L., "The role of indoleamine 2, 3 dioxygenase in regulating host immunity to leishmania infection," Journal of Biomedical Science, (2012) 19:5, 8 pages.

Maker AV, Phan GQ, Attia P, et al: Tumor regression and autoimmunity in patients treated with cytotoxic T lymphocyte-associated antigen 4 blockade and interleukin 2: a phase 1/11 study, Ann Surg Oncol12: 1005-1016, 2005.

Mashishi T, Gray CM: The ELI SPOT assay: an easily transferable method for measuring cellular responses and identifying T cell epitopes, Clin Chem Lab Med; 40(9): 903-910, 2002.

McCutcheon M, Wehner N, Wensky A, et al: A sensitive Eli Spot assay to detect low-frequency human T lymphocytes, J Immunol Methods 210:149-166, 1997.

Morgan RA, Dudley ME, Wunderlich JR, Hughes MS, Yang JC, Sherry RM, Royal RE, Topalian SL, Kanunula US, Restifo NP, Zheng Z, Nahvi A, de Vries CR, Rogers-Freezer LJ, Mavroukakis SA, Rosenberg SA: Cancer regression in patients after transfer of genetically engineered lymphocytes, Science, 314(5796): 126-9, 2006, Epub Aug. 31, 2006.

Morris E, Hart D, Gao L et al: Generation of Tumor-specific T-cell therapies, Blood Reb 20:61-69, 2006.

Moss PA, Rosenberg WM, Bell JI: The human T cell receptor in health and disease, Annu Rev Immunol; 10:71-96, 1992.

Muller et al., "Indoleamine 2,3-dioxygenase in cancer: targeting pathological immune tolerance with small-molecule inhibitors," Expert Opinion Ther. Targets, 2005, 9(4):831-849.

Muller L, Provenzani C, Pawelec G, Generation of chronic myelogenous leukemia-specific T cells in cytokine-modified autologous mixed lymphocyte/tumor cell cultures, J Immunother; 24(6):482-492, 2001.

Munir et al.: "Natural CD4 T-Cell Responses against Indoleamine 2,3-Dioxygenase"; PLoS ONE, 7(4)(e34568), Apr. 2012, 12 pages.

(56) References Cited

OTHER PUBLICATIONS

Munn et al., "Expression of indoleamine 2,3-dioxygenase by plasmacytoid dendritic cells in tumor-draining lymph nodes," J. Clin Invest 2004; 114:280-290.
Nagaraj S, Pisarev V, Kinarsky L, Sherman S, Muro-Cacho C, Altieri DC et al: Dendritic cell-based full-length survivin vaccine in treatment of experimental tumors, J Immunother; 30(2): 169-179, 2007.
Nguyen XD, Eichler H, Sucker A et al: Collection of autologous monocytes for dendritic cell vaccination therapy in metastatic melanoma patients, Transfusion 42:428-432, 2002.
Nicolette CA, Healey D, Tcherapanova I, Whelton P, Monesmith T, Coombs L, Finke LH, Whiteside T, Miesowicz F: Dendritic cells for active immunotherapy: optimizing design and manufacture in order to develop commercially and clinically viable products, Vaccine, Sep. 27; 25 Suppi2:B47-60, Epub 2007.
Okamoto A, Nikaido T, Ochiai K et al: Indoleamine 2,3-dioxygenase serves as a marker of poor prognosis in gene expression profiles of serous ovarian cancer cells, Clin Cancer Res 11:6030-6039, 2005.
Otto K, Andersen MH, Eggert AO, Keikavoussi P, Pedersen LO, Rath JC et al.: Vaccine; 23(7):884-889, 2004.
Ou et al.: "Enchancement of dendritic cell-tumor fusion vaccine potency by indoleamine-pyrrole 2,3-dioxygenase inhibitor, 1-MT." J. Cancer Res. Clin. Oncol. Vol. 134. pp. 525-533 (2008).
Pawelec G, Marsh SG: ESTDAB: a collection of immunologically characterized melanoma cell lines and searchable databank, Cancer Immunol Immunother 55:623-627, 2006.
Platten M, HO PP, Youssef S et al: Treatment of autoimmune neuroinflammation with a synthetic tryptophan metabolite, Science 310:850-855; 2005.
Popov & Schultze; IDO-expressing regulatory dendritic cells in cancer and chronic infection, J Mol Med; 86(2): 145-60, Feb. 2008, Epub Sep. 18, 2007.
Rammensee HG, FalkK, Roetzschke 0: MHC molecules as peptide receptors, Curr Bioi 5:35-44, 1995.
Ravishankar et al. "Tolerance to apoptotic cells is regulated by indoleamine 2,3-dioxygenase." PNAS. Mar. 2012, 109(10): 3909-3914.
Redchenko & Rickinson, "Accessing Epstein-Barr Virus-Specific T-Cell Memory with Peptide-Loaded Dendritic Cells," J. Virol. 73, 334-342, 1999.
Rouas-Freiss et al: Expression of tolerogenic HLA-G molecules in cancer prevents antitumor responses; Seminars in Cancer Biology, Saunders Scientific Publications, vol. 17, No. 6, 413-421, Nov. 9, 2007.
Rubio V, Stuge TB, Singh N, Betts MR, Weber JS, Roederer Metal, Ex vivo Identification, isolation and analysis of tumor-cytolytic T cells, Nat Med; 9(11): 1377-1382, 2003.
Sanderson K, Scotland R, Lee P et al.: Autoimmunity in a phase I trial of a fully human anticytotoxic T-lymphocyte antigen-4 monoclonal antibody with multiple melanoma peptides and Montanide I SA 51 for patients with resected stages III and IV melanoma, J Clin On col. 23: 741-750, 2005.
Schaft N, Dorrie J, Muller I, Beck V, Baumann S, Schundert, Kampgen E, Schuler G, A new way to generate cytolytic tumor-specific T cells: electroporation of RNA coding for a T cell receptor into T lymphocytes, Cancer Immunol Immunother, 55(9): 1132-41 ,2006, Sep. Epub Dec. 13, 2005.

Scheibenbogen C, Suny, Keilholz U, et al: Identification of known and novel immunogenic T-cell epitopes from tumor antigens recognized by peripheral blood T cells from patients responding to IL-2-based treatment, Int J Cancer 20; 98:409-414, 2002.
Scheler M, Wenzel J, Luting T et al: Indoleamine 2,3-dioxygenase (I DO): the antagonist of type I interferon-driven skin inflammation; Am J Pathol171:1936-1943, 2007.
Schmidt Sm, Schang K, Muller MR, et al: Survivin is a shared tumor-associated antigen expressed in a broad variety of malignancies and recognized by specific cytotoxic T cells, Blood 102:571-576, 2003.
Scott et al., "The Immunoregulatory Enzyme IDO Paradoxically Drives B Cell-Mediated Autoimmunity," The Journal of Immunology, 2009, 182(12): 7509-7517.
Search Report for European Patent Application No. 17194619.7, mailed Feb. 12, 2018.
Sharma et al., "Plasmacytoid Dendritic Cells From Mouse Tumor-Draining Lymph Nodes Directly Activate Mature Tregs via Indoleamine 2,3-Dioxygenase," Journ. of Clinical Investigation, 117:2570-2582 (2007).
Sorensen et al.: "The Immune System Strikes Back: Cellular Immune Responses against Indoleamine 2,3-dioxygenase"; PLoS One, 4(9)(e6910), Sep. 2009.
Tamaki et al. "Immunotherapy of leukemia with WTI-peptide vaccine." Experimental Medicine. Vol. 20. No. 13. 2002. pp. 1947-1951—English translation provided.
Thebault P, Condamine T, Heslan M et al: Role of IFNy in allograft tolerance mediated by CD4+CD25+ regulatory T cells by induction of IDO in endothelial cells, Am J Transplant 7:2472-2482, 2007.
Tsai V, Southwood S, Sidney J, Sakaguchi K, Kawakami Y, Appella E et al: Identification of subdominant CTL epitopes of the GP100 melanoma-associated tumor antigen by primary in vitro immunization with peptide-pulsed dendritic cells, J Immunol; 158(4):1796-1802, 1997.
Uyttenhove, C et al., "Evidence for a tumoral immune resistance mechanism based on tryptophan degradation by indoleamine 2,3-dioxygenase," Nature Medicine, vol. 9, No. 10, (Oct. 2003), pp. 1269-1274.
Walter et al., "Reconstitution of cellular immunity against cytomegalovirus in recipients of allogeneic bone marrow by transfer of T-cell clones from the donor," N. Engl. J. Med., 333(16): 1038-44, Oct. 1995.
Wang, E, et al., "T-cell-directed cancer vaccines: the melanoma model", Expert Opinion on Biological Therapy 1(2), (2001), 277-290.
Weide et al., "Results of the First Phase 1/11 Clinical Vaccination Trial With Direct Injection of mRNA," Feb./Mar. 2008, J. Immunother. Vol. 31: 180-188.
Weinlich G, Murr C, Richardsen L, et al: Decreased serum tryptophan concentration predicts poor prognosis in malignant melanoma patients, Dermatology 214:8-14, 2007.
Wobser M, Keikavoussi P, Kunzmann V, Weininger M, Andersen MH, Becker JC: Complete remission of liver metastasis of pancreatic cancer under vaccination with a HLA-A2 restricted peptide derived from the universal tumor antigen survivn, Cancer Immumol Immunother; 55(10): 1294-1298, 2006.
Wobser M, Voigt H, Houben R et al: Dendritic cell based antitumor vaccination: impact of functional indoleamine 2,3-dioxygenase expression, Cancer Immunol Immunother 56: 1017-1024, 2007.
Zou W: Immunosuppressive networks in the tumour environment and their therapeutic relevance, Nat Rev Cancer 5:263-274, 2005.

\* cited by examiner

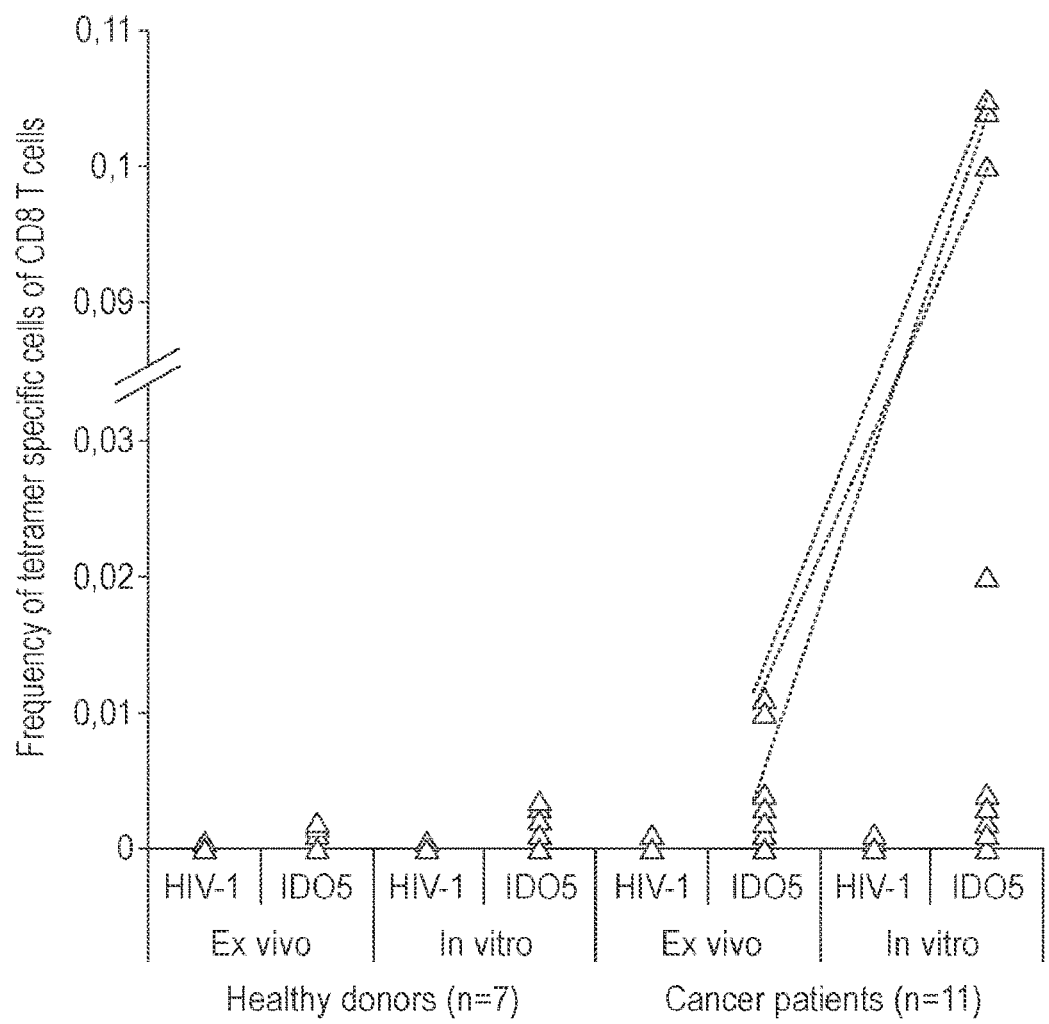

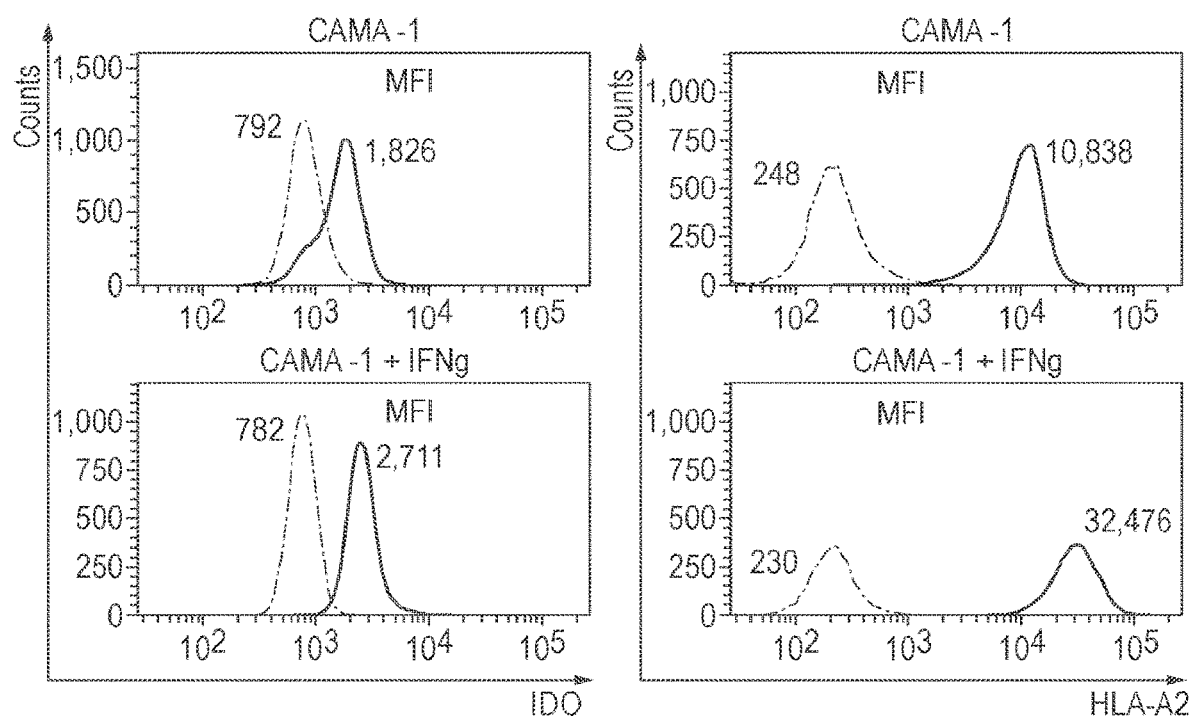

Fig. 8

```
IDOB   MAHAMENSWTISKEYHIDEEVGFALPNPQEMLPDFYNDWMFIAKHLPDLIESGQLRERVE
IDOC   MAHAMENSWTISKEYHIDEEVGFALPNPQEMLPDFYNDWMFIAKHLPDLIESGQLRERVE
IDO    ------------------------------------------------------------
IDOA   ------------------------------------------------------------

IDOB   KLNMLSIDHLTDHKSQRLARLVLGCITMAYVWGKGHGDVRKVLPRNIAVPYCQLSKKLEL
IDOC   KLNMLSIDHLTDHKSQRLARLVLGCITMAYVWGKGHGDVRKVLPRNIAVPYCQLSKKLEL
IDO    ------------------------------------------------------------
IDOA   ------------------------------------------------------------

IDOB   PPILVYADCVLANWKKKDPNKPLTYENMDVLFSFRDGDCSKGFFLVSLLVEIAAASAIKV
IDOC   ---------------------------MDVLFSFRDGDCSKGFFLVSLLVEIAAASAIKV
IDO    PPILVYADCVLANWKKKDPNKPLTYENMDVLFSFRDGDCSKGFFLVSLLVEIAAASAIKV
IDOA   ---------------------------MDVLFSFRDGDCSKGFFLVSLLVEIAAASAIKV
                                  ****************************

IDOB   IPTVFKAMQMQERDTLLKALLEIASCLEKALQVFHQIHGKYHVNPKAFFSVLRIYLSGWK
IDOC   IPTVFKAMQMQERDTLLKALLEIASCLEKALQVFHQIHGKYHVNPKAFFSVLRIYLSGWK
IDO    IPTVFKAMQMQERDTLLKALLEIASCLEKALQVFHQIH---DHVNPKAFFSVLRIYLSGWK
IDOA   IPTVFKAMQMQERDTLLKALLEIASCLEKALQVFHQIH---DHVNPKAFFSVLRIYLSGWK
       **************************************   *******************

IDOB   GNPQLSDGLVYEGFWEDPKEFAGGSAGQSSVFQCFDVLLGIQQTAGGGHAAQFLQDMRRY
IDOC   GNPQLSDGLVYEGFWEDPKEFAGGSAGQSSVFQCFDVLLGIQQTAGGGHAAQFLQDMRRY
IDO    GNPQLSDGLVYEGFWEDPKEFAGGSAGQSSVFQCFDVLLGIQQTAGGGHAAQFLQDMRRY
IDOA   GNPQLSDGLVYEGFWEDPKEFAGGSAGQSSVFQCFDVLLGIQQTAGGGHAAQFLQDMRRY
       ************************************************************

IDOB   MPPAHRNFLCSLESNPSVREFVLSKGDAGLREAYDACVKALVSLRSYHLQIVTKYILIPA
IDOC   MPPAHRNFLCSLESNPSVREFVLSKGDAGLREAYDACVKALVSLRSYHLQIVTKYILIPA
IDO    MPPAHRNFLCSLESNPSVREFVLSKGDAGLREAYDACVKALVSLRSYHLQIVTKYILIPA
IDOA   MPPAHRNFLCSLESNPSVREFVLSKGDAGLREAYDACVKALVSLRSYHLQIVTKYILIPA
       ************************************************************

IDOB   SQQPKENKTSEDPSKLEAKGTGGTDLMNFLKTVRSTTEKSLLKEG    SEQ ID NO: 14
IDOC   SQQPKENKTSEDPSKLEAKGTGGTDLMNFLKTVRSTTEKSLLKEG    SEQ ID NO: 15
IDO    SQQPKENKTSEDPSKLEAKGTGGTDLMNFLKTVRSTTEKSLLKEG    SEQ ID NO: 1
IDOA   SQQPKENKTSEDPSKLEAKGTGGTDLMNFLKTVRSTTEKSLLKEG    SEQ ID NO: 13
       *********************************************
```

Fig. 9

```
IDOLIKE   MEPHRPNVKTAVPLSIESEYHISEEYGFLLPDSLKELPDHYRPWMEIANKL
IDO       ------MAHAMENSWTISKEYHIDEEVGFALPNPQENLPDFYNDWMFIAKHL
                .:.***.** :;****.*. ::****. *. ** **;;:*

IDOLIKE   PQLIDAHQLQAHVDKMPLLSCQFLKGHREQRLAHLVLSFLTMGYVWQEGE
IDO       PDLIESGQLREVEKLNMLSIDHLTDHKSQRLARLVLGCITMAYVWGKGH
          *:**:: ::*.*:: :*: :***:: :* **::*:* ** ** .*:

IDOLIKE   AQPAEVLPRNLALPFVEVSRNLGLPPILVHSDLVLTNWTKKDPDG------
IDO       GDVRKVLPRNIAVPVCQLSKKLELPPILVYADCVLANWKKKDPNKPLTYE
          .: :******:*:*. :: ::****:** :::*:* **.** ::*****:

IDOLIKE   NLETIISFPGGESLHGFILVTALVEKEAVPGIKALVQATNALLQPNQEAL
IDO       NMDVLFSFRDGDCSKGFFLVSLLVEIAAASAIKVIPTVFKAMQMQERDTL
          *:: :::** *:*:**:**:.**: *.* * *.:: * *::*:*: ::*

IDOLIKE   LQALQRLRLSIQDITKTLGQMHDYVDPDIFYAGIRIFLSGWKDNPAMPAG
IDO       LKALLEIASCLEKALQVFHQIHDHVNPKAFFSVLRIYLSGWKGNPQLSDG
          *:** . : :  : :* :* :** *:* :* :** ****:*** :.*

IDOLIKE   LMYEGVSQEPLKYSGGSAAQSTVLHAFDEFLGIRHSK---ESGDFLYRMR
IDO       LVYEGFWEDPKEFAGGSAGQSSVFQCFDVLLGIQTAGGGHAAQFLQDMR
          *:***.:::* * :*** :*: ::*:* :*** ::::*

IDOLIKE   DYMPPSHKAFIEDIHSAPSLRDYILSSGQDHLLTAYNQCVQALAELRSYH
IDO       RYMPPAHRNFLCSLESNPSVREFVLSKGDAGLREAYDACVKALVSLRSYH
          ***.*::.*: .: *.** :::::*. *. * ** . **:**. *****

IDOLIKE   ITNVTKYLITAAAKAKHGKPNHLPGPPQALKDRCTGGTAVMSFLKSVRDK
IDO       LQIVTKYILIPAS----QQPKENKTSEDPSKLEAKGTGTDLMNFLKTVRST
          : :****:*:.*:      * .  :: :. *.  **:**::::***:** .
```

TLESILHPRG  SEQ ID NO: 16
TEKSLLKEG-  SEQ ID NO: 1
*  : :*:*:

INDOLEAMINE 2,3-DIOXYGENASE BASED IMMUNOTHERAPY

CROSS-REFERENCE TO RELATED APPLICATIONS

This application is a Continuation of Ser. No. 17/721,577, filed Apr. 15, 2022, now U.S. Pat. No. 11,648,302, issued May 16, 2023, which is a Continuation of U.S. patent application Ser. No. 17/697,732, filed Mar. 17, 2022 and now abandoned, which is a Continuation of U.S. patent application Ser. No. 16/261,114, filed Jan. 29, 2019, now U.S. Pat. No. 11,324,813, issued May 10, 2022, which is a Continuation of U.S. patent application Ser. No. 15/231,075, filed Aug. 8, 2016, now U.S. Pat. No. 10,258,678, issued Apr. 16, 2019, which is a Continuation of U.S. patent application Ser. No. 12/988,124, filed Jul. 8, 2011, now U.S. Pat. No. 9,433,666, issued Sep. 6, 2016, which is a National Stage Application of PCT/DK2009/000095, filed Apr. 17, 2009, which claims benefit of Application No. PA 2008 00565, filed Apr. 17, 2008 in Denmark and which applications are incorporated herein by reference. To the extent appropriate, a claim of priority is made to each of the above disclosed applications.

All patent and non-patent references cited in the application, or in the present application, are also hereby incorporated by reference in their entirety.

REFERENCE TO AN ELECTRONIC SEQUENCE LISTING

The contents of the electronic sequence listing (IOBT_002_06US_SeqList_ST26.xml; Size: 21,455 bytes; and Date of Creation: Apr. 10, 2023) are herein incorporated by reference in its entirety.

FIELD OF INVENTION

The present invention relates to the field of prophylaxis and therapy of cancer. In particular there is provided a protein Indoleamine 2,3-dioxygenase (IDO) or peptide fragments here of that are capable of eliciting anti-cancer immune responses. Specifically, the invention relates to the use of IDO or peptides derived here from or IDO specific T-cells for treatment of cancer. The invention thus relates to an anti-cancer vaccine which optionally may be used in combination with other immunotherapies and to IDO specific T-cells adoptively transferred or induced in vivo by vaccination as a treatment of cancer. It is an aspect of the invention that the medicaments herein provided may be used in combination with cancer chemotherapy treatment. A further aspect relates to the prophylaxis and therapy of infections by the same means as described above.

The use of IDO and immunogenic peptide fragments hereof in cancer and infection treatment, diagnosis and prognosis is also provided.

BACKGROUND OF INVENTION

The immune system has the capacity to recognize and destroy neoplastic cells; nevertheless, despite the fact that neoplastic transformation is associated with the expression of immunogenic antigens, the immune system often fails to respond effectively to these antigens. The immune system obviously becomes tolerant towards these antigens[1]. When this happens, the neoplastic cells proliferate uncontrollably leading to the formation of malignant cancers with poor prognosis for the affected individuals. The acquired state of tolerance must be overcome for cancer immunotherapy to succeed.

Indoleamine 2,3-dioxygenase (IDO) is a major component in maintaining the homeostasis of the immune system which, however, also contributes to tumor-induced tolerance. The expression and activation of IDO creates a tolerogenic milieu in the tumor and the tumor-draining lymph nodes (LN) either via direct suppression of T cells by degradation of the essential amino acid tryptophan or via enhancement of local Treg-(activated regulatory T cells) mediated immunosuppression. With respect to the former, some of the biological effects of IDO are mediated through local depletion of tryptophan, whereas others are mediated via immunomodulatory tryptophan metabolites[3,4]. Recently, an IDO-responsive signaling system in T cells has been identified, comprising the stress kinase GCN2 5. GCN2 responds to elevations in uncharged tRNA, as would occur if the T cell were deprived of tryptophan, and T cells lacking GCN2 are refractory to IDO-mediated suppression and anergy induction[6].

IDO can be expressed within the tumor by tumor cells as well as tumor stromal cells, where it inhibits the effector phase of immune responses. In addition, IDO-expressing antigen-presenting cells (APCs) are present in tumor-draining lymph nodes, where they are believed to create a tolerogenic microenvironment. Indeed, IDO-expressing CD19+ plasmacytoid dendritic cells (DCs) isolated from tumor-draining lymph node mediate profound immune suppression and T cell anergy in vivo[7,8]; plasmacytoid DC from normal lymph nodes and spleen do not express IDO. Very few cells constitutively express IDO in normal lymphoid tissue except in the gut. This implies that the DCs in tumor-draining lymph nodes, which constitutively express IDO, must receive a stimulus which is related to the presence of the tumor. This stimulus is believed to be delivered by activated regulatory T cells (Tregs) migrating from the tumor to the draining lymph node. Tregs have been shown to induce IDO via cell-surface expression of CTLA-4[9]. The induction of IDO converts the tumor-draining lymph nodes from an immunizing into a tolerizing milieu. Indeed, when IDO+ DCs are injected in vivo, they create suppression and anergy in antigen-specific T cells in the lymph nodes draining the injection site[10]. Beside its expression in immune competent cells, IDO is frequently expressed in the tumor microenvironment, either in the tumor cells itself or in different stromal cells. In this setting, IDO is believed to inhibit the effector phase of the immune response[11,12]. In clinic, it has repeatedly been observed, that expression of IDO in tumor cells is associated with an impaired prognosis[13,14].

Thus, the expression of IDO and the concomitant IDO induced cancer immunosuppression poses a problem in the treatment of cancer.

SUMMARY OF INVENTION

The problem of cancer immunosuppression is solved by the present invention which is based on the surprising finding by the inventors of spontaneous cytotoxic immune responses against IDO expressing cells in cancer patients. These findings open the way for novel therapeutic and diagnostic approaches which may be generally applicable in the control of cancer diseases.

The present invention targets the cancer disease by killing the IDO expressing cancer cells directly and by killing the IDO expressing, anergy inducing APCs/DCs. This is done by enabling the T cells to recognize the IDO expressing cells. Likewise, when the clinical condition is an infection, T cells are enabled to kill IDO expressing APCs/DCs.

Thus, the expression of the immune suppressing enzyme IDO in cancer cells and APCs is positive in conjunction with the application of the method of the present invention, which targets these IDO expressing cells. This approach, especially as it entails the killing of the APCs/DCs, goes against the common opinion in the field, where IDO generally is attempted down regulated/inhibited in order to remove the tolerizing milieu around the APCs/DCs while preserving these cells, which are considered required in order to launch an effective immune response.

Furthermore, the finding of spontaneous cytotoxic immune responses against IDO expressing cells is particularly surprising since IDO expressing cells antagonize the desired effects of other immunotherapeutic approaches. Therefore, a combination of IDO- and tumor-targeting immunotherapies is highly synergistic.

The present invention regards a vaccine composition comprising Indoleamine 2,3-dioxygenase (IDO) of SEQ ID NO: (1, 13, 14, 15 and/or 16) or a functional homologue thereof having at least 70% identity to SEQ ID NO: (1, 13, 14, 15 and/or 16) or an immunogenically active peptide fragment comprising a consecutive sequence of said IDO or said functional homologue thereof or a nucleic acid encoding said IDO or said peptide fragment; in combination with an adjuvant for use as a medicament.

The synergistic effect of a combination of immunotherapies based on the above disclosed vaccine is provided for in the aspect of the invention which regards a kit-of-parts comprising the vaccine composition and a further immunostimulating composition.

The aspect of combining the vaccine of the present invention with other cancer treatments such as chemotherapeutic agents is also provided for herein.

The aspect of combining the vaccine of the present invention with other treatments against infections such as immunotherapies and/or antibiotics is also provided for herein.

Another aspect of the invention regards a composition for ex vivo or in situ diagnosis of the presence in a cancer patient of T cells in PBL or in tumor tissue that is reactive with IDO, the composition comprising Indoleamine 2,3-dioxygenase (IDO) of SEQ ID NO (1, 13, 14, 15 and/or 16) or a functional homologue thereof having at least 70% identity to SEQ ID NO (1, 13, 14, 15 and/or 16) or an immunogenically active peptide fragment comprising a consecutive sequence of said IDO or said functional homologue thereof.

A further aspect regards a diagnostic kit for ex vivo or in situ diagnosis of the presence in a cancer patient of T cells in PBL or in tumor tissue that is reactive with IDO, the kit comprising Indoleamine 2,3-dioxygenase (IDO) of SEQ ID NO (1, 13, 14, 15 and/or 16) or a functional homologue thereof having at least 70% identity to SEQ ID NO (1, 13, 14, 15 and/or 16) or an immunogenically active peptide fragment comprising a consecutive sequence of said IDO or said functional homologue thereof.

Also a complex of a peptide fragment comprising a consecutive sequence of said IDO or said functional homologue thereof and a Class I HLA or a Class II HLA molecule or a fragment of such molecule is provided for herein.

A method of detecting in a cancer patient the presence of IDO reactive T-cells, the method comprising contacting a tumor tissue or a blood sample with a complex of a peptide fragment comprising a consecutive sequence of said IDO or said functional homologue thereof and a Class I HLA or a Class II HLA molecule or a fragment of such molecule and detecting binding of the complex to the tissue or the blood cells is a further aspect of the present invention.

Yet an aspect of the invention regards a molecule that is capable of binding specifically to a peptide fragment comprising a consecutive sequence of said IDO or said functional homologue thereof.

It follows that a method of treating a clinical condition such as a cancer or infection by any of the means described above falls within the scope of the present invention; the means including administering to an individual suffering from the clinical condition an effective amount of the vaccine composition as disclosed above; a molecule that is capable of binding specifically to a peptide fragment comprising a consecutive sequence of said IDO or said functional homologue thereof or a kit-of-parts comprising the aforementioned vaccine or molecule together with another immunostimulating composition and/or chemotherapeutic agent.

It is thus also an object of the present invention to use an immunogenically active peptide fragment comprising a consecutive sequence of said IDO or said functional homologue thereof or the vaccine composition of above in the manufacture of a medicament for the treatment or prevention of a cancer disease.

A further object of the present invention is a method of monitoring immunization, said method comprising the steps of: providing a blood sample from an individual; providing IDO of SEQ ID NO: (1, 13, 14, 15 and/or 16) or a functional homologue thereof having at least 70% identity to SEQ ID NO: (1, 13, 14, 15 and/or 16) or an immunogenically active peptide fragment comprising a consecutive sequence of said IDO or said functional homologue thereof or a nucleic acid encoding said IDO or said peptide fragment; determining whether said blood sample comprises antibodies or T-cells comprising T-cell receptors specifically binding the protein or peptide; and thereby determining whether an immune response to said protein or peptide has been raised in said individual.

BRIEF DESCRIPTION OF DRAWINGS

FIG. 1b shows HLA-A2-restricted T cell responses against IDO as measured by IFN-γ ELISPOT after T lymphocytes were stimulated once with peptide IDO6 (VLSKGDGL) (SEQ ID NO: 7), otherwise as described in FIG. 1a.

FIG. 1c shows HLA-A2-restricted T cell responses against IDO as measured by IFN-γ ELISPOT after T lymphocytes were stimulated once with peptide IDO5 (ALLEIASCL) (SEQ ID NO: 6), otherwise as described in FIG. 1a.

FIG. 2c shows tetramer analysis of IDO5-specific T cells ex vivo and in vitro in selected patients. In the three patients with strongest responses after in vitro stimulation, a respective reactivity was also detected ex vivo. Overall, PBL from 7 HLA-A2 positive healthy individuals and 11 HLA-A2 positive patients were analyzed which revealed an average frequency of 0.03% IDO reactive cells of total CD8+ T cells after in vitro stimulation in cancer patients, compared to 0.001% in healthy donors.

As a positive control, SW480 cells transfected with control ShRNA were used as target cells. Cancer cells transfected with IDO ShRNA were not recognized by the polyclonal IDO-specific bulk culture, whereas cells transfected with irrelevant control ShRNA were killed.

Figure 5A:
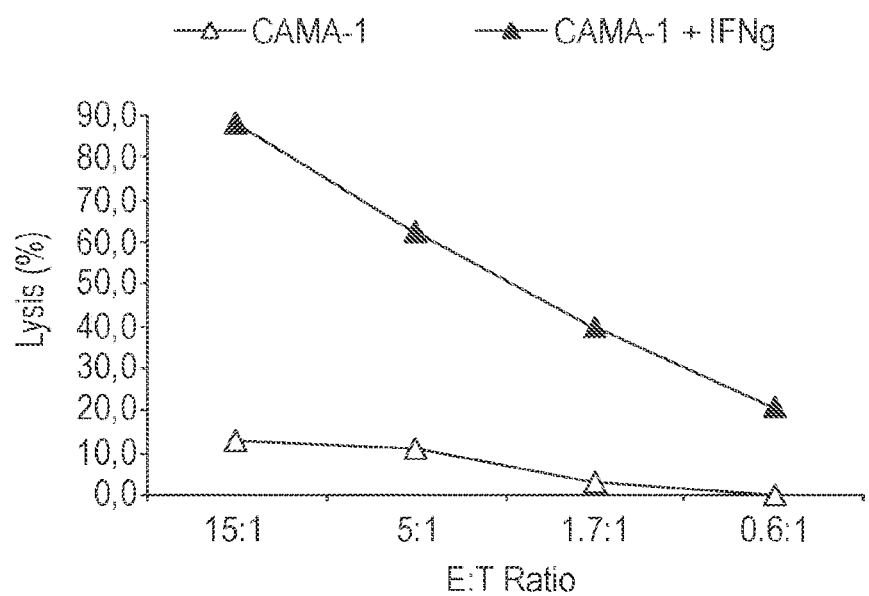
FIG. 5a shows functional capacity of an IDO5-specific T-cell clone (RBS35) to kill an IFN-γ treated breast cancer cell line[s] assayed by $^{51}$Cr-release assay. Lysis of the HLA-A2 positive breast cancer cell line CAMA-1 before and after IFN-γ treatment is shown. The CAMA-1 cell line was killed by RBS35. However, INF-γ treatment increased the expression of IDO in the cell line. Thus INF-γ treatment increased the killing by RBS35 of CAMA-1.
Figure 5B:
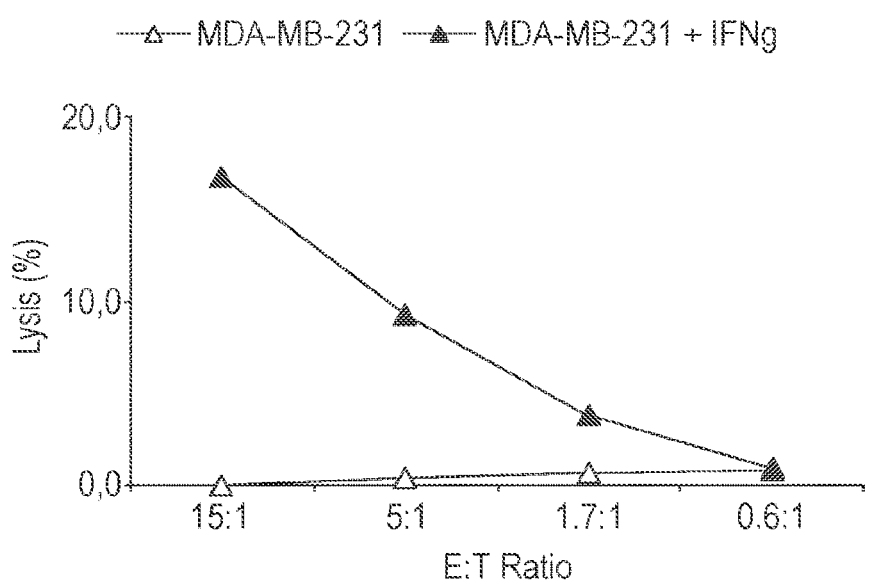
FIG. 5b shows functional capacity of an IDO5-specific T-cell clone (RBS35) to kill an IFN-γ treated breast cancer cell line assayed by $^{51}$Cr-release assay. Lysis of the HLA-A2 positive breast cancer cell line MDA-MB-231 before and after IFN-γ treatment is shown. MDA-MB-231 was not recognized by RBS35. However, INF-γ treatment increased the expression of IDO, and INF-γ treatment introduced killing of the MDA-MB-231 cells.
Figure 5D:
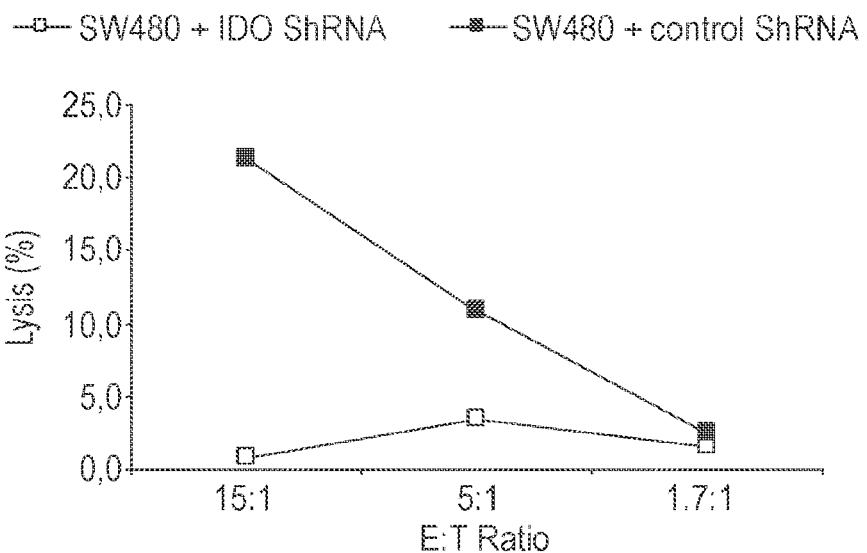
FIG. 5d shows lysis of the colon cancer cell line SW480 transfected with IDO ShRNA for down-regulation of IDO protein expression by an IDO5-specific T-cell bulk culture.
Figure 5E:
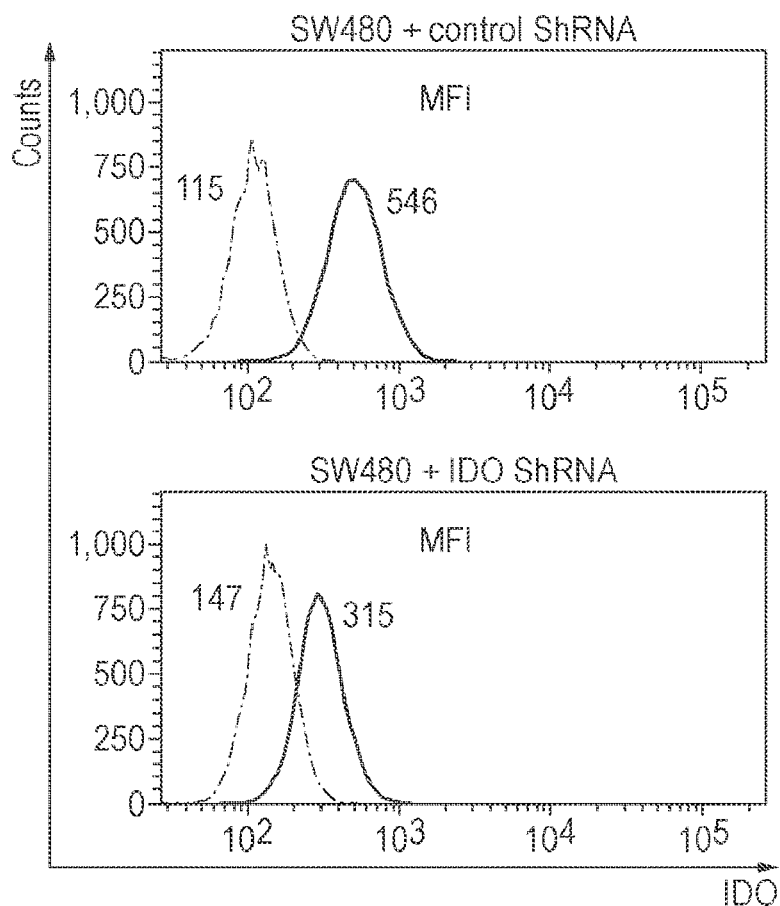
FIG. 5c shows histograms showing intracellular IDO expression and HLA-A2 expression in breast cancer cell line CAMA-1 before and after IFN-γ treatment.

FIG. 5e shows histograms showing intracellular IDO expression in SW480 transfected with control ShRNA (p=0.001 and MFIIDO/MFIIsotype control=4.8) (top) and IDO ShRNA (p=0.040 and MFIIDO/MFIIsotype control=2.1) (bottom).

Figure 6A:
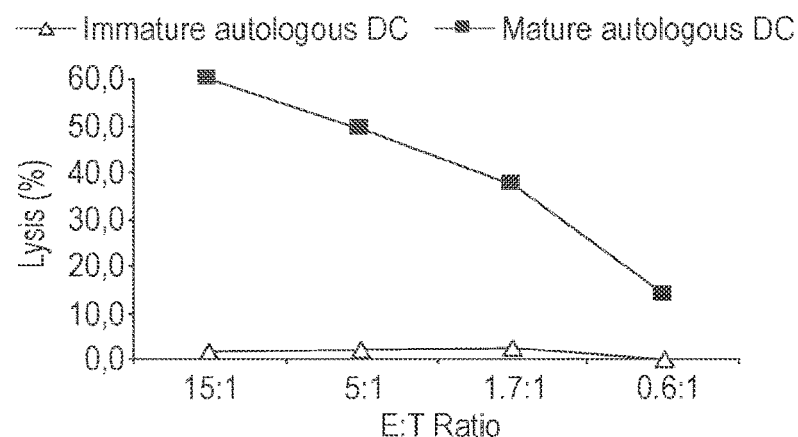

FIG. 6a shows functional capacity of an IDO5-specific T-cell clone (RBS35) to kill dendritic cells (DCs) assayed by $^{51}$Cr-release assay. RBS35 effectively killed the matured DC. In contrast, autologous immature IDO− DC were not killed by RBS35.

Figure 6B:
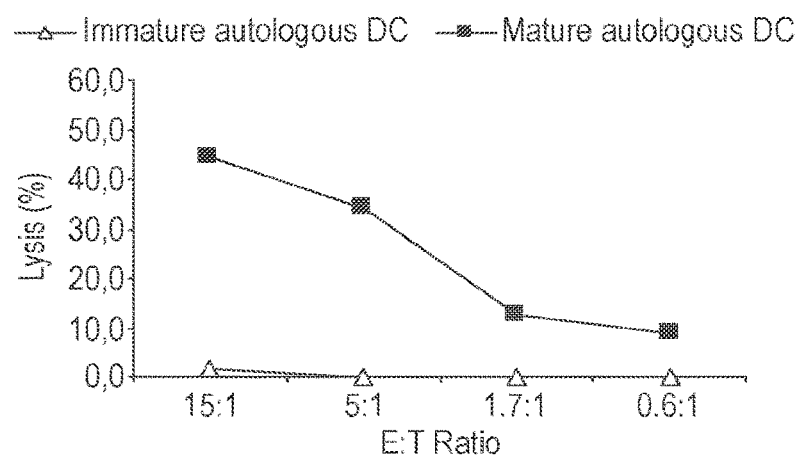

FIG. 6b shows functional capacity of an IDO5-specific T-cell clone (RBS35) to kill dendritic cells (DCs) assayed by $^{51}$Cr-release assay. Lysis of HLA-A2+ allogeneic immature and mature DC is shown. The allogenic matured DC were killed by RBS35 whereas the IDO− immature DC from the same donor were not affected.

Figure 6C:
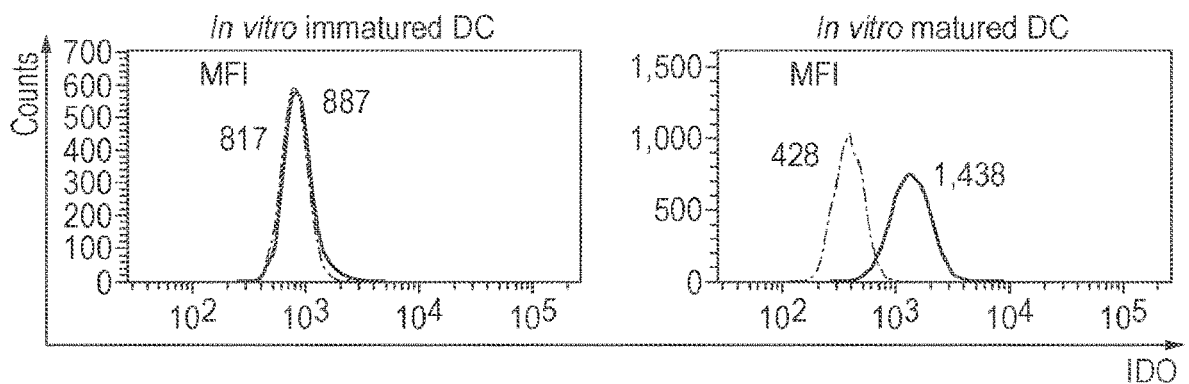

FIG. 6c shows histograms showing intracellular IDO expression in immature and in vitro matured DC. Mature DC exhibited expression of IDO in contrast to immature DC.

Figure 6D:
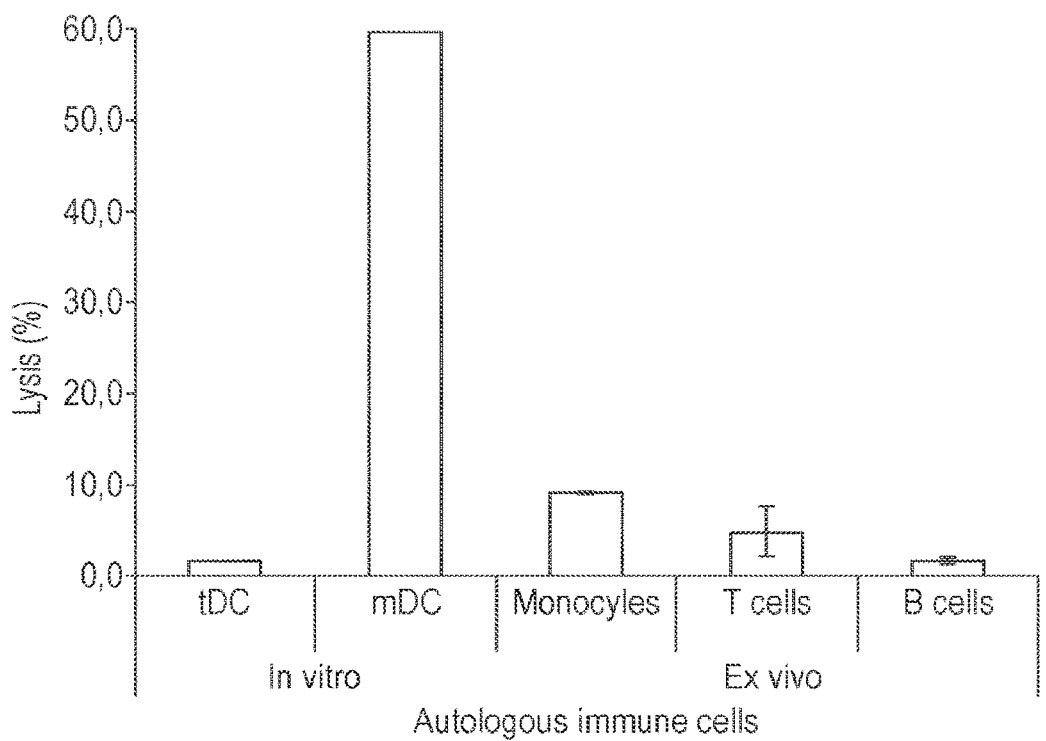

FIG. 6d shows the ability of RBS35 to lyse autologous monoctyes, T cells and B cells. For this purpose, we isolated CD14+ monoctyes, CD3+ T cells and CD19+ B cells directly ex vivo from IDO+ PBMC. The isolated cells were subsequently used as target cells in a 51Cr-release assay with RBS35. As a control, in vitro generated autologous IDO− immatured DC and IDO+ matured DC were employed. Autologous CD14+ monoctyes, CD3+ T cells and CD19+ B cells were not lysed by RBS35.

Figure 6E:
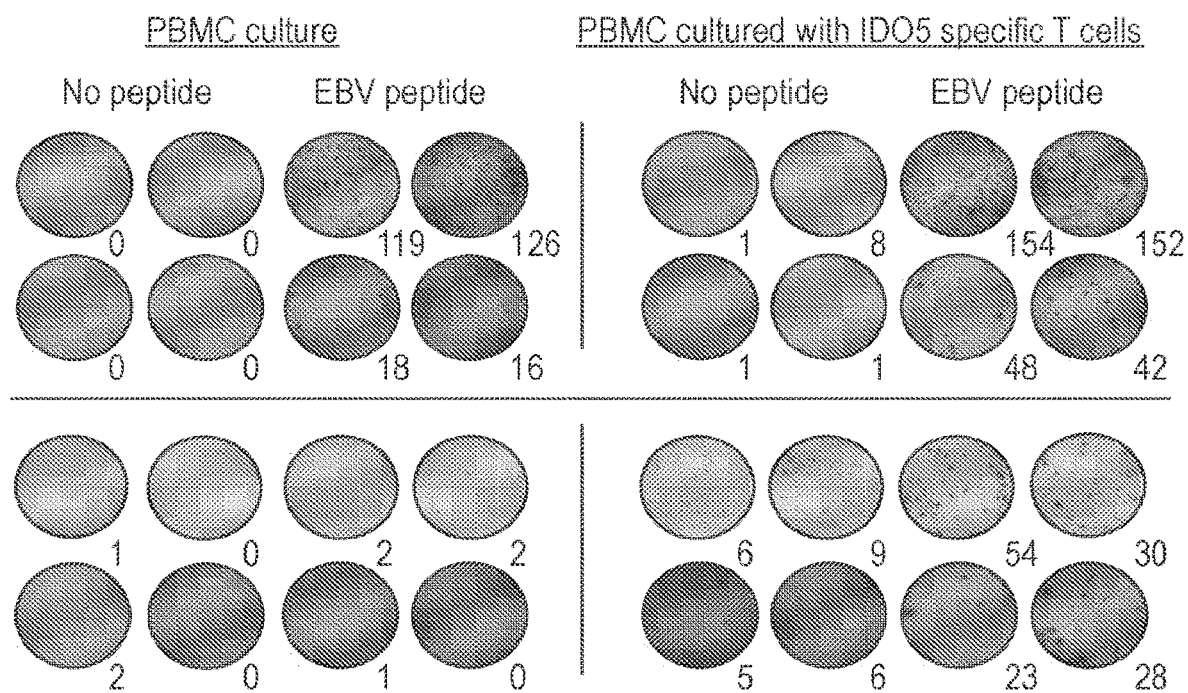

FIG. 6e shows HLA-A2 restricted T-cell responses against EBV BMLF1280-288 (GLCTLVAML) (SEQ ID NO: 19) as measured by ELISPOT in PBMC from a breast cancer patient. Cultures of PBMC were treated with IFN-γ to increase the immune activity as well as IDO expression in the cultures with and without autologous IDO specific T cells. Five days later we examined the immune reactivity against the HLA-A2 restricted immunodominant epitope from EBV BMLF1280-288 (GLCTLVAML) (SEQ ID NO: 19) in the cultures. Although the overall cell number was the same in the cultures the reactivity against the EBV peptide was higher in the cultures with IDO-specific T cells.

Figure 7A:
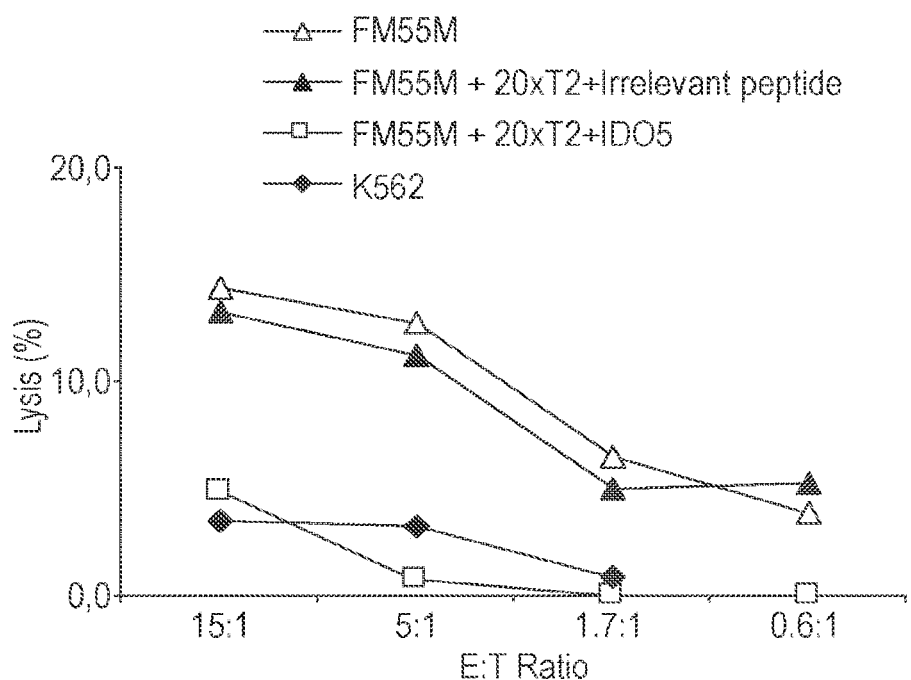

FIG. 7a shows specificity and functional capacity of IDO5-specific T cells assayed by 51Cr-release assays. Lysis by RBS35 of the HLA-A2+/IDO+ melanoma cell line FM55M without and with the addition of cold T2-cells pulsed with IDO5 peptide or an irrelevant peptide (HIV-1 pol476-484) (SEQ ID NO: 18) (inhibitor to target ratio=20:1), and NK cell activity of RBS35 examined using the natural killer cell line K562 as target cells is shown. The addition of cold T2-cells pulsed with an irrelevant peptide (HIV-1 pol476-484) (SEQ ID NO: 18) did not have an effect on the killing of FM55M. No cytotoxicity was observed against the NK-cell target cell line K562.

Figure 7B:
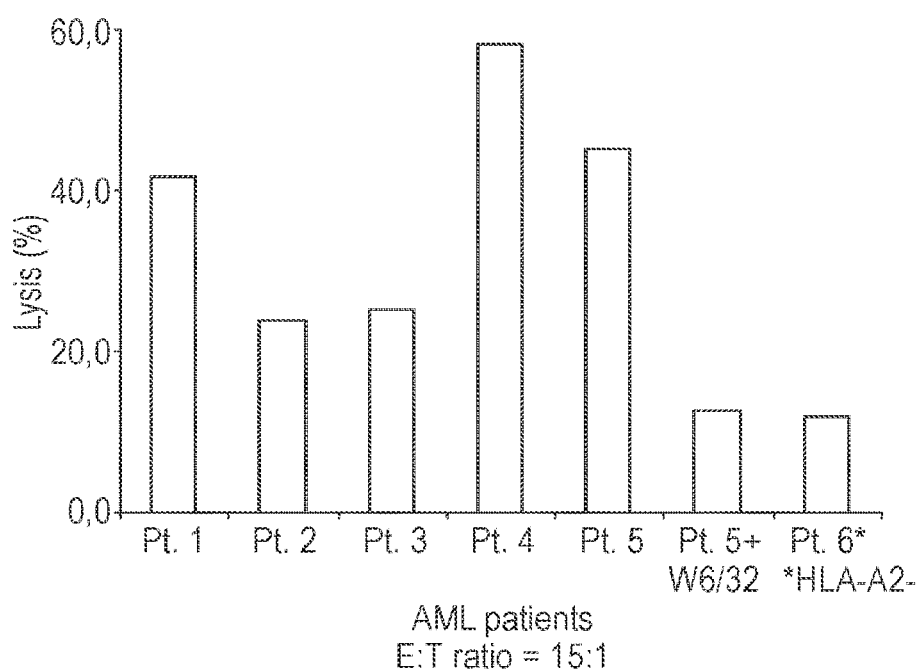
Figure 7C:
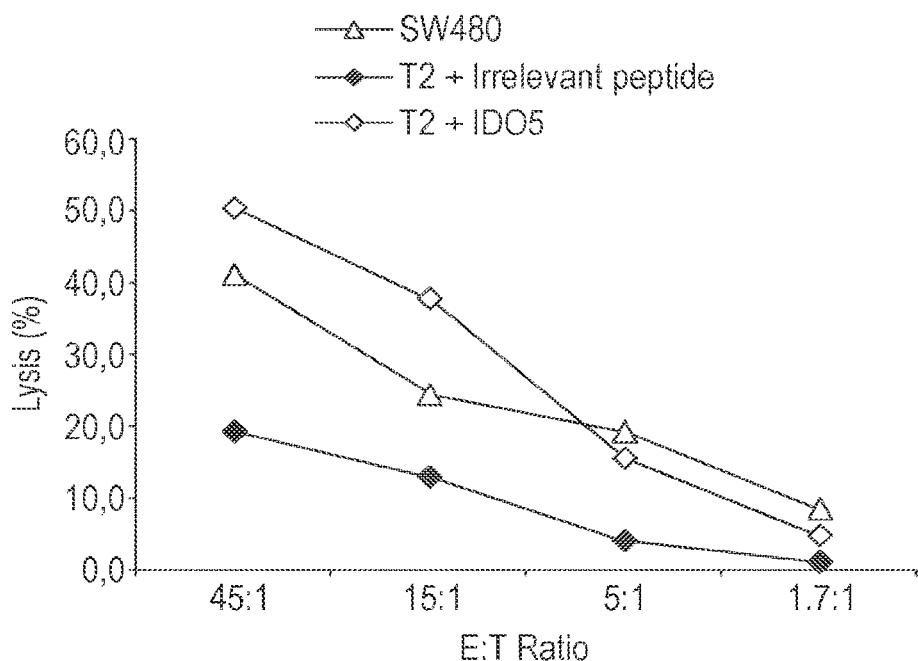

FIG. 7b shows lysis by RBS35 of AML-blasts enriched from six HLA-A2+ AML patients. AML-blasts, B cells, and T cells were depleted ex vivo from the bone marrow of the AML patients using CD19+ and CD3+ microbeads, respectively. The highly enriched AML-blasts were used as target cells with or without the addition of the HLA-class I specific antibody W6/32. RBS35 efficiently lysed the HLA-A2+ leukemia cells in an HLA-dependent manner, while HLA-A2− leukemia cells were not lysed FIG. 7c shows lysis of T2-cells pulsed with IDO5 peptide or an irrelevant peptide (HIV-1 pol476-484), and lysis of the HLAA2+/IDO+ colon cancer cell line SW480 by an IDO5-specific T-cell bulk culture. To illustrate the representative killing of tumor targets by RBS35, the killing of SW480 by a polyclonal, IDO5-specific bulk culture is shown.

Figure 7D:
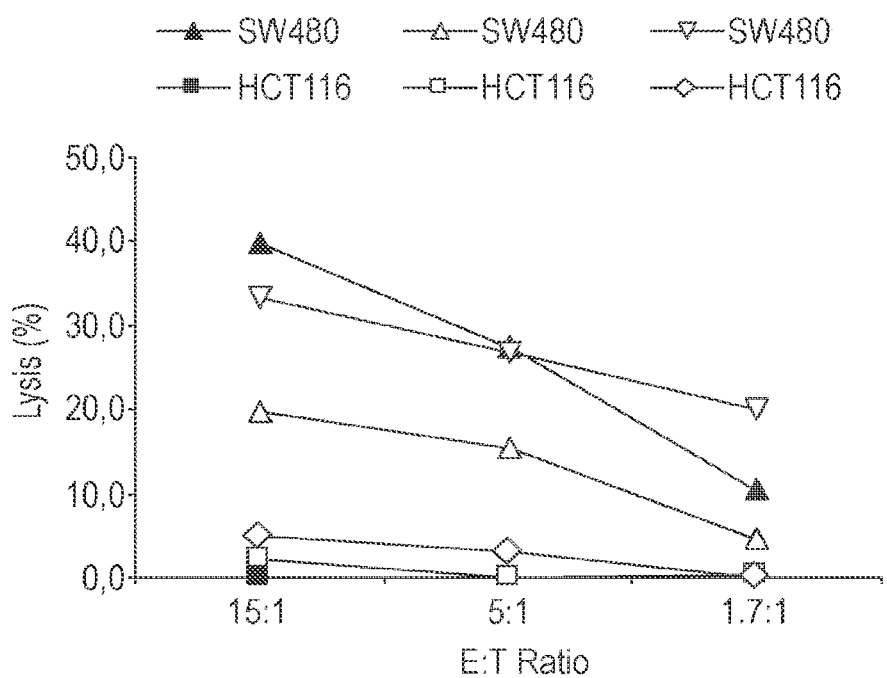

FIG. 7d shows lysis of the HLA-A2+/IDO+ colon cancer cell line SW480 and HLA-A2+/IDO− colon cancer cell line HCT-116 by three different IDO5-specific T-cell clones (RBS26 (white triangle), RBS31 (black triangle), RBS46 (grey triangle)) assayed by 51Cr-release assay. All assays were performed in different E:T ratios. Similar to RBS35, none of these clones (RBS26, RBS31, RBS46) lysed the HLA-A2+/IDO− colon cancer cell line HCT-116.

FIG. 8 shows alignment of IDO sequences IDO (SEQ ID NO: 1), IDOA (SEQ ID NO: 13), IDOB (SEQ ID NO: 14), and IDOC (SEQ ID NO: 15).

FIG. 9 shows pair wise alignment of IDO (SEQ ID NO: 1) and IDOLIKE (SEQ ID NO: 16).

DETAILED DESCRIPTION OF THE INVENTION

It is a major objective of the present invention to provide a vaccine composition comprising Indoleamine 2,3-dioxygenase (IDO) or an immunologically active polypeptide fragment hereof for use as a medicament in the prevention of, reduction of risk from, or treatment of cancer.

Definitions

Adjuvant: Any substance whose admixture with an administered immunogenic determinant/antigen/nucleic acid construct increases or otherwise modifies the immune response to said determinant.

Amino acid: Any synthetic or naturally occurring amino carboxylic acid, including any amino acid occurring in peptides and polypeptides including proteins and enzymes synthesized in vivo thus including modifications of the amino acids. The term amino acid is herein used synonymously with the term "amino acid residue" which is meant to encompass amino acids as stated which have been reacted with at least one other species, such as 2, for example 3, such as more than 3 other species. The generic term amino acid comprises both natural and non-natural amino acids any of which may be in the "D" or "L" isomeric form.

Antibody: Immunoglobulin molecules and active portions of immunoglobulin molecules. Antibodies are for example intact immunoglobulin molecules or fragments thereof retaining the immunologic activity.

Antigen: Any substance that can bind to a clonally distributed immune receptor (T-cell or B-cell receptor). Usually a peptide, polypeptide or a multimeric polypeptide. Antigens are preferably capable of eliciting an immune response.

APC: Antigen-presenting cell. An APC is a cell that displays foreign antigen complexed with MHC on its surface. T-cells may recognize this complex using their T-cell receptor (TCR). APCs fall into two categories: professional, (of which there are three types: Dendritic cells, macrophages and B-cells) or non-professional (does not constitutively express the Major histocompatibility complex proteins required for interaction with naive T cells; these are expressed only upon stimulation of the non-professional APC by certain cytokines such as IFN-γ).

Boost: To boost by a booster shot or dose is to give an additional dose of an immunizing agent, such as a vaccine, given at a time after the initial dose to sustain the immune response elicited by the previous dose of the same agent.

Cancer: Herein any preneoplastic or neoplastic disease, benign or malignant, where "neoplastic" refers to an abnormal proliferation of cells.

Carrier: Entity or compound to which antigens are coupled to aid in the induction of an immune response.

Chimeric protein: A genetically engineered protein that is encoded by a nucleotide sequence made by a splicing together of two or more complete or partial genes or a series of (non)random nucleic acids.

Clinical condition: A condition that requires medical attention, herein especially conditions associated with the expression of IDO. Examples of such conditions include: cancers and infections.

Complement: A complex series of blood proteins whose action "complements" the work of antibodies. Complement destroys bacteria, produces inflammation, and regulates immune reactions.

CTL: Cytotoxic T lymphocyte. A sub group of T-cells expressing CD8 along with the T-cell receptor and therefore able to respond to antigens presented by class I molecules.

Cytokine: Growth or differentiation modulator, used non-determinative herein, and should not limit the interpretation of the present invention and claims. In addition to the cytokines, adhesion or accessory molecules, or any combination thereof, may be employed alone or in combination with the cytokines.

Delivery vehicle: An entity whereby a nucleotide sequence or polypeptide or both can be transported from at least one media to another.

DC: Dendritic cell. (DCs) are immune cells and form part of the mammalian immune system. Their main function is to process antigen material and present it on the surface to other cells of the immune system, thus functioning as antigen-presenting cells (APCs).

Fragment: is used to indicate a non-full length part of a nucleic acid or polypeptide. Thus, a fragment is itself also a nucleic acid or polypeptide, respectively.

Functional homologue: A functional homologue may be any nucleic acid/protein/polypeptide that exhibits at least some sequence identity with a wild type version/sequence of a given gene/gene product/protein/polypeptide and has retained at least one aspect of the original sequences functionality. Herein a functional homologue of IDO has the capability to induce an immune response to cells expressing IDO.

IDO: Indoleamine 2,3-dioxygenase. Identified in SEQ ID NOs: (1, 13, 14, 15, and 16).

Individual: Generally any species or subspecies of bird, mammal, fish, amphibian, or reptile, preferably a mammal, most preferably a human being.

Infection: Herein the term "infection" relates to any kind of clinical condition giving rise to an immune response and therefore includes infections, chronic infections, autoimmune conditions and allergic inflammations.

Isolated: used in connection with nucleic acids, polypeptides, and antibodies disclosed herein 'isolated' refers to these having been identified and separated and/or recovered from a component of their natural, typically cellular, environment. Nucleic acids, polypeptides, and antibodies of the invention are preferably isolated, and vaccines and other compositions of the invention preferably comprise isolated nucleic acids, polypeptides or isolated antibodies.

MHC: Major histocompatibility complex, two main subclasses of MHC, Class I and Class II exist.

Nucleic acid: A chain or sequence of nucleotides that convey genetic information. In regards to the present invention the nucleic acid is a deoxyribonucleic acid (DNA).

Nucleic acid construct: A genetically engineered nucleic acid. Typically comprising several elements such as genes or fragments of same, promoters, enhancers, terminators, polyA tails, linkers, polylinkers, operative linkers, multiple cloning sites (MCS), markers, STOP codons, other regulatory elements, internal ribosomal entry sites (IRES) or others.

Operative linker: A sequence of nucleotides or amino acid residues that bind together two parts of a nucleic acid construct or (chimeric) polypeptide in a manner securing the biological processing of the nucleic acid or polypeptide.

Pathogen: a specific causative agent of disease, especially a biological agent such as a virus, bacteria, prion or parasite that can cause disease to its host, also referred to as an infectious agent.

PBL: Peripheral blood cells are the cellular components of blood, consisting of red blood cells, white blood cells, and platelets, which are found within the circulating pool of blood and not sequestered within the lymphatic system, spleen, liver, or bone marrow.

PBMC: A Peripheral Blood Mononuclear Cell (PBMC) is a blood cell having a round nucleus, such as a lymphocyte or a monocyte. These blood cells are a critical component in the immune system to fight infection and adapt to intruders. The lymphocyte population consists of T cells (CD4 and CD8 positive ~75%), B cells and NK cells (~25% combined).

Peptide: Plurality of covalently linked amino acid residues defining a sequence and linked by amide bonds. The term is used analogously with oligopeptide and poly-peptide. The natural and/or non-natural amino acids may be linked by peptide bonds or by non-peptide bonds. The term peptide also embraces post-translational modifications introduced by chemical or enzyme-catalyzed reactions, as are known in the art. The term can refer to a variant or fragment of a polypeptide.

Pharmaceutical carriers: also termed excipients, or stabilizers are non-toxic to the cell or individual being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™

Plurality: At least two.

Promoter: A binding site in a DNA chain at which RNA polymerase binds to initiate transcription of messenger RNA by one or more nearby structural genes.

Signal peptide: A short sequence of amino acids that determine the eventual location of a protein in the cell, also referred to as sorting peptide.

Surfactant: A surface active agent capable of reducing the surface tension of a liquid in which it is dissolved. A surfactant is a compound containing a polar group which is hydrophilic and a non polar group which is hydrophobic and often composed of a fatty chain.

Treg: Regulatory T Cells/T Lymphocytes

Vaccine: A substance or composition capable of inducing an immune response in an animal. Also referred to as an immunogenic composition in the present text. An immune response being an immune response (humoral/antibody and/or cellular) inducing memory in an organism, resulting in the infectious agent, being met by a secondary rather than a primary response, thus reducing its impact on the host organism. A vaccine of the present invention may be given as or prophylactic and/or therapeutic medicament. The composition may comprise one or more of the following: antigen (s), nucleic acid constructs comprising one or more antigens operatively linked to li, carriers, adjuvants and pharmaceutical carriers.

Variant: a 'variant' of a given reference nucleic acid or polypeptide refers to a nucleic acid or polypeptide that displays a certain degree of sequence homology/identity to said reference nucleic acid or polypeptide but is not identical to said reference nucleic acid or polypeptide.

Indoleamine 2,3-dioxygenase

Indoleamine 2,3-dioxygenase (IDO) is an enzyme catalyzes the conversion of L-tryptophan to N-formylkynurenine and is thus the first and rate limiting enzyme of tryptophan catabolism through the Kynurenine pathway. The catabolism of tryptophan causes a depletion of tryptophan which suppresses T-cell responses and promotes immune tolerance in mammalian pregnancy, tumor resistance, chronic infection, autoimmunity and allergic inflammation. Therefore, not only cancer, but infections in general and infections, especially chronic infections, autoimmunity and allergic inflammations in particular are all clinical conditions of relevance for the present invention.

IDO is present in humans in five forms: IDO, IDOA, IDOB, IDOC and IDOLIKE (also known in the literature as IDO2). IDO is a 403 amino acid residue long polypeptide as disclosed in SEQ ID NO:1, and is the preferred IDO in the present text together with IDOLIKE of SEQ ID NO: 16). The other IDOs are also of relevance to the present invention, although little is known about them; they are herein identified as IDOA: SEQ ID NO: 13, IDOB: SEQ ID NO: 14, and IDOC: SEQ ID NO 15. IDOLIKE is not as widely expressed as IDO but like its relative is also expressed in antigen-presenting dendritic cells where tryptophan catabolism drives immune tolerance. As IDO, IDOLIKE catabolizes tryptophan, triggers phosphorylation of the translation initiation factor eIF2alpha, and mobilizes translation of LIP, an inhibitory isoform of the immune regulatory transcription factor NF-IL6 (Popov & Schultze, 2008). Herein the term IDO generally refers to all of the abovementioned IDOs and their corresponding sequences.

IDO has been identified as a major immune regulatory molecule, which is part of several negative feedback mechanism by which immune responses are kept under control. In this manner, IDO also exert critical immunosuppressive function in cancer. In the study underlying the present invention, it was examined whether IDO itself may serve as target for immune responses, which may be exploited for immune therapy, particularly for treatment of cancer. By following a 'reverse immunology' approach, HLA-A2 peptides within the IDO protein were identified to which spontaneous T-cell reactivity were detected in patients suffering from unrelated tumor types, i.e. melanoma, renal cell carcinoma and breast cancer. These naturally occurring T-cells responses were readily visualized by flow cytometry using HLA/peptide tetramers after in vitro stimulation but also in direct ex vivo assays. Furthermore, it was unequivocally confirmed that IDO reactive T cells are indeed peptide specific, cytotoxic effector cells. In other words: IDO-specific T-cells effectively lyse IDO+ cancer cell lines of different origin, such us melanoma, colon carcinoma, breast cancer as well as directly ex vivo enriched AML blasts. The presence of spontaneous CTL-responses against IDO–derived peptide epitopes in PBL from patients suffering from unrelated cancer types as well as the killing of cancer cells of different origin by IDO-specific T-cells underline the immunotherapeutic potential of IDO. Even more distinctive is the finding that IDO– specific CTL recognize and kill IDO+ mature DC; hence, IDO-specific T-cells are able to kill immune competent DC. Recent reports have demonstrated that IDO is upregulated in human DCs upon maturation[23,24]. Moreover, IDO expression is also observed in DC intended for vaccination in cancer patients and the expression is maintained in situ after s.c. (subcutaneous) injection[25]. Expression of IDO in DC-based therapeutic vaccines holds critical clinical relevance via the attraction or induction of FoxP3(+) Tregs.

The dual roles for IDO—inhibition of both the initial and the effector phases of immune responses—are not mutually exclusive; in fact it is likely that both operate in a given tumor. There is an additional role by which IDO may be highly relevant to the outcome of immunotherapy of cancer: As an inflammation-induced counter-regulatory mechanism. Counter-regulatory responses are important in the immune system as they help to limit the intensity and extent of immune responses, which otherwise could cause dangerous damage to the host. However, with regard to anti-cancer immunotherapy counter-regulatory responses antagonize the ability to create an intense immune response against the tumor. Counter-regulation differs from tolerance in the sense that counter-regulation is a secondary event, elicited only in response to immune activation. IDO is known to be induced by both type I and II interferons, which are likely to be found at sites of immune activation and inflammation[28,27]. Notably, it is here in demonstrated that that the susceptibility of tumor cells to killing by IDO-reactive T-cells is increased by pre-incubation with IFN-γ. Likewise, systemic ligation of the co-stimulatory molecule 4-1BB (CD137) has been reported to induce IDO[28]. By definition most anti-cancer immunotherapeutic strategies irrespective of their molecular targets aim at the induction of an immunological activation and inflammation (for example, at the site of a vaccine or within the tumor). Virtually, within the limits of acceptable toxicity, as much immune activation as possible is the goal; hence, counter-regulation is not desired. In this regard, in both melanoma and renal cell carcinoma patients treatment with CTLA-4 blockade, i.e. anti-CTLA-4 antibodies, an association between enterocolitis and tumor regression has been reported[29]. Hence, autoimmune reactions clearly correlate with clinical efficacy[30,31]. CTLA-4 blockade is thought to mediate its antitumor and IRAE-inducing effects by reducing peripheral tolerance to self antigens and increased T-cell activation by inhibiting the function of Tregs.

Since IDO expressing antagonize the desired effects of other immunotherapeutic approaches, targeting IDO-expressing cells e.g. by vaccination, adoptive T-cell transfer or immune stimulatory agents, all of which are aspects of the present invention, consequently are highly synergistic in action with additional anti-cancer immunotherapy. In the present disclosure it is demonstrated that CTL defined IDO epitopes are broadly applicable in therapeutic vaccinations and are therefore of substantial immunotherapeutic value.

It is thus an aspect of the present invention to provide a vaccine composition comprising Indoleamine 2,3-dioxygenase (IDO) or an immunologically active polypeptide fragment hereof for use as a medicament for the treatment of a clinical condition. Said clinical condition may be cancer and it is a further aspect of the present invention to prevent, reduce the risk from, or treat cancer. Another aspect relates to the use of the vaccine composition of the present invention in combination with other medicaments such as immunotherapeutic medicaments and/or chemotherapeutic agents. Yet an aspect relates to the use of a vaccine composition as herein disclosed for the treatment of diseases of viral and/or microbial origin and further to the use of said vaccine in combination with other medicaments such as immunotherapeutic medicaments and/or antibiotics and/or anti-viral agents.

Functional Homologues
Sequences

The wild-type human IDO i.e. the naturally occurring non-mutated version of the protein is identified in SEQ ID NO: 1. The present invention covers vaccine compositions comprising IDO; immunologically active peptide fragments of IDO; peptide fragments of IDO, wherein at the most two amino acids have been substituted; and/or functional homologues of IDO comprising a sequence identity of at least 70% to SEQ ID NO: 1. The term polypeptide fragment is used herein to define any non-full length (as compared to SEQ ID NO: 1) string of amino acid residues that are directly derived from, synthesized to be identical with, or synthesized to have a sequence identity of at least 70% with IDO as identified in SEQ ID NO:1.

A functional homologue can be defined as a full length or fragment of IDO that differs in sequence from the wild-type IDO, such as wild-type human IDO, but is still capable of inducing an immune response against IDO expressing cells such as cancer cells and DCs. The IDO expressed in these cells may be wild type or endogenously mutated (such as a congenital mutant or a mutation induced during cell division or other). A functional homologue may be a mutated version or an alternative splice variant of the wild-type IDO. In another aspect, functional homologues of IDO are defined as described herein below. A functional homologue may be, but is not limited to, a recombinant version of full length or fragmented IDO with one or more mutations and/or one or more sequence deletions and/or additions introduced ex vivo.

A functional homologue of IDO may be any protein/polypeptide that exhibits at least some sequence identity with SEQ ID NO: 1 and has the capability to induce an immune response to cells expressing IDO.

Accordingly, in a specific embodiment the immunogenically active peptide fragment of the invention consists of 50 amino acid residues, for example at the most 45 amino acid residues, such as at the most 40 amino acid residues, for example at the most 35 amino acid residues, such as at the most 30 amino acid residues, for example at the most 25 amino acid residues, such as 18 to 25 consecutive amino acids of IDO as identified in SEQ ID NO: 1 or a functional homologue thereof; the functional homologue being one wherein at the most three amino acids have been substituted, such as two amino acids, such as one amino acid.

Accordingly in another specific embodiment the immunogenically active peptide fragment of the invention consists of the most 25 amino acid residues, such as at the most 24 amino acid residues, such as at the most 23 amino acid residues, such as at the most 22 amino acid residues, such as at the most 21 amino acid residues, such as at the most 20 amino acid residues, for example at the most 19 amino acid residues, such as at the most 18 amino acid residues, for example at the most 17 amino acid residues, such as at the most 16 amino acid residues, for example at the most 15 amino acid residues, such as at the most 14 amino acid residues, for example at the most 13 amino acid residues, such as at the most 12 amino acid residues, for example at the most 11 amino acid residues, such as 8 to 10 consecutive amino acids from IDO of SEQ ID no 1 or a functional homologue thereof; the functional homologue being one wherein at the most three amino acids have been substituted, such as two amino acids, such as one amino acid. Preferably, the peptide comprises at the most 10 consecutive amino acid residues from IDO, such as at the most 9 consecutive amino acid residues, such as 8 consecutive amino acid residues, such as 7 consecutive amino acid residues from IDO as identified in SEQ ID NO: 1 or a functional homologue thereof; the functional homologue being one wherein at the most three amino acids have been substituted, such as two amino acids, such as one amino acid.

Accordingly in some embodiments the peptides of the invention are nonapeptides (peptides comprising 9 amino acid residues), and some decapeptides (comprising 10 residues) and these may be selected from the non-limiting group of (peptide name first, then sequence, place in sequence of IDO and SEQ ID NO.): IDO1: Q L R E R V E K L (54-62) (SEQ ID NO: 2); IDO2: F L V S L L V E I (164-172) (SEQ ID NO: 3); IDO3: T L L K A L L E I (195-203) (SEQ ID NO: 4); IDO4: F I A K H L P D L (41-49) (SEQ ID NO: 5); IDO5: A L L E I A S C L (199-207)(SEQ ID NO:6); IDO6: V L S K G D A G L (320-328) (SEQ ID NO:7); IDO7: D L M N F L K T V (383-391) (SEQ ID NO: 8); IDO8: V L L G I Q Q T A (275-283) (SEQ ID NO: 9); IDO9: K V L P R N I A V (101-109) (SEQ ID NO: 10); IDO10: K L N M L S I D H L (61-70) (SEQ ID NO: 11); IDO11: S L R S Y H L Q I V (341-350) (SEQ ID NO: 12). Preferably, the peptide of the present invention is IDO5: A L L E I A S C L (199-207) (SEQ ID NO: 6); IDO2: F L V S L L V E I (164-172) (SEQ ID NO: 3); and/or IDO6: V L S K G D A G L (320-328) (SEQ ID NO: 7). Most preferably, vaccine composition of the present invention comprises at least one peptide of IDO5: A L L E I A S C L (199-207) (SEQ ID NO: 6).

Other peptides of the invention comprise (or more preferably consist of) between 4 and 120, preferably between 8 and 100, more preferably between 10 and 75, yet more preferably between 12 and 60, even more preferably between 15 and 40, such as between 18 and 25 contiguous amino acids of IDO of SEQ ID NO: 1 or a functional homologue thereof having at least 70% identity to SEQ ID NO: 1, wherein at the most three amino acids of IDO of SEQ ID NO: 1 have been substituted, deleted or added, such as two amino acids have been substituted, deleted or added, or one amino acid has been substituted, deleted or added.

In an embodiment of the invention IDO peptides comprise variant peptides. As used herein the expression "variant" refers to peptides which are homologous to the basic protein, which is suitably human IDO, but which differs from the base sequence from which they are derived in that one or more amino acids within the sequence are substituted for other amino acids. Suitably variants will have at the most six amino acid substitutions, for example at the most five amino acid substitutions, such as at the most four amino acid substitutions, for example at the most three amino acid substitutions, such as at the most two amino acid substitutions, for example at the most one amino acid substitution.

Suitably variants will share at least 70% sequence identity to IDO of SEQ ID NO: 1, and accordingly, variants preferably have at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with the sequence of human IDO.

Sequence identity can be calculated using a number of well-known algorithms and applying a number of different gap penalties. The sequence identity is calculated relative to full-length SEQ ID NO: 1. Any sequence alignment tool, such as but not limited to FASTA, BLAST, or LALIGN may be used for searching homologues and calculating sequence identity. Moreover, when appropriate any commonly known substitution matrix, such as but not limited to PAM, BLOSUM or PSSM matrices may be applied with the search algorithm. For example, a PSSM (position specific scoring matrix) may be applied via the PSI-BLAST program. Moreover, sequence alignments may be performed using a range of penalties for gap opening and extension. For example, the BLAST algorithm may be used with a gap opening penalty in the range 5-12, and a gap extension penalty in the range 1-2.

Functional equivalents may further comprise chemical modifications such as ubiquitination, labeling (e.g., with radionuclides, various enzymes, etc.), pegylation (derivatization with polyethylene glycol), or by insertion (or substitution by chemical synthesis) of amino acids (amino acids) such as ornithine, which do not normally occur in human proteins, however it is preferred that the functional equivalent does not contain chemical modifications.

Any changes made to the sequence of amino acid residues compared to that of IDO of SEQ ID NO: 1 are preferably conservative substitutions. A person skilled in the art will know how to make and assess 'conservative' amino acid substitutions, by which one amino acid is substituted for another with one or more shared chemical and/or physical characteristics. Conservative amino acid substitutions are less likely to affect the functionality of the protein. Amino acids may be grouped according to shared characteristics. A conservative amino acid substitution is a substitution of one amino acid within a predetermined group of amino acids for another amino acid within the same group, wherein the amino acids within a predetermined groups exhibit similar or substantially similar characteristics.

Thus, in an embodiment of the present invention, the vaccine composition comprises a polypeptide consisting of a consecutive sequence of IDO of SEQ ID NO: 1 in the range of 8 to 50 amino acids, preferably in the range of 8 to 10 or 20 to 25 amino acids, wherein at the most three amino acid has been substituted, and where the substitution preferably is conservative.

MHC

There are two types of MHC molecules; MHC class I molecules and MHC class II molecules. MHC class I molecules are recognized by CD8 T-cells, which are the principal effector cells of the adaptive immune response. MHC class II molecules are mainly expressed on the surface of antigen presenting cells (APCs), the most important of which appears to be the dendritic cells. APCs stimulate naïve T-cells, as well as other cells in the immune system. They stimulate both CD8 T-cells and CD4 T-cells.

In one embodiment, there are provided novel MHC Class I-restricted peptide fragments consisting of 8-10 amino acids from IDO of SEQ ID NO 1 or a functional homologue thereof, wherein at the most two amino acids of SEQ ID NO 1 have been substituted, which are characterized by having at least one of several features, one of which is the ability to bind to the Class I HLA molecule to which it is restricted at an affinity as measured by the amount of the peptide that is capable of half maximal recovery of the Class I HLA molecule ($C_{50}$ value) which is at the most 50 µM as determined by the assembly binding assay as described herein. This assembly assay is based on stabilization of the HLA molecule after loading of peptide to the peptide transporter deficient cell line T2. Subsequently, correctly folded stable HLA heavy chains are immunoprecipitated using conformation dependent antibodies and the peptide binding is quantitated. The peptides of this embodiment comprises (or more preferably consists of) at the most 200, preferably at the most 100, more preferably at the most 50, yet more preferably at the most 25, even more preferably at the most 20, yet even more preferably at the most 15, such as at the most 10, for example in the range of 8 to 10 contiguous amino acids of IDO of SEQ ID NO 1 or a functional homologue thereof wherein at the most two amino acids of SEQ ID NO 1 have been substituted.

This assay provides a simple means of screening candidate peptides for their ability to bind to a given HLA allele molecule at the above affinity. In preferred embodiments, the peptide fragment of the invention in one having a $C_{50}$ value, which is at the most 30 µM, such as a $C_{50}$ value, which is at the most 20 µM including $C_{50}$ values of at the most 10 µM, at the most 5 µM and at the most 2 µM.

In another preferred embodiment, there are provided novel MHC Class II-restricted peptide fragments of IDO of SEQ ID NO 1 or a functional homologue thereof, wherein at the most two amino acids of SEQ ID NO 1 have been substituted, (also referred to herein as "peptides"), which are characterized by having at least one of several features described herein below. The peptides of this embodiment comprises (or more preferably consists of) between 4 and 120, preferably between 8 and 100, more preferably between 10 and 75, yet more preferably between 12 and 60, even more preferably between 15 and 40, such as between 18 and 25 contiguous amino acids of IDO of SEQ ID NO 1 of SEQ ID NO 1 or a functional homologue thereof, wherein at the most two amino acids of SEQ ID NO 1 have been substituted, Thus there are provided novel MHC Class I-restricted peptide fragments of 8-10 amino acids or novel MHC Class II-restricted peptide fragments of 18-25 amino acids of IDO of SEQ ID NO 1 or a functional homologue thereof, wherein at the most two amino acids of SEQ ID NO 1 have been substituted, which are characterized by having at least one of several features described herein below, one of which is the ability to bind to the Class I or Class II HLA molecule to which it is restricted.

In particular embodiments there are provided peptide fragments, which is an MHC Class I-restricted peptide or an MHC class II-restricted peptide having at least one of the following characteristics:
  (i) capable of eliciting INF-γ-producing cells in a PBL population of a cancer patient at a frequency of at least 1 per $10^4$ PBLs as determined by an ELISPOT assay, and/or
  (ii) capable of in situ detection in a tumor tissue of CTLs that are reactive with the epitope peptide.

(iii) capable of inducing the growth of IDO specific T-cells in vitro.

More preferred peptides according to the present invention are peptides capable of raising a specific T-cell response as determined by an ELISPOT assay, for example the ELISPOT assay described in Example 1 herein below. Some peptides although they do not bind MHC class I or class II with high affinity, may still give rise to a T-cell response as determined by ELISPOT. Other peptides capable of binding MHC class I or class II with high affinity also give rise to a T-cell response as determined by ELISPOT. Both kinds of peptides are preferred peptides according to the invention.

Hence, preferred peptides according to the present invention are peptides capable of raising a specific T-cell response as measured by an ELISPOT assay, wherein more than 50 peptide specific spots per $10^8$ cells, more preferably per $10^7$, even more preferably per $10^6$, yet more preferably per $10^5$ cells, such as per $10^4$ cells are measured.

Most preferred peptides according to the present invention are peptides that are capable of eliciting a cellular immune response in an individual suffering from a clinical condition characterized by the expression of IDO, the clinical condition preferably being a cancer or infection, and most preferably a cancer.

As described above, the HLA system represents the human major histocompatibility (MHC) system. Generally, MHC systems control a range of characteristics: transplantation antigens, thymus dependent immune responses, certain complement factors and predisposition for certain diseases. More specifically, the MHC codes for three different types of molecules, i.e. Class I, II and III molecules, which determine the more general characteristics of the MHC. Of these molecules, the Class I molecules are so-called HLA-A, HLA-B and HLA-C molecules that are presented on the surface of most nucleated cells and thrombocytes.

The peptides of the present invention are characterized by their ability to bind to (being restricted by) a particular MHC Class I HLA molecule. Thus, in one embodiment the peptide is one which is restricted by a MHC Class I HLA-A molecule including HLA-A1, HLA-A2, HLA-A3, HLA-A9, HLA-A10, HLA-A11, HLA-Aw19, HLA-A23(9), HLA-A24(9), HLA-A25(10), HLA-A26(10), HLA-A28, HLA-A29(w19), HLA-A30(w19), HLA-A31(w19), HLA-A32 (w19), HLA-Aw33(w19), HLA-Aw34(10), HLA-Aw36, HLA-Aw43, HLA-Aw66(10), HLA-Aw68(28), HLA-A69 (28). More simple designations are also used throughout the literature, where only the primary numeric designation is used, e.g. HLA-A19 or HLA-A24 instead of HLA-Aw19 and HLA-A24(49), respectively. In specific embodiments, the peptide of the invention is restricted a MHC Class I HLA species selected from the group consisting of HLA-A1, HLA-A2, HLA-A3, HLA-A11 and HLA-A24. In specific embodiment, the peptide of the invention is restricted a MHC Class I HLA species HLA-A2 or HLA-A3.

In further useful embodiments, the peptide of the invention is a peptide, which is restricted by a MHC Class I HLA-B molecule including any of the following: HLA-B5, HLA-B7, HLA-B8, HLA-B12, HLA-B13, HLA-B14, HLA-B15, HLA-B16, HLA-B17, HLA-B18, HLA-B21, HLA-Bw22, HLA-B27, HLA-B35, HLA-B37, HLA-B38, HLA-B39, HLA-B40, HLA-Bw41, HLA-Bw42, HLA-B44, HLA-B45, HLA-Bw46 and HLA-Bw47. In specific embodiments of the invention, the MHC Class I HLA-B species to which the peptide of the invention is capable of binding is selected from HLA-B7, HLA-B35, HLA-B44, HLA-B8, HLA-B15, HLA-B27 and HLA-B51.

In further useful embodiments, the peptide of the invention is a peptide, which is restricted by a MHC Class I HLA-C molecule including but not limited to any of the following: HLA-Cw1, HLA-Cw2, HLA-Cw3, HLA-Cw4, HLA-Cw5, HLA-Cw6, HLA-Cw7 and HLA-Cw1.

In further useful embodiments, the peptide of the invention is a peptide, which is restricted by a MHC Class II HLA molecule including but not limited to any of the following: HLA-DPA-1, HLA-DPB-1, HLA-DQA1, HLA-DQB1, HLA-DRA, HLA-DRB and all alleles in these groups and HLA-DM, HLA-DO.

The selection of peptides potentially having the ability to bind to a particular HLA molecule can be made by the alignment of known sequences that bind to a given particular HLA molecule to thereby reveal the predominance of a few related amino acids at particular positions in the peptides. Such predominant amino acid residues are also referred to herein as "anchor residues" or "anchor residue motifs". By following such a relatively simple procedure based on known sequence data that can be found in accessible databases, peptides can be derived from IDO, which are likely to bind to a specific HLA molecule. Representative examples of such analyses for a range of HLA molecules are given in the below table:

TABLE 2

| HLA allele | Position 1 | Position 2 | Position 3 | Position 5 | Position 6 | Position 7 | C-terminal |
|---|---|---|---|---|---|---|---|
| HLA-A1 |  | T, S | D, E |  |  | L | Y |
| HLA-A2 |  | L, M |  |  | V |  | L, V |
| HLA-A3 |  | L, V, M | F, Y |  |  |  | K, Y, F |
| HLA-A11 |  | V, I, F, Y | M, L, F, Y, I |  |  |  | K, R |
| HLA-A23 |  | I, Y |  |  |  |  | W, I |
| HLA-A24 |  | Y |  |  | I, V | F | I, L, F |
| HLA-A25 |  | M, A, T | I |  |  |  | W |
| HLA-A26 | E, D | V, T, I, L, F |  |  |  | I, L, V | Y, F |
| HLA-A28 | E, D | V, A, L |  |  |  |  | A, R |
| HLA-A29 |  | E |  |  |  |  | Y, L |
| HLA-A30 |  | Y, L, F, V |  |  |  |  | Y |
| HLA-A31 |  |  | L, M, F, Y |  |  |  | R |
| HLA-A32 |  | I, L |  |  |  |  | W |
| HLA-A33 |  | Y, I, L, V |  |  |  |  | R |
| HLA-A34 |  | V, L |  |  |  |  | R |
| HLA-A66 | E, D | T, V |  |  |  |  | R, K |
| HLA-A68 | E, D | T, V |  |  |  |  | R, K |
| HLA-A69 |  | V, T, A |  |  |  |  | V, L |
| HLA-A74 |  | T |  |  |  |  | V, L |
| HLA-B5 |  | A, P | F, Y |  |  |  | I, L |

TABLE 2-continued

| HLA allele | Position 1 | Position 2 | Position 3 | Position 5 | Position 6 | Position 7 | C-terminal |
|---|---|---|---|---|---|---|---|
| HLA-B7 | * | P | | | | | L, F |
| HLA-B8 | | | K | K, R | | | L |
| HLA-B14 | | R, K | | | | | L, V |
| HLA-B15 (B62) | | Q, L, K, P, H, V, I, M, S, T | | | | | F, Y, W |
| HLA-B17 | | | | | | | L, V |
| HLA-B27 | | R | | | | | Y, K, F, L |
| HLA-B35 | | P | | | | | I, L, M, Y |
| HLA-B37 | | D, E | | | | | I, L, M |
| HLA-B38 | | H | D, E | | | | F, L |
| HLA-B39 | | R, H | | | | | L, F |
| HLA-B40 (B60, 61) | | E | F, I, V | | | | L, V, A, W, M, T, R |
| HLA-B42 | | L, P | | | | | Y, L |
| HLA-B44 | | E | | | | | F, Y, W |
| HLA-B46 | | M, I, L, V | | | | | Y, F |
| HLA-B48 | | Q, K | | | | | L |
| HLA-B51 | | A, P, G | | | | | F, Y, I, V |
| HLA-B52 | | Q | F, Y | | | | I, V |
| HLA-B53 | | P | | | | | W, F, L |
| HLA-B54 | | P | | | | | |
| HLA-B55 | | P | | | | | A, V |
| HLA-B56 | | P | | | | | A, V |
| HLA-B57 | | A, T, S | | | | | F, W, Y |
| HLA-B58 | | A, T, S | | | | | F, W, Y |
| HLA-B67 | | P | | | | | L |
| HLA-B73 | | R | | | | | P |
| HLA-Cw1 | | A, L | | | | | L |
| HLA-Cw2 | | A, L | | | | | F, Y |
| HLA-Cw3 | | A, L | | | | | L, M |
| HLA-Cw4 | | Y, P, F | | | | | L, M, F, Y |
| HLA-Cw6 | | | | | | | L, I, V, Y |
| HLA-Cw6 | | Y | | | | | L, Y, F |
| HLA-Cw8 | | Y | | | | | L, I, |
| HLA-Cw16 | | A, L | | | | | L, V |

* In one embodiment there is no specific anchor residue for this position, however in a preferred embodiment the anchor residue is R or A.

Thus, as an example, nonapeptides potentially having the ability to bind to HLA-A3 would have one of the following sequences: Xaa-L-Y-Xaa-Xaa-Xaa-Xaa-Xaa-K, Xaa-L-Y-Xaa-Xaa-Xaa-Xaa-Xaa-Y; Xaa-L-Y-Xaa-Xaa-Xaa-Xaa-Xaa-F or Xaa-V-Y-Xaa-Xaa-Xaa-Xaa-Xaa-K (Xaa indicating any amino acid residue). In a similar manner, sequences potentially having the ability to bind to any other HLA molecule can be designed. It will be appreciated that the person of ordinary skill in the art will be able to identify further "anchor residue motifs" for a given HLA molecule.

The peptide of the invention may have a sequence which is a native sequence of the IDO from which is derived. However, peptides having a higher affinity to any given HLA molecule may be derived from such a native sequence by modifying the sequence by substituting, deleting or adding at least one amino acid residue, e.g. on the basis of the procedure described above, whereby anchor residue motifs in respect of the given HLA molecule are identified.

Thus, in useful embodiments, the polypeptides of the invention include peptides, the sequences of which comprise, for each of the specific HLA alleles listed in the table, any of the amino acid residues as indicated in the table.

Thus, the peptides of the invention may be any of the above-mentioned peptides comprising contiguous sequences from IDO, wherein in the range of 1 to 10, preferably in the range of 1 to 5, more preferably in the range of 1 to 3, even more preferably in the range of 1 to 2, yet more preferably 1 amino acid has been exchanged for another amino acid, preferably in a manner so that the peptide comprises one or more, preferably all anchor residues of a given HLA-A specific peptide as indicated in the table above.

Examples preferable HLA species include, to which preferred peptides of the present invention are restricted include: a MHC Class I HLA species selected from the group consisting of HLA-A1, HLA-A2, HLA-A3, HLA-A11 and HLA-A24, more preferably the peptide is restricted by HLA-A3 or HLA-A2. Alternatively a preferred HLA species includes MHC Class I HLA-B species selected from the group consisting of HLA-B7, HLA-B35, HLA-B44, HLA-B8, HLA-B15, HLA-B27 and HLA-B51.

An approach to identifying polypeptides of the invention includes the following steps: selecting a particular HLA molecule, e.g. one occurring at a high rate in a given population, carrying out an alignment analysis as described above to identify "anchor residue motifs" in the IDO protein, isolating or constructing peptides of a suitable size that comprise one or more of the identified anchor residues and testing the resulting peptides for the capability of the peptides to elicit INF-γ-producing cells in a PBL population of a cancer patient at a frequency of at least 1 per $10^4$ PBLs as determined by an ELISPOT assay as described in Example 1.

In one aspect of the present invention, IDO-derived peptides longer than 8 to 10 amino acid residues are provided. Polypeptides longer than 8 to 10 amino acids are processed by the proteasome to a shorter length for binding to HLA molecules. Thus, when administering a polypeptide longer than 8 to 10 amino acid residues long, the "long"

polypeptide/protein/protein fragment/variant of IDO is processed into a series of smaller peptides in the cytosol by the proteasome. An advantage of using a longer polypeptide that may be processed by the proteasome into a variety of different shorter peptides is that more HLA classes may be targeted with one peptide than one 8 to 10 amino acid peptide that is restricted to a particular HLA class.

Surprisingly, some of the peptides of the present invention bind to MHC molecules with an affinity sufficiently high to render substitutions unnecessary (see FIG. 2) and are ready for use as antigens as they are presented here. Preferably, the vaccine composition of the present invention comprises one or more of the following: IDO protein (SEQ ID NO: 1), polypeptide fragments here from, likewise variants, functional homologues of full length and partial length IDO, contiguous peptides of IDO and functional homologues of these. More preferably, the vaccine composition comprises any of the sequences listed in the sequence list of the present disclosure. Very preferably, the vaccine composition comprises the peptides IDO5 (SEQ ID NO: 6), IDO 2 (SEQ ID NO: 3), and/or IDO6 (SEQ ID NO: 7).

A significant feature of the peptide of the invention is its capability to recognize or elicit INF-γ-producing responder T cells, i.e. cytotoxic T cells (CTLs) that specifically recognize the particular peptide in a PBL population, on an APC or tumor/neoplastic cells of an individual suffering from a cancer and/or an infection (target cells). This activity is readily determined by subjecting PBLs, APCs or tumor cells from an individual to an ELISPOT assay. Prior to the assay, it may be advantageous to stimulate the cells to be assayed by contacting the cells with the peptide to be tested. Preferably, the peptide is capable of eliciting or recognizing INF-γ-producing T cells at a frequency of at least 1 per $10^4$ PBLs as determined by an ELISPOT assay as used herein. More preferably the frequency is at least 5 per $10^4$ PBLs, most preferably at least 10 per $10^4$ PBLs, such as at least 50 or 100 per $10^4$ PBLs.

The ELISPOT assay represents a strong tool to monitor IDO peptide specific T-cell responses. A major implication of the findings herein is that the peptides of the invention are expressed and complexed with HLA molecules on cancer cells and/or IDO expressing APCs. This renders these cancer cells susceptible to destruction by CTLs and emphasizes the potential usefulness of IDO immunization to fight cancer and infections. The presence of spontaneous CTL-responses in PBLs from melanoma patients to HLA-restricted IDO derived peptide epitopes shows the immunotherapeutic potential of IDO immunogenic peptides.

In an embodiment of the present invention the peptide of the invention is capable of eliciting INF-γ-producing cells in a PBL population of an individual suffering from an clinical condition where IDO of SEQ ID NO: (1, 13, 14, 15, and/or 16) or a functional homologue thereof having at least 70% identity to SEQ ID NO 1 is expressed. The clinical condition is preferably a cancer or and infection and most preferably a cancer.

Origin

The peptides of the invention are, as mentioned above, derived from IDO of SEQ ID NO: 1, 13, 14, 15, and/or 16 or a fragment hereof, more preferably, the peptides are derived from IDO of SEQ ID NO: 1 and/or 16; and most preferably, the peptides are derived from IDO of SEQ ID NO: 1. The protein from which the peptide can be derived can be any IDO from any animal species in which the protein is expressed. In preferred embodiments, the starting protein is from a mammalian species including a rodent species, rabbit and a primate species such as humans. Based on the sequence of the selected protein, the peptide of the invention is derived by any appropriate chemical or enzymatic treatment of the protein starting material that results in a peptide of a suitable size as indicated above, or it can be synthesized by any conventional peptide synthesis procedures with which the person of ordinary skills in the art is familiar. Most preferably, the IDO protein, protein fragment, peptide, variant, and/or functional homologues of any of these are derived from IDO as the sequence of the protein is expressed in humans.

Individual

The individual to be treated with the vaccine composition of the present invention is an individual suffering from a clinical condition. The individual is preferably of a mammalian species and most preferably a human being. The individual may be of any age, young or old, and may be either male or female. The clinical condition from which the individual suffers may be a neoplastic disease such as a cancer, or an infection such as a microbial or viral infection e.g. HIV.

An embodiment of the present invention provides a vaccine for the treatment, reduction of risk of, stabilization of or prevention of a cancer. In another embodiment the present invention provides a vaccine for the treatment, reduction of risk of, stabilization of or prevention of a disease stemming from an infection, such as a microbial or viral infection.

A further embodiment regards a vaccine composition comprising IDO of SEQ ID NO: (1, 13, 14, 15 and/or 16) or a functional homologue thereof having at least 70% identity to SEQ ID NO: (1, 13, 14, 15 and/or 16) or an immunogenically active peptide fragment comprising a consecutive sequence of said IDO or said functional homologue thereof or a nucleic acid encoding said IDO or said peptide fragment; and an adjuvant for the treatment of a clinical condition characterized by the expression of IDO.

Cancer

The vaccine composition of the present invention may be used to prevent, reduce the risk from or treat a clinical condition. Preferably, the clinical condition is associated with or characterized by the expression of IDO. IDO may be IDO as identified in any of SEQ ID NOs: (1, 13, 14, 15, and/or 16) and may be a homolog sharing at least 70% identity with any of these in their wild type forms, but need not be functional. It is understood hereby that the expression level of IDO (the expression being expression of hnRNA, mRNA, precursor protein, fully processed protein and so on) is the same or higher than in an individual not suffering from a clinical condition. In a preferred embodiment of the invention, the clinical condition is cancer. Cancer (malignant neoplasm) is a class of diseases in which a group of cells display the traits of uncontrolled growth (growth and division beyond the normal limits), invasion (intrusion on and destruction of adjacent tissues), and sometimes metastasis (spread to other locations in the body via lymph or blood). These three malignant properties of cancers differentiate them from benign tumors, which are self-limited, do not invade or metastasize. Most cancers form a tumor but some, like leukemia, do not. The term "cancer" as used herein is meant to encompass any cancer, neoplastic and preneoplastic disease.

A non-limiting group of cancers given as examples of cancers that may be treated, managed and/or prevented by administration of the vaccine of the present invention include: colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangeosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hairy cell leukemia and thyroid cancer.

In a preferred embodiment the vaccine composition according to the invention vaccine composition is capable of eliciting a clinical response in subject, wherein the clinical response may be characterized by a stable disease, in a preferred embodiment the clinical response may be characterized by a partial response or preferably the clinical response may be characterized by complete remission of a cancer. Preferably, the cancer is selected from the group of; melanoma, breast cancer, ovarian cancer, lung cancer, pancreatic cancer, hematologic cancers (such as leukemias), colon and renal cell cancers.

In one aspect of the invention the vaccine composition is capable of eliciting a clinical response in an individual. In one embodiment the clinical response may be characterized by a stable disease (no further worsening or progression), in a preferred embodiment the clinical response may be characterized by a partial response or preferably the clinical response may be characterized by complete remission of a cancer or infections. The clinical response may be determined as described herein below.

In another aspect of the invention the vaccine composition is capable of eliciting a clinical response in subject, wherein the clinical response is characterized by a decrease in the sum of the longest diameter of the largest target lesion. The decrease may be determined as described herein below.

All measurable lesions up to a maximum of five lesions per organ and 10 lesions in total, representative of all involved organs should be identified as target lesions and recorded and measured at baseline.

Target lesions should be selected on the basis of their size (lesions with the longest diameter) and their suitability for accurate repeated measurements (either by imaging techniques or clinically).

A sum of the longest diameter (LD) for all target lesions will be calculated and reported as the baseline sum LD. The baseline sum LD will be used as reference by which to characterize the objective tumor.

All other lesions (or sites of disease) should be identified as non-target lesions and should also be recorded at baseline. Measurements of these lesions are not required, but the presence or absence of each should be noted throughout follow-up.

Evaluation of Target Lesions

Complete Response (CR): Disappearance of all target lesions

Partial Response (PR): At least a 30% decrease in the sum of the LD of target lesions, taking as reference the baseline sum LD Progressive Disease (PD): At least a 20% increase in the sum of the LD of target lesions, taking as reference the smallest sum LD recorded since the treatment started or the appearance of one or more new lesions Stable Disease (SD): Neither sufficient shrinkage to qualify for PR nor sufficient increase to qualify for PD, taking as reference the smallest sum LD since the treatment started Evaluation of Non-Target Lesions Complete Response (CR): Disappearance of all non-target lesions and normalization of tumor marker level Incomplete Response/Stable Disease (SD): Persistence of one or more non-target lesion(s) or/and maintenance of tumor marker level above the normal limits Progressive Disease (PD): Appearance of one or more new lesions and/or unequivocal progression of existing non-target lesions In an embodiment of the present invention the vaccine composition comprising any of the herein mentioned proteins and/or polypeptides is capable of eliciting a clinical response in subject, wherein the clinical response is characterized by a decrease in the sum of the longest diameter of the largest target lesion It is contemplated that the vaccine composition of the invention is capable of eliciting an immune response against a cancer expressing IDO of SEQ ID NO: 1 or a functional homologue thereof having at least 70% identity to SEQ ID NO: 1, when administered to an individual suffering from a cancer expressing IDO. The vaccine composition of the invention is capable of eliciting the production in a vaccinated individual of effector T-cells having a cytotoxic effect against the cancer cells, IDO expressing APCs and/or inducing infiltration of antigen specific T-cells in tumor stroma in a subject.

In addition to their capacity to elicit immune responses in PBL populations it is also contemplated that the peptides of the invention are capable of eliciting cytolytic immune responses in situ, i.e. in solid tumor tissues. This may for example be demonstrated by providing HLA-peptide complexes, e.g. being multimerized and being provided with a detectable label, and using such complexes for immunohistochemistry stainings to detect in a tumor tissue CTLs that are reactive with the epitope peptide of the invention. Accordingly, a further significant feature of the peptide of the invention is that it is capable of in situ detection in a tumor tissue of CTLs that are reactive with the epitope peptide.

It is also contemplated that the peptides of the invention, in addition to their capacity to bind to HLA molecules resulting in the presentation of complexes of HLA and peptides on cell surfaces, which complexes in turn act as epitopes or targets for cytolytic T cells, may elicit other types of immune responses, such as B-cell responses resulting in the production of antibodies against the complexes and/or a Delayed Type Hypersensitivity (DTH) reaction. The latter type of immune response is defined as a redness and palpable induration at the site of injection of the peptide of the invention.

It is an object of the presenting invention to provide a vaccine composition comprising Indoleamine 2,3-dioxygenase (IDO) of SEQ ID NO: (1, 13, 14, 15 and/or 16) or a functional homologue thereof having at least 70% identity to SEQ ID NO: (1, 13, 14, 15 and/or 16) or an immunogenically active peptide fragment comprising a consecutive sequence of said IDO or said functional homologue thereof or a nucleic acid encoding said IDO or said peptide fragment; and an adjuvant, for the prevention of, reduction of risk from or treatment of cancer.

Cancer Combination Treatment

In some cases it will be appropriate to combine the treatment method of the invention with a further conventional cancer treatment such as chemotherapy, radiotherapy, treatment with immunostimulating substances, gene therapy, treatment with antibodies and treatment using dendritic cells.

Since elevated expression of IDO in tumor cells leads to inhibition of the immune system, the combination of a IDO-based immunotherapy as disclosed by the present invention with cytotoxic chemotherapy and or another anticancer immunotherapeutic treatment is an effective approach to treat cancer. These remedies are also referred to herein as "second active ingredients".

Examples of chemotherapeutic agents that are of relevance in regards to co-administration (sequentially or simultaneously) with the vaccine composition of the present invention include, but are not limited to: all-trans retinoic acid, Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Oxaliplatin, Paclitaxel, Pemetrexed, Revlimid, Temozolomide, Teniposide, Thioguanine, Valrubicin, Vinblastine, Vincristine, Vindesine and Vinorelbine. In one embodiment, a chemotherapeutic agent for use in the combination of the present agent may, itself, be a combination of different chemotherapeutic agents. Suitable combinations include FOLFOX and IFL. FOLFOX is a combination which includes 5-fluorouracil (5-FU), leucovorin, and oxaliplatin. IFL treatment includes irinotecan, 5-FU, and leucovorin.

Another second active ingredient may be a kinase inhibitor, for separate, simultaneous or combined use in the treatment of tumors. Suitable kinase inhibitors include those which have been shown to possess anti-tumor activity (such as gefitinib (Iressa) and erlotinib (Tarceva) and these could be used in combination with the peptides. The receptor tyrosine kinase inhibitors, such as Sunitinib malate and Sorafenib which have been shown to be effective in the treatment of renal cell carcinoma are also suitable to be used as second active ingredients.

Further examples of second active ingredients are immunostimulating substances e.g. cytokines and antibodies. Such as cytokines may be selected from the group consisting of, but not limited to: GM-CSF, type I IFN, interleukin 21, interleukin 2, interleukin 12 and interleukin 15. The antibody is preferably an immunostimulating antibody such as anti-CD40 or anti-CTLA-4 antibodies. The immunostimulatory substance may also be a substance capable of depletion of immune inhibitory cells (e.g. regulatory T-cells) or factors, said substance may for example be E3 ubiquitin ligases. E3 ubiquitin ligases (the HECT, RING and U-box proteins) have emerged as key molecular regulators of immune cell function, and each may be involved in the regulation of immune responses during infection by targeting specific inhibitory molecules for proteolytic destruction. Several HECT and RING E3 proteins have now also been linked to the induction and maintenance of immune self-tolerance: c-Cbl, Cbl-b, GRAIL, Itch and Nedd4 each negatively regulate T cell growth factor production and proliferation.

In an embodiment, the vaccine composition of the present invention, comprising an IDO derived polypeptide, is administered in combination with a second active ingredient, such as an immunostimulatory substance. The immunostimulatory substance is preferably an interleukin such as IL-21 or IL-2 or a chemotherapeutic agent.

Infections

The word infection as used herein relates to any kind of clinical condition giving rise to an immune response, such as an inflammation, and therefore includes infectious diseases, chronic infections, autoimmune conditions and allergic inflammations. Thus, infections, such as infectious diseases, chronic infections, autoimmune conditions and allergic inflammations are all clinical conditions of relevance for the present invention, and are dealt with in turn hereunder. Furthermore, the terms infection and inflammation are used interchangeably herein.

Inflammation is the complex biological response of vascular tissues to harmful stimuli, such as pathogens, damaged cells, or irritants. It is a protective attempt by the organism to remove the injurious stimuli as well as initiate the healing process for the tissue. Inflammation can be classified as either acute or chronic. Acute inflammation is the initial response of the body to harmful stimuli and is achieved by the increased movement of plasma and leukocytes from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterized by simultaneous destruction and healing of the tissue from the inflammatory process. In either case, IDO is expressed by cells of the immune system such as the APCs and therefore infections and inflammations are clinical conditions that may be treated, prevented, or from which the risk may be reduced by the administration of the vaccine composition of the present invention. The vaccine composition preferably comprises IDO protein, protein fragments, polypeptide or peptides derived there from or functional homologues of any of these.

Examples of disorders associated with inflammation which are of relevance to the presenting invention include, but are not limited to: Allergic inflammations, Asthma, Autoimmune diseases, Chronic inflammations, Chronic prostatitis, Glomerulonephritis, Hypersensitivities, Infectious diseases, Inflammatory bowel diseases, Pelvic inflammatory disease, Reperfusion injury, Rheumatoid arthritis, Transplant rejection, and Vasculitis.

Chronic Infections and Inflammations

Chronic inflammation is especially of relevance in regards to the present invention. A chronic inflammation is a pathological condition characterized by concurrent active inflammation, tissue destruction, and attempts at repair. Chronically inflamed tissue is characterized by the infiltration of mononuclear immune cells (monocytes, macrophages, lymphocytes, and plasma cells), tissue destruction, and attempts at healing, which include angiogenesis and fibrosis.

In acute inflammation, removal of the stimulus halts the recruitment of monocytes (which become macrophages under appropriate activation) into the inflamed tissue, and existing macrophages exit the tissue via lymphatics. However in chronically inflamed tissue the stimulus is persistent, and therefore recruitment of monocytes is maintained, existing macrophages are tethered in place, and proliferation of macrophages is stimulated (especially in atheromatous plaques).

It is an object of the presenting invention to provide a vaccine composition comprising Indoleamine 2,3-dioxygenase (IDO) of SEQ ID NO: (1, 13, 14, 15 and/or 16) or a functional homologue thereof having at least 70% identity to SEQ ID NO: (1, 13, 14, 15 and/or 16) or an immunogenically active peptide fragment comprising a consecutive sequence of said IDO or said functional homologue thereof or a nucleic acid encoding said IDO or said peptide fragment; and an adjuvant, for the prevention of, reduction of risk from or treatment of chronic inflammations.

Infectious Diseases

The vaccine composition of the present invention may be used to prevent, reduce the risk from or treat a clinical condition. In a preferred embodiment of the invention, the clinical condition is an infectious disease. The infectious disease may be promoted by any infectious agent such as bacteria, virus, parasites and or fungi that are capable of inducing an increased expression of IDO in the individual suffering from the infectious disease, preferably, the infectious disease is or is at risk of becoming a chronic disease. As described in the background of invention, the increased expression of IDO has an immediate effect on the microbial agents in the vicinity of the IDO expressing organism by depriving it of tryptophan. However, this approach backfires, as the increased IDO expression induces inhibits the activity of Treg cells, if the IDO expressing cell is an APC. Therefore it is an aspect of the present invention to provide a vaccine composition comprising IDO protein, protein fragments, peptides and or variant of any of these for the treatment, amelioration of (lessening of severity) stabilization and/or prevention of a disease caused by an infectious agent.

An infectious diseases may be caused by a virus, and viral diseases against which the vaccine composition of the present invention may be administered in the treatment of include, but are not limited to the following viral diseases: HIV, AIDS, AIDS Related Complex, Chickenpox (Varicella), Common cold, Cytomegalovirus Infection, Colorado tick fever, Dengue fever, Ebola hemorrhagic fever, Hand, foot and mouth disease, Hepatitis, Herpes simplex, Herpes zoster, HPV (Human papillomavirus), Influenza (Flu), Lassa fever, Measles, Marburg hemorrhagic fever, Infectious mononucleosis, Mumps, Norovirus, Poliomyelitis, Progressive multifocal leukencephalopathy, Rabies, Rubella, SARS, Smallpox (Variola), Viral encephalitis, Viral gastroenteritis, Viral meningitis, Viral pneumonia, West Nile disease, and Yellow fever. Preferably, the vaccine composition is administered to individuals suffering from HIV/AIDS and viral infections that may cause cancer. The main viruses associated with human cancers are human papillomavirus, hepatitis B and hepatitis C virus, Epstein-Barr virus, and human T-lymphotropic virus; thus it is an object of the present invention to be administered as the treatment of or as part of the treatment of these viral infections.

Examples of bacterial infections of relevance for the present invention include, but are not limited to: Anthrax, Bacterial Meningitis, Botulism, Brucellosis, Campylobacteriosis, Cat Scratch Disease, Cholera, Diphtheria, Epidemic Typhus, Gonorrhea, Impetigo, Legionellosis, Leprosy (Hansen's Disease), Leptospirosis, Listeriosis, Lyme disease, Melioidosis, Rheumatic Fever, MRSA infection, Nocardiosis, Pertussis (Whooping Cough), Plague, Pneumococcal pneumonia, Psittacosis, Q fever, Rocky Mountain Spotted Fever (RMSF), *Salmonellosis*, Scarlet Fever, Shigellosis, Syphilis, Tetanus, Trachoma, Tuberculosis, Tularemia, Typhoid Fever, Typhus, and Urinary Tract Infections. It is an object of the present invention to provide a vaccine for the treatment and/or prevention and/or reduction of risk from a bacterial infection.

It is a further aspect of the present invention to provide a vaccine composition for the treatment and/or prevention and/or reduction of risk from: Parasitic infectious diseases such as, but not limited to: African trypanosomiasis, Amebiasis, Ascariasis, Babesiosis, Chagas Disease, Clonorchiasis, Cryptosporidiosis, Cysticercosis, Diphyllobothriasis, Dracunculiasis, Echinococcosis, Enterobiasis, Fascioliasis, Fasciolopsiasis, Filariasis, Free-living amebic infection, Giardiasis, Gnathostomiasis, Hymenolepiasis, Isosporiasis, Kala-azar, Leishmaniasis, Malaria, Metagonimiasis, Myiasis, Onchocerciasis, Pediculosis, Pinworm Infection, Scabies, Schistosomiasis, Taeniasis, Toxocariasis, Toxoplasmosis, Trichinellosis, Trichinosis, Trichuriasis, Trichomoniasis, and Trypanosomiasis; Fungal infectious diseases such as but not limited to: Aspergillosis, Blastomycosis, Candidiasis, Coccidioidomycosis, Cryptococcosis, Histoplasmosis, Tinea pedis; Prion infectious diseases such as but not limited to: transmissible spongiform encephalopathy, Bovine spongiform encephalopathy, Creutzfeldt-Jakob disease, Kuru-Fatal Familial Insomnia, and Alpers Syndrome; thus it is an object of the present invention to be administered as the treatment of or as part of the treatment of these parasitic, fungal or prion caused infections.

Infectious Disease Combination Treatment

It is further provided for that a treatment of any infectious disease by the administration of the vaccine composition according to the present invention may be given in conjunction with a further (second) active ingredient or in combination with a further treatment such as antibiotic treatment, chemotherapy, treatment with immunostimulating substances, treatment using dendritic cells, antiviral agents anti parasitic agents and so forth.

Examples of a second active ingredient that may be used in the treatment of an infectious disease in combination with the vaccine of the present invention include, and are not limited to antibiotics. The term antibiotics herein refers to substances with anti-bacterial, anti-fungal, anti-viral and/or anti-parasitical activity; examples of relevance to the present invention include, but are not limited to: Amikacin, Gentamycin, Kanamycin, Neomycin, Netilmicin, Paromomycin, Streptomycin, Tobramycin, Ertapenem, Imipenem, Meropenem, Chloramphenicol, Fluoroquinolones, Ciprofloxacin, Gatifloxacin, Gemifloxacin, Grepafloxacin, Levofloxacin, Lomefloxacin, Moxifloxacin, Norfloxacin, Ofloxacin, Sparfloxacin, Trovafloxacin, Glycopeptides, Vancomycin, Lincosamides, Clindamycin, Macrolides/Ketolides, Azithromycin, Clarithromycin, Dirithromycin, Erythromycin, Cefadroxil, Cefazolin, Cephalexin, Cephalothin, Cephapirin, Cephradine, Cefaclor, Cefamandole, Cefonicid, Cefotetan, Cefoxitin, Cefprozil, Cefuroxime, Loracarbef, Cefdinir, Cefditoren, Cefixime, Cefoperazone, Cefotaxime, Cefpodoxime, Ceftazidime, Ceftibuten, Ceftizoxime, Ceftriaxone, Cefepime, Monobactams, Aztreonam, Nitroimidazoles, Metronidazole, Oxazolidinones, Linezolid, Penicillins, Amoxicillin, Amoxicillin/Clavulanate, Ampicillin, Sulbactam, Bacampicillin, Carbenicillin, Cloxacillin, Dicloxacillin, Methicillin, Mezlocillin, Nafcillin, Oxacillin, Penicillin G, Penicillin V, Piperacillin, Piperacillin/Tazobactam, Ticarcillin, Ticarcillin/Clavulanate, Streptogramins, Quinupristin, Dalfopristin, Sulfonamide/Sulfamethoxazole, Trimethoprim, Tetracyclines, Demeclocycline, Doxycycline, Minocycline, Tetracycline, Azole antifungals Clotrimazole Fluconazole, Itraconazole, Ketoconazole, Miconazole, Voriconazole, Amphotericin B, Nystatin, Echinocandin, Caspofungin, Micafungin, Ciclopirox, Flucytosine, Griseofulvin, and Terbinafine. Of further relevance are antivirals such as Vidarabine, Acyclovir, Gancyclovir and Valcyte (valganciclovir), Nucleoside-analog reverse transcriptase inhibitors (NRTI): AZT (Zidovudine), ddI (Didanosine), ddC (Zalcitabine), d4T (Stavudine), 3TC (Lamivudine), Non-nucleoside reverse transcriptase inhibitors (NNRTI): Nevirapine, Delavirdine, Protease Inhibitors: Saquinavir, Ritonavir, Indinavir, Nelfinavir, Ribavirin, Amantadine/Rimantadine, Relenza and Tamiflu, Pleconaril, Interferons In an embodiment, the present invention regards a vaccine composition comprising IDO derived proteins, polypeptides and/or functional homologs of these for the treatment of an infectious disease in combination with at least one antibiotic. Preferably, the vaccine composition of the present invention is used for the treatment of chronic infections e.g. HIV and therefore is used in combination with any of the above listed antibiotics such as anti-viral agents.

Autoimmune Diseases

Autoimmune diseases arise when an organism fails to recognize its own constituent parts (down to the sub-molecular levels) as self, which results in an immune response against its own cells and tissues. Any disease that results from such an aberrant immune response is termed an autoimmune disease and is of relevance to the present invention. Examples hereof include but are not limited to: Coeliac disease, diabetes mellitus type 1 (IDDM), systemic lupus erythematosus (SLE), Sjögren's syndrome, multiple sclerosis (MS), Hashimoto's thyroiditis, Graves' disease, idiopathic thrombocytopenic purpura, and rheumatoid arthritis (RA).

It is an object of the present invention to provide a vaccine composition comprising Indoleamine 2,3-dioxygenase (IDO) of SEQ ID NO: (1, 13, 14, 15 and/or 16) or a functional homologue thereof having at least 70% identity to SEQ ID NO: (1, 13, 14, 15 and/or 16) or an immunogenically active peptide fragment comprising a consecutive sequence of said IDO or said functional homologue thereof or a nucleic acid encoding said IDO or said peptide fragment; and an adjuvant, for the prevention of, reduction of risk from or treatment of autoimmune diseases.

Autoimmune Disease Combination Treatment

Current treatments for autoimmune disease are usually immunosuppressive, anti-inflammatory, or palliative. Non-immune therapies, such as hormone replacement in Hashimoto's thyroiditis or diabetes mellitus Type 1 treatment outcomes of the autoaggressive response. Dietary manipulation limits the severity of celiac disease. Steroidal or NSAID treatment limits inflammatory symptoms of many diseases. Intravenous preparations of immune globulin (IVIG) are used for Chronic Inflammatory Demyelinating Polyneuropathy (CIDP) and Guillain-Barré syndrome (GBS). More specific immunomodulatory therapies, such as the TNFα antagonist Etanercept, have been shown to be useful in treating RA. These immunotherapies may be associated with increased risk of adverse effects, such as susceptibility to infection.

Helminthic therapy has developed based on these observations and involves inoculation of the individual with specific parasitic intestinal nematodes (helminths). There are currently two closely-related treatments available, inoculation with either *Necator americanus*, commonly known as hookworms, or *Trichuris Suis* Ova, commonly known as Pig Whipworm Eggs. Research is available that demonstrates this approach is highly effective in treating a variety of autoimmune disorders, including Crohn's, Ulcerative Colitis, Asthma, allergies, Multiple Sclerosis, and chronic inflammatory disorders In an embodiment, the vaccine herein disclosed is used in combination with a second active ingredient such as any of the above mentioned drugs and treatments against autoimmune diseases.

Allergic Inflammation

Allergy is a disorder of the immune system often also referred to as atopy. Allergic reactions occur to environmental substances known as allergens; these reactions are acquired, predictable and rapid. Strictly, allergy is one of four forms of hypersensitivity and is called type I (or immediate) hypersensitivity. It is characterized by excessive activation of certain white blood cells called mast cells and basophils by a type of antibody, known as IgE, resulting in an extreme inflammatory response. Common allergic reactions include eczema, hives, hay fever, asthma, food allergies, and reactions to the venom of stinging insects such as wasps and bees.

Allergic inflammation is an important pathophysiological feature of several disabilities or medical conditions including allergic asthma, atopic dermatitis, allergic rhinitis and several ocular allergic diseases.

It is an object of the present invention to provide a vaccine composition comprising Indoleamine 2,3-dioxygenase (IDO) of SEQ ID NO: (1, 13, 14, 15 and/or 16) or a functional homologue thereof having at least 70% identity to SEQ ID NO: (1, 13, 14, 15 and/or 16) or an immunogenically active peptide fragment comprising a consecutive sequence of said IDO or said functional homologue thereof or a nucleic acid encoding said IDO or said peptide fragment; and an adjuvant, for the prevention of, reduction of risk from or treatment of allergic inflammation.

Allergic Inflammation Combination Treatment

Two types of treatments are available for the treatment of allergic inflammations, pharmacotherapy and immunotherapy: pharmacotherapy and immunotherapy.

Pharmacotherapy, is the use of antagonistic drugs to block the action of allergic mediators, or to prevent activation of cells and degranulation processes. These include antihistamines, cortisone, dexamethasone, hydrocortisone, epinephrine (adrenaline), theophylline, cromolyn sodium and anti-leukotrienes, such as Montelukast (Singulair) or Zafirlukast (Accolate); anti-cholinergics, decongestants, mast cell stabilizers, and other compounds thought to impair eosinophil chemotaxis, are also commonly used.

Immunotherapy is the desensitization or hyposensitization treatment in which the individual is gradually vaccinated with progressively larger doses of the allergen in question. A second form of immunotherapy involves the intravenous injection of monoclonal anti-IgE antibodies. A third type, Sublingual immunotherapy, is an orally-administered therapy which takes advantage of oral immune tolerance to non-pathogenic antigens such as foods and resident bacteria.

In an embodiment, the vaccine herein disclosed is used in combination with a second active ingredient such as any of the above mentioned drugs and treatments against allergic inflammations.

Pharmaceutical Compositions

The present invention regards pharmaceutical compositions capable of treating, reducing the risk of and/or preventing a clinical disorder associated with IDO expression in an individual; in other words the terms vaccine and pharmaceutical composition are used interchangeably herein. The vaccine/pharmaceutical compositions of the present invention may be "traditional" vaccine compositions comprising antigens such as proteins polypeptides and/or nucleic acid molecules. They may also be in the form of compositions comprising cells, such as modified cells originating from the individual and later processed, or to compositions comprising complex molecules such as antibodies or TCRs.

Generally, a vaccine is a substance or composition capable of inducing an immune response in an individual. The composition may comprise one or more of the following: an "active component" such as an antigen(s) (e.g. protein, polypeptides, peptides, nucleic acids and the like), nucleic acid constructs comprising one or more antigens amongst other elements, cells, (e.g. loaded APC, T cells for adoptive transder aso.), complex molecules (Antibodies, TCRs and MHC complexes and more), carriers, adjuvants and pharmaceutical carriers. In the following, the various components of a vaccine composition according to the present invention are disclosed in more detail. The vaccine composition of the invention is capable of eliciting an immune response against a cancer, DC or APC expressing IDO of SEQ ID NO: 1 or a functional homologue thereof having at least 70% identity to SEQ ID NO 1, when administered to an individual suffering from a cancer and/or infection (leading to the expression of IDO). In a preferred embodiment the clinical condition is a cancer. The vaccine composition of the invention is capable of eliciting the production in a vaccinated individual of effector T-cells having a cytotoxic effect against cancer cells, APCs and DCs expressing IDO and/or inducing infiltration of antigen specific T-cells in tumor stroma in a subject.

Antigens and Other Active Components

Protein/Polypeptide Based Vaccine Compositions

The peptides of the present invention bind with surprisingly high affinity (see FIG. 2) and are ready for use as antigens as they are presented here. Preferably, the vaccine composition of the present invention comprises one or more of the following: IDO protein (SEQ ID NO: 1), polypeptide fragments here from, likewise variants, functional homologues of full length and partial length IDO, contiguous peptides of IDO and functional homologues of these. More preferably, the vaccine composition comprises any of the sequences listed in the sequence list of the present disclosure. Very preferably, the vaccine composition comprises the peptides IDO5 (SEQ ID NO: 6), IDO 2 (SEQ ID NO: 3), and/or IDO6 (SEQ ID NO: 7).

The choice of antigen in the vaccine composition of the invention will depend on parameters determinable by the person of skill in the art. As it has been mentioned, each of the different peptides of the invention is presented on the cell surfaces by a particular HLA molecule. As such, if a subject to be treated is typed with respect to HLA phenotype, a peptide/peptides are selected that is/are known to bind to that particular HLA molecule. Alternatively, the antigen of interest is selected based on the prevalence of the various HLA phenotypes in a given population. As an example, HLA-A2 is the most prevalent phenotype in the Caucasian population, and therefore, a composition containing a peptide binding to HLA-A2 will be active in a large proportion of that population. Furthermore, the antigens/peptides of the present invention may be modified according to the anchor residue motifs presented in Table 2, to enhance binding to particular HLA molecules.

The composition of the invention may also contain a combination of two or more IDO derived peptides, each interacting specifically with a different HLA molecule so as to cover a larger proportion of the target population. Thus, as examples, the pharmaceutical composition may contain a combination of a peptide restricted by a HLA-A molecule and a peptide restricted by a HLA-B molecule, e.g. including those HLA-A and HLA-B molecules that correspond to the prevalence of HLA phenotypes in the target population, such as e.g. HLA-A2 and HLA-B35. Additionally, the composition may comprise a peptide restricted by an HLA-C molecule.

In the case of peptide-based vaccines, epitopes can be administered in an 'MHC-ready' form, which enables presentation through exogenous loading independently of antigen uptake and processing by host antigen-presenting cells. The peptides of the present invention comprise both peptides in a short 'MHC-ready' form and in a longer form requiring processing by the proteasome thus providing a more complex vaccine composition that can target multiple tumor antigens. The more different HLA groups are targeted by a vaccine, the higher likelihood of the vaccine functioning in diverse populations.

The present invention regards in a preferred embodiment a vaccine composition comprising Indoleamine 2,3-dioxygenase (IDO) of SEQ ID NO: 1 or a functional homologue thereof having at least 70% identity to SEQ ID NO: 1 or an immunogenically active peptide fragment comprising a consecutive sequence of said IDO or said functional homologue thereof or a nucleic acid encoding said IDO or said peptide fragment; in combination with an adjuvant for use as a medicament. The vaccine composition may be administered to treat, prevent, or reduce the risk associated with a clinical condition in an individual.

Multi Epitope Vaccine Composition

The invention also relates to highly immunogenic multi-epitope vaccines. Preferably, such vaccines should be designed so as to facilitate a simultaneous delivery of the best-suited IDO-derived peptides optionally in combination with other suitable peptides and/or adjuvants as described hereinafter. The present invention encompasses such multi-epitope vaccines comprising IDO-derived peptides optionally in combination with further proteins or peptides fragments not belonging to or derived from IDO and/or adjuvants as described hereinafter. An important factor driving the development of vaccines having a more complex composition is the desire to target multiple tumor antigens e.g. by designing vaccines comprising or encoding a collection of carefully selected CTL and $T_h$ cell epitopes. The invention thus in one aspect relates to vaccine compositions comprising both Class I and Class II-restricted IDO epitopes.

The peptides of the present invention thus comprise both peptides in a short 'MHC-ready' form (class I restricted), and in a longer form requiring processing by the proteasome (class II restricted). Thus, the composition according to the present invention may be provided as a multiepitope vaccine comprising class I restricted epitope and/or class II restricted epitopes as defined hereinbefore.

Nucleic Acid Based Vaccine Composition

The vaccine composition according to the present invention may comprise a nucleic acid encoding a protein belonging to the IDO or an immunologically active peptide fragment thereof. Said nucleic acid may thus encode any of the above-mentioned proteins and peptide fragments. The nucleic acid may for example be DNA, RNA, LNA, HNA, PNA, preferably the nucleic acid is DNA or RNA.

The nucleic acids of the invention may be comprised within any suitable vector, such as an expression vector. Numerous vectors are available and the skilled person will be able to select a useful vector for the specific purpose. The vector may, for example, be in the form of a plasmid, cosmid, viral particle or artificial chromosome. The appropriate nucleic acid sequence may be inserted into the vector by a variety of procedures, for example, DNA may be inserted into an appropriate restriction endonuclease site(s) using techniques well known in the art. Apart from the nucleic acid sequence according to the invention, the vector may furthermore comprise one or more of a signal sequence, an origin of replication, one or more marker genes, an enhancer element, a promoter, and a transcription termination sequence. The vector may also comprise additional sequences, such as enhancers, poly-A tails, linkers, polylinkers, operative linkers, multiple cloning sites (MCS), STOP codons, internal ribosomal entry sites (IRES) and host homologous sequences for integration or other defined elements. Methods for engineering nucleic acid constructs are well known in the art (see, e.g., Molecular Cloning: A Laboratory Manual, Sambrook et al., eds., Cold Spring Harbor Laboratory, 2nd Edition, Cold Spring Harbor, N.Y., 1989). The vector is preferably an expression vector, comprising the nucleic acid operably linked to a regulatory nucleic acid sequence directing expression thereof in a suitable cell. Within the scope of the present invention said regulatory nucleic acid sequence should in general be capable of directing expression in a mammalian cell, preferably a human cell, more preferably in an antigen presenting cell.

In one preferred embodiment the vector is a viral vector. The vector may also be a bacterial vector, such as an attenuated bacterial vector. Attenuated bacterial vectors may be used in order to induce lasting mucosal immune responses at the sites of infection and persistence. Different recombinant bacteria may be used as vectors, for example the bacterial vector may be selected from the group consisting of *Salmonella, Lactococcus*], and *Listeria*. In general, induction of immunity to the heterologous antigen HPV16 L1 or E7 could be shown, with strong CTL induction and tumor regression in mice. The vector may furthermore comprise a nucleic acid encoding a T-cell stimulatory polypeptide.

Loaded APCs

In useful embodiments an immunogenic response directed against a cancer disease is elicited by administering the peptide of the invention either by loading MHC class I or class II molecules on antigen presenting cells (APCs) from the individual, by isolating PBLs from the individual and incubating the cells with the peptide prior to injecting the cells back into the individual or by isolating precursor APCs from the individual and differentiating the cells into professional APCs using cytokines and antigen before injecting the cells back into the individual.

It is thus an aspect of the invention to provide vaccine compositions comprising antigen presenting cells comprising IDO or an immunologically active peptide fragment thereof or a nucleic acid encoding said protein or said immunologically active peptide fragment. The antigen presenting cell may be any cell capable of presenting an antigen to a T-cell. Preferred antigen presenting cells are dendritic cells. The dendritic cells (DC) may be prepared and used in therapeutic procedure according to any suitable protocol, for example as described herein below. It will be appreciated by the person skilled in the art that the protocol may be adopted to use with individuals with different HLA type and different diseases.

Dendritic cells (DC) may be pulsed with 50 µg/ml HLA-restricted peptide (synthesized at GMP quality) for 1 h at 37° C. peptide and 5×10$^6$ cells are administered subcutaneously at day 1 and 14, subsequently every 4 weeks, additional leukapheresis after 5 vaccinations. The generation of DC for clinical use and quality control can be performed essentially as described in Nicolette et al., (2007).

Thus, in one embodiment of the present invention, a method for treating an individual suffering from a clinical condition characterized by the expression of IDO, preferably wherein the clinical condition is cancer or an infection, is one wherein the peptide is administered by presenting the peptide to the individual's antigen presenting cells (APCs) ex vivo followed by injecting the thus treated APCs back into the individual. There are at least two alternative ways of performing this. One alternative is to isolate APCs from the individual and incubate (load) the MHC class I molecules with the peptide. Loading the MHC class I molecules means incubating the APCs with the peptide so that the APCs with MHC class I molecules specific for the peptide will bind the peptide and therefore be able to present it to T cells. Subsequently, the APCs are re-injected into the individual. Another alternative way relies on the recent discoveries made in the field of dendritic cell biology. In this case, monocytes (being dendritic cell precursors) are isolated from the individual and differentiated in vitro into professional APC (or dendritic cells) by use of cytokines and antigen. Subsequently, the in vitro generated DCs are pulsed with the peptide and injected into the individual.

Adoptive Immunotherapy/Adoptive Transfer

An important aspect the invention relates to cultivating IDO specific T-cells in vitro and adoptive transfer of these to individuals. Adoptive transfer means that the physician directly transfers the actual components of the immune system that are already capable of producing a specific immune response, into an individual.

It is one objective to the present invention to provide IDO specific T-cells, which may be useful for example for adoptive transfer. Isolated T-cells comprising T-cell receptors capable of binding specifically to IDO peptide/MHC class I or IDO peptide/MHC class II complexes can be adoptively transferred to individuals, said T-cells preferably being T-cells that have been expanded in vitro, wherein the IDO peptide may be any of the IDO peptides mentioned herein above. Methods of expanding T-cells in vitro are well known to the skilled person. The invention also relates to methods of treatment comprising administering T-cells comprising T-cell receptors capable of binding specifically to a MHC-restricted IDO peptide complex to an individual, such as a human being suffering from a cancer disease, wherein the IDO derived peptide may be any of the IDO peptides mentioned herein above. The invention furthermore relates to use of T-cells comprising T-cell receptors capable of binding specifically to IDO or peptide fragments thereof for the preparation of a medicament for the treatment of a cancer or infection. Autologous T-cell transfer may be performed essentially as described in Walter et al., (1995).

TCR Transfer

In yet another embodiment, such T-cells could be irradiated before adoptive transfer to control proliferation in the individual. It is possible to genetically engineer the specificity of T cells by TCR gene transfer (Engels et al., 2007). This allows the transfer of T cells bearing IDO peptide specificity into individuals. In general, the use of T cells for adoptive immunotherapy is attractive because it allows the expansion of T cells in a tumor- or virus-free environment, and the analysis of T cell function prior to infusion. The application of TCR gene-modified T cells (such as T-cells transformed with an expression construct directing expressing of a heterologous TCR) in adoptive transfer has several advantages in comparison to the transfer of T cell lines: (i) the generation of redirected T cells is generally applicable. (ii) High-affinity or very high-affinity TCRs can be selected or created and used to engineer T cells. (iii) High-avidity T cells can be generated using codon optimized or murinized TCRs allowing better surface expression of the stabilized TCRs. Genetic engineering of T cell specificity by T cell receptor (TCR) gene transfer may be performed essentially as described in Morgan et al., (2006).

TCR Transfection

TCR with known anti-tumor reactivity can be genetically introduced into primary human T lymphocytes. Genes encoding TCR alpha and beta chains from a tumor specific CTL clone can be transfected into primary T cells and in this way reprogram T cells with specificity against the tumor antigen. TCR RNA is transfected into PBL by electroporation (Schaft et al., 2006). Alternatively, T cells can be provided with at new specificity by TCR gene transfer using retroviral vectors (Morgan et al., 2006). However, the provirus from the retroviral vector might integrate at random in the genome of the transfected cells and subsequently disturb cell growth. Electroporation of T cells with TCR-coding RNA overcome this disadvantage, since RNA is only transiently present in the transfected cells and can not be integrated in the genome (Schaft et al., 2006). Furthermore, transfection of cells is routinely used in the laboratory.

Adjuvants and Carriers

The vaccine composition according to the invention preferably comprises an adjuvant and/or a carrier. Examples of useful adjuvants and carriers are given herein below. Thus the IDO protein, polypeptide fragment, variant or peptide derived here from may in a composition of the present invention be associated with an adjuvant and/or a carrier.

Adjuvants are any substance whose admixture into the vaccine composition increases or otherwise modifies the immune response to the IDO or peptide fragment thereof, see further in the below. Carriers are scaffold structures, for example a polypeptide or a polysaccharide, to which the IDO or peptide fragment thereof is capable of being associated and which aids in the presentation of especially the peptides of the present invention.

Many of the peptides of the invention are relatively small molecules and it may therefore be required in compositions as described herein to combine the peptides with various materials such as adjuvants and/or carriers, to produce vaccines, immunogenic compositions, etc. Adjuvants, broadly defined, are substances which promote immune responses. A general discussion of adjuvants is provided in Coding, Monoclonal Antibodies: Principles & Practice (2nd edition, 1986) at pages 61-63. Coding notes, that when the antigen of interest is of low molecular weight, or is poorly immunogenic, coupling to an immunogenic carrier is recommended. Examples of such carrier molecules include keyhole limpet haemocyanin, bovine serum albumin, ovalbumin and fowl immunoglobulin. Various saponin extracts have also been suggested to be useful as adjuvants in immunogenic compositions. It has been proposed to use granulocyte-macrophage colony stimulating factor (GM-CSF), a well known cytokine, as an adjuvant (WO 97/28816).

A carrier may be present independently of an adjuvant. The function of a carrier can for example be to increase the molecular weight of in particular peptide fragments in order to increase their activity or immunogenicity, to confer stability, to increase the biological activity, or to increase serum half-life. Furthermore, a carrier may aid in presenting the IDO protein, polypeptide, variant or peptide fragments thereof to T-cells. The carrier may be any suitable carrier known to a person skilled in the art, for example a protein or an antigen presenting cell. A carrier protein could be, but is not limited to, keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier must be a physiologically acceptable carrier acceptable to humans and safe. However, tetanus toxoid and/or diptheria toxoid are suitable carriers in one embodiment of the invention. Alternatively, the carrier may be dextrans for example sepharose.

Thus it is an aspect of the present invention that the IDO protein, polypeptide fragment, variant or peptide derived here from present in the composition is associated with a carrier such as e.g. a protein of the above or an antigen-presenting cell such as e.g. a dendritic cell (DC).

Adjuvants could for example be selected from the group consisting of: $AIK(SO_4)_2$, $AINa(SO_4)_2$, $AINH_4 (SO_4)$, silica, alum, $Al(OH)_3$, $Ca_3 (PO_4)_2$, kaolin, carbon, aluminum hydroxide, muramyl dipeptides, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphosphoryloxy)-ethylamine (CGP 19835A, also referred to as MTP-PE), RIBI (MPL+TDM+CWS) in a 2% squalene/Tween-80® emulsion, lipopolysaccharides and its various derivatives, including lipid A, Freund's Complete Adjuvant (FCA), Freund's Incomplete Adjuvants, Merck Adjuvant 65, polynucleotides (for example, poly IC and poly AU acids), wax D from *Mycobacterium*, tuberculosis, substances found in *Corynebacterium parvum*, *Bordetella pertussis*, and members of the genus *Brucella*, Titermax, ISCOMS, Quil A, ALUN (see U.S. Pat. Nos. 58,767 and 5,554,372), Lipid A derivatives, choleratoxin derivatives, HSP derivatives, LPS derivatives, synthetic peptide matrixes or GMDP, Interleukin 1, Interleukin 2, Montanide ISA-51 and QS-21. Preferred adjuvants to be used with the invention include oil/surfactant based adjuvants such as Montanide adjuvants (available from Seppic, Belgium), preferably Montanide ISA-51. Other preferred adjuvants are bacterial DNA based adjuvants, such as adjuvants including CpG oligonucleotide sequences. Yet other preferred adjuvants are viral dsRNA based adjuvants, such as poly I:C. Imidazochinilines are yet another example of preferred adjuvants. The most preferred adjuvants are adjuvants suitable for human use.

Montanide adjuvants (all available from Seppic, Belgium), may be selected from the group consisting of Montanide ISA-51, Montanide ISA-50, Montanide ISA-70, Montanide ISA-206, Montanide ISA-25, Montanide ISA-720, Montanide ISA-708, Montanide ISA-763A, Montanide ISA-207, Montanide ISA-264, Montanide ISA-27, Montanide ISA-35, Montanide ISA 51F, Montanide ISA 016D and Montanide IMS, preferably from the group consisting of Montanide ISA-51, Montanide IMS and Montanide ISA-720, more preferably from the group consisting of Montanide ISA-51. Montanide ISA-51 (Seppic, Inc.) is oil/surfactant based adjuvants in which different surfactants are combined with a non-metabolizable mineral oil, a metabolizable oil, or a mixture of the two. They are prepared for use as an emulsion with an aqueous solution comprising IDO or peptide fragment thereof. The surfactant is mannide oleate. QS-21 (Antigenics; Aquila Biopharmaceuticals, Framingham, MA) is a highly purified, water-soluble saponin that handles as an aqueous solution. QS-21 and Montanide ISA-51 adjuvants can be provided in sterile, single-use vials.

The well-known cytokine GM-CSF is another preferred adjuvant of the present invention. GM-CSF has been used as an adjuvant for a decade and may preferably be GM-CSF as described in WO 97/28816.

Desirable functionalities of adjuvants capable of being used in accordance with the present invention are listed in the below table.

peptide composition is preferably anywhere from about 10 µg to about 5000 µg, more preferably from about 50 µg to about 2500 µg such as about 100 µg to about 1000 µg. Modes of administration include intradermal, subcutaneous and intravenous administration, implantation in the form of a time release formulation, etc. Any and all forms of administration known to the art are encompassed herein. Also any and all conventional dosage forms that are known in the art to be appropriate for formulating injectable immunogenic peptide composition are encompassed, such as lyophilized forms and solutions, suspensions or emulsion forms containing, if required, conventional pharmaceutically acceptable carriers, diluents, preservatives, adjuvants, buffer components, etc.

The pharmaceutical compositions may be prepared and administered using any conventional protocol known by a person skilled in the art. In examples 3-5 non-limiting examples of preparation of a vaccine composition according to the invention is given as well as a non-limiting example of administration of such as a vaccine. It will be appreciated by the person skilled in the art that the protocol may be

TABLE 2

Modes of adjuvant action

| Action | Adjuvant type | Benefit |
|---|---|---|
| 1. Immuno-modulation | Generally small molecules or proteins which modify the cytokine network | Upregulation of immune response. Selection of Th1 or Th2 |
| 2. Presentation | Generally amphipathic molecules or complexes which interact with immunogen in its native conformation | Increased neutralizing antibody response. Greater duration of response |
| 3. CTL induction | Particles which can bind or enclose immunogen and which can fuse with or disrupt cell membranes w/o emulsions for direct attachment of peptide to cell surface MHC-1 | Cytosolic processing of protein yielding correct class 1 restricted peptides Simple process if promiscuous peptide(s) known |
| 4. Targeting | Particulate adjuvants which bind immunogen. Adjuvants which saturate Kupffer cells Carbohydrate adjuvants which target lectin receptors on macrophages and DCs | Efficient use of adjuvant and immunogen As above. May also determine type of response if targeting selective |
| 5. Depot Generation | w/o emulsion for short term Microspheres or nanospheres for long term | Efficiency Potential for single-dose vaccine |

Source: Cox, J. C., and Coulter, A. R. (1997). Vaccine 15, 248-56.

A vaccine composition according to the present invention may comprise more than one adjuvant. Furthermore, the invention encompasses a therapeutic composition further comprising any adjuvant substance and/or carrier including any of the above or combinations thereof. It is also contemplated that the IDO protein, variants or peptide fragments thereof, and the adjuvant can be administered separately in any appropriate sequence. Preferably, the vaccine compositions of the present invention comprise a Montanide adjuvant such as Montanide ISA 51 or Montanide ISA 720 or the GM-CSF adjuvant.

Accordingly, the invention encompasses a therapeutic composition further comprising an adjuvant substance including any of the above or combinations thereof. It is also contemplated that the antigen, i.e. the peptide of the invention and the adjuvant can be administered simultaneously or separately in any appropriate sequence.

Doses and Administration

The amount of the immunogenic peptide of the invention in the pharmaceutical composition may vary, depending on the particular application. However, a single dose of the easily adapted to any of the vaccine compositions described herein. In a further embodiment of the invention, the pharmaceutical composition of the invention is useful for treating an individual suffering from a clinical condition characterized by expression of IDO, such as cancer and infections.

The immunoprotective effect of the composition of the invention can be determined using several approaches known to those skilled in the art. A successful immune response may also be determined by the occurrence of DTH reactions after immunization and/or the detection of antibodies specifically recognizing the peptide(s) of the vaccine composition.

Vaccine compositions according to the invention may be administered to an individual in therapeutically effective amounts. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular. Administration of pharmaceutical compositions is accomplished orally or parenterally. Methods of parenteral delivery include topical, intra-arterial (directly to the tissue), intramuscular, subcutaneous, intramedullary, intrathecal, intraventricular, intravenous, intraperitoneal, or intranasal administration. The present invention also has the objective of providing suitable topical, oral, systemic and parenteral pharmaceutical formulations for use in the methods of prophylaxis and treatment with the vaccine composition.

For example, the vaccine compositions can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the vaccine, comprising any of the herein described compounds can be employed as a prophylactic or therapeutic agent. Also any and all conventional dosage forms that are known in the art to be appropriate for formulating injectable immunogenic peptide composition are encompassed, such as lyophilized forms and solutions, suspensions or emulsion forms containing, if required, conventional pharmaceutically acceptable carriers, diluents, preservatives, adjuvants, buffer components, etc.

Preferred modes of administration of the vaccine composition according to the invention include, but are not limited to systemic administration, such as intravenous or subcutaneous administration, intradermal administration, intramuscular administration, intranasal administration, oral administration, rectal administration, vaginal administration, pulmonary administration and generally any form of mucosal administration. Furthermore, it is within the scope of the present invention that the means for any of the administration forms mentioned in the herein are included in the present invention.

A vaccine according to the present invention can be administered once, or any number of times such as two, three, four or five times. Administering the vaccine more than once has the effect of boosting the resulting immune response. The vaccine can further be boosted by administering the vaccine in a form or body part different from the previous administration. The booster shot is either a homologous or a heterologous booster shot. A homologous booster shot is a where the first and subsequent vaccinations comprise the same constructs and more specifically the same delivery vehicle especially the same viral vector. A heterologous booster shot is where identical constructs are comprised within different viral vectors.

Second Active Ingredient

It is an aspect of the present invention that the vaccine composition herein provided is used in combination with a second active ingredient. The administration of the vaccine composition and the second active ingredient may be sequential or combined. Examples of second active ingredients are given above for both cancers and infections. It is a further aspect that the vaccine composition may be used in combination with other therapy of relevance for the given clinical condition to be treated. Such therapy may include surgery, chemotherapy or gene therapy, immunostimulating substances or antibodies; a person skilled in the art is able to determine the appropriate combination treatment for a given scenario.

In some cases it will be appropriate to combine the treatment method of the invention with a further medical treatment such as chemotherapy, radiotherapy, treatment with immunostimulating substances, gene therapy, treatment with antibodies and/or antibiotics and treatment using dendritic cells.

Diagnostic and Prognostic Tools

The peptides of the present invention provide the basis for developing widely applicable diagnostic and prognostic procedures in respect of cancer diseases and infections. Thus, in other useful embodiments the composition of the invention is a composition for ex vivo or in situ diagnosis of the presence of IDO expressing cells in an individual. The diagnostic procedure is based on the detection of IDO reactive T cells among PBLs or in tumor tissue.

Accordingly, there is provided a diagnostic kit for ex vivo or in situ diagnosis of the presence in an individual of IDO reactive T cells among PBLs or in tumour tissue comprising one or more peptides of the invention, and a method of detecting in an individual the presence of such reactive T cells, the method comprising contacting a tumour tissue or a blood sample with a complex of a peptide of the invention and a Class I or Class II HLA molecule or a fragment of such molecule and detecting binding of the complex to the tissue or the blood cells. In one aspect, the invention provides a complex of a peptide of the invention and a Class I or Class II HLA molecule or a fragment of such molecule, which is useful as a diagnostic reagent such as it is described herein. Such a complex may be monomeric or multimeric.

Another useful diagnostic or prognostic approach is based on generating antibodies in a heterologous animal species, e.g. murine antibodies directed against a human IDO-derived peptide of the invention, which can then be used, e.g. to diagnose for the presence of cancer cells presenting the peptide. For such immunization purposes, the amount of peptide may be less than that used in the course of in vivo therapy, such as that mentioned above. In general, a preferred dose can range from about 1 μg to about 750 μg of peptide. It is also possible to produce monoclonal antibodies based on immunization with a peptide of the invention. Accordingly, the present invention also relates to a molecule, in particular a monoclonal or polyclonal antibody including a fragment hereof, that is capable of binding specifically to a peptide of the invention and to a molecule that is capable of blocking such a binding, e.g. an antibody raised against the monoclonal or polyclonal antibody directed against a peptide of the invention. The invention furthermore relates to isolated T-cell receptors capable of binding specifically to a peptide or a protein of the invention as well as to isolated nucleic acids encoding same. Such T-cell receptors may for example be cloned from protein or peptide specific T-cells using standard techniques well known to the skilled person.

In one aspect the invention also relates to isolated T-cells comprising T-cell receptors capable of binding specifically to IDO and/or peptide fragments thereof described herein. The isolated T-cells may be CD8 T-cells or CD4 T-cells. The isolated T-cells are preferably T-cells that have been expanded in vitro. Methods of expanding T-cells in vitro are well known to the skilled person. Such T-cells may in particular be useful in the treatment of cancer by adaptive transfer or autologous cell transfer. Thus, the invention also relates to pharmaceutical compositions comprising T-cells as well as methods of treatment comprising administering T-cells comprising T-cell receptors capable of binding specifically to IDO or peptide fragments thereof to an individual, in need thereof such as an individual suffering from cancer and/or infections. Autologous cell transfer may be performed essentially as described in Walter et al., (1995).

The present invention provides the means for treating, preventing, alleviating or curing a clinical condition characterized by expression of IDO such as cancers and infections preferably a cancer, comprising administering to an individual suffering from the disease an effective amount of a composition as defined herein, a molecule that is capable of binding specifically to a peptide fragment, which may for example be an antibody or a T-cell receptor or the kit-of-parts described herein. Accordingly, it is a further aspect of the invention to provide a method of treating a clinical condition associated with the expression of IDO of SEQ ID NO: 1 and/or SEQ ID NO: 16.

Monitoring Immunization

In preferred embodiments, the pharmaceutical composition of the invention is a vaccine composition. It is therefore of interest, and an aspect of the present invention to monitor the immunization in an individual to whom the vaccine composition of the present invention is administered. The pharmaceutical composition may thus be an immuno-genic composition or vaccine capable of eliciting an immune response to a cancer and/or infection. As used herein, the expression "immunogenic composition or vaccine" refers to a composition eliciting at least one type of immune response directed against IDO expressing cells such as cancer cells, APCs or DCs. Thus, such an immune response may be any of the following: A CTL response where CTLs are generated that are capable of recognizing the HLA/peptide complex presented on cell surfaces resulting in cell lysis, i.e. the vaccine elicits the production in the vaccinated subject of effector T-cells having a cytotoxic effect against the cancer cells; a B-cell response giving rise to the production of anti-cancer antibodies; and/or a DTH type of immune response. It is on object of the present invention to monitor the immunization of an individual by monitoring any of the above reactions subsequent to administering the composition of the present invention to said individual.

In one aspect the invention relates to methods of monitoring immunization, said method comprising the steps of
i) providing a blood sample from an individual
ii) providing IDO or a peptide fragment hereof, wherein said protein or peptide may be any of the proteins or peptides described herein
iii) determining whether said blood sample comprises antibodies or T-cells comprising T-cell receptors specifically binding the protein or peptide
iv) thereby determining whether an immune response to said protein or peptide has been raised in said individual.

The individual is preferably a human being, for example a human being that has been immunized with IDO or a peptide fragment hereof or a nucleic acid encoding said protein or peptide.

Kit of Parts

The invention also relates to a kit-of-parts comprising any of the vaccine compositions described herein and/or an IDO protein or variant hereof and/or
any of the polypeptide fragments of IDO, variant hereof, and/or peptides derived here from as described herein and/or
any of the nucleic acids encoding the proteins of the above two bullet points and instructions on how to use the kit of parts.

The invention also relates to a kit-of-parts comprising any of the vaccine compositions described herein and/or an IDO protein or variant hereof and/or
any of the polypeptide fragments of IDO, variant hereof, and/or peptides derived here from as described herein and/or
any of the nucleic acids encoding the proteins of the above two bullet points and a second active ingredient.

Preferably, the second active ingredient is chosen in correspondence with the clinical condition to be treated so that in the case where a cancer is to be treated the second active ingredient is chosen among e.g. chemotherapeutic agents as listed above. Likewise, if treating a microbial/viral infection, the second active ingredient is preferably an anti-biotic and/or an anti-viral agent.

The components of the kit-of-parts are preferably comprised in individual compositions, it is however within the scope of the present invention that the components of the kit-of-parts all are comprised within the same composition. The components of the kit-of-parts may thus be administered simultaneously or sequentially in any order.

DETAILED DESCRIPTION OF THE DRAWINGS

FIG. 1: HLA-A2-restricted T cell responses against IDO as measured by IFN-γ ELISPOT. PBL from 13 healthy individuals, 4 breast cancer patients, 6 melanoma patients, and 10 renal cell carcinoma patients were analyzed. All individuals were HLA-A2 positive. The peptides IDO2 (FLVSLLVEI) (SEQ ID NO: 3) (a), IDO6 (VLSKGDGL) (SEQ ID NO: 7) (b), and IDO5 (ALLEIASCL) (SEQ ID NO: 6)(c) were examined. T lymphocytes were stimulated once with peptide before being plated at $4 \times 10^5$ cells per well in duplicates either without or with the relevant peptide. The average number of peptide-specific spots (after subtraction of spots without added peptide) was calculated for each patient using the ImmunoSpot Series 2.0 Analyzer (CTL Analyzers) (d) The number of IDO5-specific cells in PBMC measured by IFN-γ ELISPOT in correlation to IDO expression in the PBMC measured by intracellular IDO stainings. Patients were divided into two groups hosting; IDO− PBMC or IDO+ PBMC. Intracellular IDO expression was given by a onetailed two sampled T-test comparing MFIIDO and MFIIsotype control, where MFI is the Mean Fluorescence Intensity. For p-values<0.05 (significance level) PBMC were defined IDO+. White triangle gives the average number of IDO5-specific spots per $4 \times 10^5$ PBMC in each group. Black triangles indicate the average number of IDO5-specific spots in each group (e) Example of an ELISPOT response against IDO5 in PBMC from a breast cancer patient.

FIG. 2: Tetramer analysis of IDO5-specific T cells. (a), The binding of the HLA-A2-restricted positive control peptide HIV-1 pol$_{476-484}$ (ILKEPVHGV) was compared with the peptide IDO5 by an assembly assay. (b), An example of IDO5-specific, CD8 T cells in PBL from a renal cell carcinoma patient visualized by flow cytometry staining using the tetramer complex HLA-A2/IDO5-PE, and CD8-allophycocyanin. As a negative control, PBL from the same patient were stained with the tetramer complex HLA-A2/HIV pol476-484-PE, and CD8-allophycocyanin. (c), PBL from healthy donors or from patients with breast cancer, melanoma cancer or renal cell carcinoma were stained with the tetramer complex HLA-A2/IDO5 or HLA-A2/HIV pol and analyzed by flow cytometry either ex vivo or after one in vitro peptide stimulation. The dotted lines illustrate that IDO5 tetramer positive cells are detectable both ex vivo and in vitro in the same patients. (d), An example of CD45RA and CD28 phenotype analysis of IDO5 tetramer/CD8 gated cells from CD8 T cell enriched PBMC from a renal cell carcinoma patient visualised ex vivo by flow cytometry. For comparison, the cells were stained with isotype matched controls (e), An example of an IL-2 expanded TIL culture from a melanoma patient visualised by flow cytometry staining using the tetramer complex HLAA2/IDO5-PE, and CD8-APC-Cy7. As a negative control, the TILs were stained with the tetramer complex HLA-A2/HIV pol476-484-PE, and CD8-APC-Cy7. (f), As a positive control of the IDO5 tetramer, an IDO5-specific T-cell clone was stained with the HLA-A2/HIV-PE and HLA-A2/IDO5-PE tetramers.

FIG. 3: Specificity and functional capacity of an IDO5-specific T-cell clone. (RBS35) assayed by $^{51}$Cr-release assay. (a), Lysis of T2-cells with no peptide or pulsed with IDO5 peptide. (b), Specific lysis of the IDO+, HLA-A2+ colon cancer cell line SW480 without or with the addition of the HLA-class I specific antibody W6/32, and lysis of the IDO-, HLA-A2+ colon cancer cell line HCT-116. (c), Lysis of the IDO+, HLA-A2+ melanoma cell line FM55M without and with the addition of cold T2-cells pulsed with IDO5 or unpulsed (inhibitor to target ratio=20:1) (d), Lysis of AML-blasts enriched from an HLA-A2 positive AML patient. AML-blasts, B cells, and T cells were depleted from the bone marrow of the AML patient using CD19$^+$ and CD3$^+$ microbeads, respectively. The highly enriched AML-blasts were used as target cells with or without the addition of the HLA-class I specific antibody W6/32. All assays were performed in different E:T ratios. (e) Histograms showing intracellular IDO expression in cancer cell lines. Data are representative of 3 experiments. Intracellular IDO expression was given by a one-tailed two sampled T-test comparing MFIIDO (dark histograms) and MFIisotype control (light histograms), where MFI is the Mean Fluorescence Intensity. Left: HCT-116 (p=0.300). Right: SW480 (p=0.002).

Figure 4A:
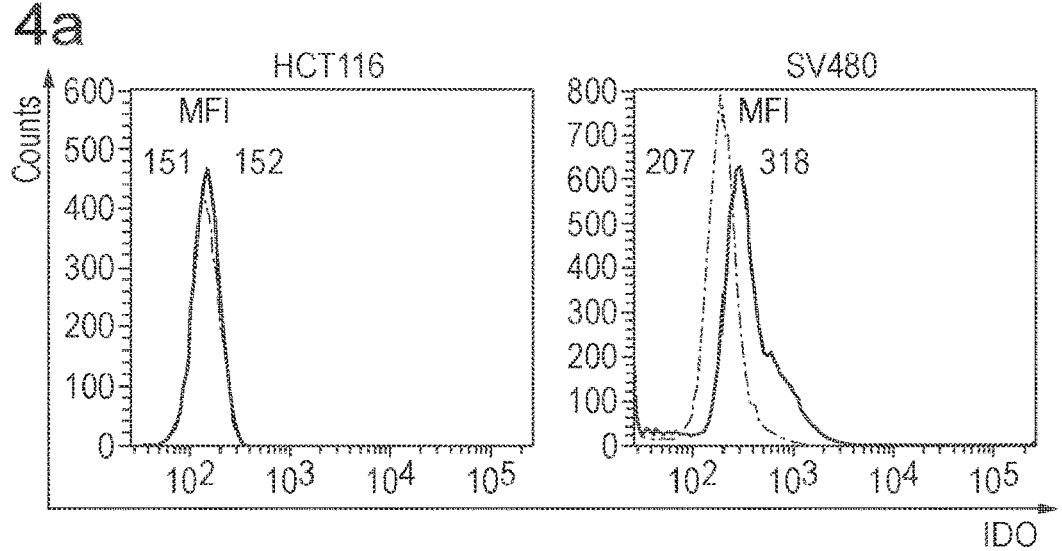
FIG. 4a shows histograms of intracellular IDO stainings (dark histograms) in colon cancer cell lines HCT-116 (0,01), and SW480 (1,3). Negative controls were stainings with the secondary fluorochrome conjugated antibody alone (light histograms). The IDO expression was determined using the staining index defined as $MFI_{positive} - MFI_{background}/2 \times SD_{background}$ where MFI is mean fluorescence intensity. Cells were defined IDO positive if the staining index>1.
Figure 4B:
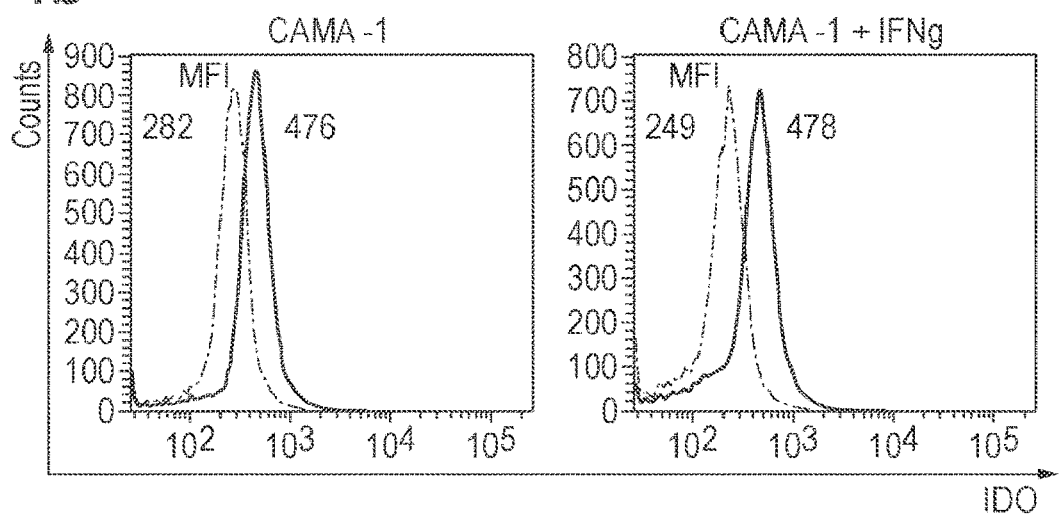
FIG. 4b shows histograms of intracellular IDO stainings (dark histograms) in breast cancer cell lines CAMA-1 (1,3), and CAMA-1+IFN-γ (1,8). Negative controls were stainings with the secondary fluorochrome conjugated antibody alone (light histograms). Cells were defined IDO positive if the staining index>1.
Figure 4C:
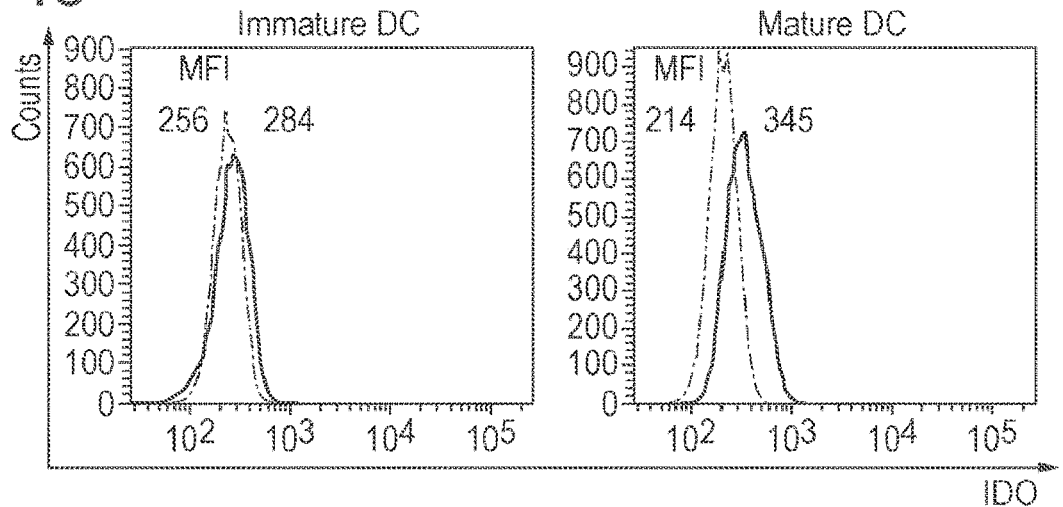
FIG. 4c shows histograms of intracellular IDO stainings (dark histograms) in immature dendritic cells (DC) (0,2), and mature dendritic cells (DC)(1,2). Negative controls were stainings with the secondary fluorochrome conjugated antibody alone (light histograms). Cells were defined IDO positive if the staining index>1.

FIG. 4: Histograms show intracellular IDO stainings (dark histograms). Negative controls were stainings with the secondary fluorochrome conjugated antibody alone (light histograms). The IDO expression was determined using the staining index defined as $MFI_{positive}-MFI_{background}/2\times SD_{background}$ where MFI is mean fluorescence intensity. Cells were defined IDO positive if the staining index>1$^{21}$. (a), Colon cancer cell lines HCT-116 (0.01), and SW480 (1.3) (b), breast cancer cell line CAMA-1 (1.3), and CAMA-1+IFN-γ (1.8), and (c), immature DC (0.2), and mature DC (1.2).

FIG. 5: Functional capacity of an IDO5-specific T-cell clone (RBS35) to kill IFN-γ treated breast cancer cell lines assayed by $^{51}$Cr-release assay. Lysis of the HLA-A2 positive breast cancer cell lines CAMA-1 (a) and MDA-MB-231 (b) before and after IFN-γ treatment. All assays were performed in different E:T ratios. (c), Left: Histograms showing intracellular IDO expression in CAMA-1 before and after IFN-γ treatment. Data are representative of 3 experiments. Intracellular IDO expression was given by a one-tailed two sampled T-test comparing MFIIDO (dark histograms) and MFIisotype control (light histograms), where MFI is the Mean Fluorescence Intensity. Top: CAMA-1 (p=0.020 and MFIIDO/MFIisotype control=2.3). Bottom: CAMA-1+IFN-γ treatment 25 (p=0.004 and MFIIDO/MFIisotype control=3.5). Right: Histograms showing HLA-A2 expression in CAMA-1 before and after IFN-γ treatment. Data are representative of 3 experiments. HLA-A2 expression was given by a one-tailed two sampled T-test comparing MFIHLA-A2 (dark histograms) and MFIisotype control (light histograms). Top: CAMA-1 (p=0.004 and MFIHLA-A2/MFIisotype control=43.7). Bottom: CAMA-1+IFN-γ treatment (p=0.002 and MFIIDO/MFIHLA-A2=141.2). (d), Lysis of the colon cancer cell line SW480 transfected with IDO ShRNA for down-regulation of IDO protein expression by an IDO5-specific T-cell bulk culture. As a positive control, SW480 cells transfected with control ShRNA were used as target cells. All assays were performed in different E:T ratios. (d), Histograms showing intracellular IDO expression in SW480 transfected with control ShRNA (p=0.001 and MFIIDO/MFIIsotype control=4.8) (top) and IDO ShRNA (p=0.040 and MFIIDO/MFIIsotype control=2.1) (bottom).

FIG. 6: Functional capacity of an IDO5-specific T-cell clone (RBS35) to kill DC assayed by $^{51}$Cr-release assay. (a), Lysis of autologous immature and mature DC. (b), Lysis of HLA-A2+ allogeneic immature and mature DC. All assays were performed in different E:T ratios. (c), Histograms showing intracellular IDO expression in DC. Data are representative of 3 experiments. Intracellular IDO expression was given by a one-tailed two sampled T-test comparing MFIIDO (dark histograms) and MFIisotype control (light histograms), where MFI is the Mean Fluorescence Intensity. Left: In vitro immatured DC (p=0.100). Right: In vitro matured DC (p=0.001). (d), Lysis of autologous CD14+ monoctyes, CD3+ T cells and CD19+ B cells isolated directly ex vivo from IDO+ PBMC. As a control, we used in vitro generated autologous IDO− immatured DC and IDO+ matured DC. (e), Examples of HLA-A2 restricted T-cell responses against EBV BMLF1280-288 (GLCTLVAML) (SEQ ID NO: 19) as measured by ELISPOT in PBMC from a breast cancer patient. Cultures of PBMC were treated with IFN-γ for 5 days without (left) and with 26 IDO-specific T cells (at a PBMC:IDO-specific T cell ratio of 3000:1) (right) before examination for reactivity against the HLA-A2 restricted epitope from EBV BMLF1 (GLCTLVAML) (SEQ ID NO: 19). Three different PMBC concentrations was examined; 1.5×10$^5$ cells, 5×10$^4$ cells (two top rows) and 10$^4$ cells (bottom two rows).

FIG. 7: Specificity and functional capacity of IDO5-specific T cells assayed by 51Cr-release assays: (a), Lysis by RBS35 of the HLA-A2+/IDO+ melanoma cell line FM55M without and with the addition of cold T2-cells pulsed with IDO5 peptide or an irrelevant peptide (HIV-1 pol476-484) (inhibitor to target ratio=20:1), and NK cell activity of RBS35 examined using the natural killer cell line K562 as target cells. (b), Lysis by RBS35 of AML-blasts enriched from an HLA-A2+ AML patient. AML-blasts, B cells, and T cells were depleted from the bone marrow of the AML patient using CD19+ and CD3+ microbeads, respectively. The highly enriched AML-blasts were used as target cells with or without the addition of the HLA-class I specific antibody W6/32. (c), Lysis of T2-cells pulsed with IDO5 peptide or an irrelevant peptide (HIV-1 pol476-484), and lysis of the HLAA2+/IDO+ colon cancer cell line SW480 by an IDO5-specific T-cell bulk culture. (d), Lysis of the HLA-A2+/IDO+ colon cancer cell line SW480 and HLA-A2+/IDO− colon cancer cell line HCT-116 by three different IDO5-specific T-cell clones (RBS26 (white triangle), RBS31 (black triangle), RBS46 (grey triangle)) assayed by 51Cr-release assay. All assays were performed in different E:T ratios.

FIG. 8: Multiple alignment of IDO sequences by Clustal W

FIG. 9: Pair wise alignment of IDO and IDOLIKE by Clustal W

EXAMPLES

Example 1

Patients/Individuals

PBL/PBMC was collected from cancer patients (breast cancer, melanoma, and renal cell carcinoma) and healthy controls. Blood samples were drawn a minimum of four weeks after termination of any kind of anti-cancer therapy. The majority of renal cell carcinoma patients had previously been treated with IL2 and IFN-α, most melanoma patients had received high dose IL2 and IFN-α, while all breast cancer patients were pre-treated with several kinds of chemotherapy, (e.g. epirubicin, docetaxel, cabecitabine), trastuzumab, and/or endocrine therapy. PBL were isolated using Lymphoprep separation, HLA-typed (Department of Clinical Immunology, University Hospital, Copenhagen, Denmark) and frozen in FCS with 10% DMSO. A total of 20 HLA-A2+ patients were included, none of these received immunotherapy prior to sampling of blood. Informed consent was obtained from the patients prior to any of theses measures.

Peptides

Epitopes from IDO were predicted according to knowledge about preferred peptide-length, anchor residues and auxiliary anchors of the HLA-A2 allele. Scanning of the IDO protein was carried out using the "Database SYF-PEITHIP"[32] in combination with manual examination of the protein sequence for MHC class I anchor residues. Selected peptides were purchased from Genscript. Eleven synthetic 9mer and 10mer peptides were produced: IDO1 positions 54-62 (QLRERVEKL (SEQ ID NO: 2)), IDO2 positions 164-172 (FLVSLLVEI (SEQ ID NO: 3)), IDO3 positions 195-203 (TLLKALLEI (SEQ ID NO: 4)), IDO4 positions 41-49 (FIAKHLPDL (SEQ ID NO: 5)), IDO5 positions 199-207 (ALLEIASCL (SEQ ID NO: 6)), IDO6 positions 320-328 (VLSKGDGL (SEQ ID NO: 7)), IDO7 positions 383-391 (DLMNFLKTV (SEQ ID NO: 8)), IDO8 positions 275-283 (VLLGIQQTA (SEQ ID NO: 9)), IDO9 positions 101-109 (KVLPRNIAV (SEQ ID NO: 10)), IDO10 positions 61-70 (KLNMLSIDHL (SEQ ID NO: 11)), and IDO11 positions 341-350 (SLRSYHLQIV (SEQ ID NO: 12)). The peptides were dissolved in DMSO (final concentration 10 mM) or distilled water (final concentration 2 mM). The HLA-A2 high affinity binding epitope HIV-1 pol476-484 (ILKEPVHGV (SEQ ID NO: 18)) was used as irrelevant control. The HLA-A2 restricted Epstein—Barr virus peptide EBVBMLF1280-288 (GLCTLVAML (SEQ ID NO: 19)) was used as control.

Assembly Assay for Peptide Binding to MHC Class I Molecules

The binding affinity of the synthetic peptides (Genscript) to HLA-A2 molecules, metabolically labelled with [$^{35}$S]-methionine, was measured in the assembly assay, as described previously[33]. The assay is based on peptide-mediated stabilization of empty HLA-molecules released upon cell lysis, from the TAP-deficient cell line T2. Stably folded HLA-molecules were immune-precipitated by using the HLA class-I specific, conformation dependent monoclonal (mAb) W6/32 and separated by isoelectric focusing (IEF) gel electrophoresis. Major histocompatibility complex (MHC) heavy-chain bands were quantified using the ImageGauge Phosphoimager program (FUJI Photo Film, Carrolton, TX). The intensity of the band is directly related to the amount of peptide-bound class I MHC complex recovering during the assay. The recovery of HLA-A2 was measured in presence of 100, 10, 1, and 0.1 µM of the relevant peptide. The C50 value was calculated for each peptide as the peptide concentration sufficient for half maximal stabilization.

Antigen Stimulation of PBL

To extend the sensitivity of the enzyme-linked immunospot (ELISPOT) assay, PBL were stimulated once in vitro with peptide prior to analysis[34]. At day 0, PBL were thawed and plated in 2 ml/well at a concentration of 2×106 cells in 24-well plates (Nunc) in X-vivo medium (BioWhittaker) with 5% heat-inactivated human serum in the presence of 10 µM peptide (GenScript). One day later 40 IU/ml recombinant interleukin-2 (IL-2) (PeproTech) was added to the cultures. The cultured cells were tested in the IFN-γ ELISPOT assay on day 8.

IFN-γ ELISPOT Assay

The ELISPOT assay was used to quantify peptide epitope-specific INF-γ releasing effector cells as described previously[17]. In some experiments PBMC were stimulated once in vitro with peptide prior to analysis as described[(34)] to extend the sensitivity of the assay. Briefly, nitrocellulose bottomed 96-well plates (MultiScreen MAIP N45; Millipore) were coated with anti-IFN-γ Ab (1-D1K; Mabtech). The wells were washed, blocked by X-vivo medium and the effector cells were added in duplicates at different cell concentrations, with or without 10 µM peptide. The plates were incubated overnight. The following day, medium was discarded and the wells were washed prior to addition of biotinylated secondary Ab (7-B6-1-Biotin; Mabtech). The plates were incubated at room temperature (RD for 2 h, washed, and Avidin-enzyme conjugate (AP-Avidin; Calbiochem/Invitrogen Life Technologies) was added to each well. Plates were incubated at RT for 1 h and the enzyme substrate NBT/BCIP (Invitrogen Life Technologies) was added to each well and incubated at RT for 5-10 min. Upon the emergence of dark purple spots, the reaction was terminated by washing with tap water. The spots were counted using the ImmunoSpot Series 2.0 Analyzer (CTL Analyzers) and the peptide-specific CTL frequency could be calculated from the numbers of spot-forming cells.

Flow Cytometry

For tetramer stainings, PBL from cancer patients and healthy donors as well as TIL from cancer patients were stimulated once in vitro with peptide, or analysed directly ex vivo. The CD8 cells were isolated from PBL using the Dynal CD8 negative isolation kit (Dynal Biotech) at day 7. The resulting T cell cultures were stained with PE coupled tetramer, followed by antibody staining with the flourochrome-coupled mAbs: CD8-allophycocyanin/APC-Cy7, CD3-FITC, CD3-FITC, CD45RO-FITC, CD45RA-PE-Cy5 and CD28-allophycocyanin (BD Immunocytometry Systems). Tetramer stainings were performed in PBS+2% FCS, for 15 min, RT, in the dark, whereas antibody stainings were performed in PBS+2% FCS, 4° C., in the dark. The MHC tetramer complexes used were: HLA-A2/IDO5 (ALLEIASCL (SEQ ID NO: 20)) and HLA-A2/HIV-1 pol476-484 (ILKEPVHGV (SEQ ID NO: 18)). The samples were analyzed on BD FACS aria, using DIVA software (BD Biosciences).

Cancer cell lines and DC were examined for expression of IDO using flow cytometry. After fixation and permeabilization (Cytofix/Cytoperm, BD), cells were stained with mouse anti-IDO antibody (Millipore Corporation) followed by FITC-labeled anti-mouse secondary antibody (DAKO). For all experiments, a negative control only stained with the FITC-coupled secondary antibody was included, to determine the background fluorescence from falsely attached secondary antibodyE and auto-fluorescence. The IDO expression was determined using the staining index defined as MFIpositive−MFIbackground/2×SDbackground where MFI is mean fluorescence intensity. Cells were defined IDO positive if the staining index>1[21].

Cancer cells were examined for HLA-A2 expression using flow cytometry. Cells were stained with a fluorochrome-coupled HLA-A2 mAb (BD Bioscience). For comparison, cells were stained with an isotype matched control. The samples were analyzed on BD FACS aria, using DIVA software (BD Biosciences). Assuming normality, HLA-A2 expression was given by a one-tailed two sampled T-test comparing MFIHLA-A2 and MFIisotype control, where MFI is the Mean Fluorescence 9 Intensity. For p-values<0.05 (significance level) cells were defined HLA-A2+. The fold of expression was defined as MFIHLA-A2/MFI-Isotype control.

Dendritic Cells (DC)

DC were generated from PBMC by adherence on culture dishes at 37° C. for 60 min in RPMI-1640 enriched with 10% human AB serum. Adherent monocytes were cultured in RPMI-1640 supplemented with 10% human AB serum in the presence of IL-4 (1000 U/ml) and GM-CSF (800 U/ml) for 6 days. DC were matured by addition of IL-1β (2 ng/ml), IL-6 (1000 U/ml), TNF-α (10 ng/ml), and PGE2 (1 μg/ml).

Establishment of Antigen Specific T-Cell Cultures and Clones

PBL from cancer patients were stimulated with irradiated (25 Gy), IDO5-loaded autologous DC (PBL:DC ratio=3× 106: 3×105), with 3 μg/ml 112m, 20U/ml IL-12 (PeproTech), and 40 U/ml IL-7 (PeproTech). The cultures got stimulated every 10 days with irradiated autologous DC (2×) followed by irradiated PBL (2×). 20U/ml IL-12 (PeproTech) and 40 U/ml IL-7 (PeproTech) was added after each stimulation with DC, and 40 U/ml IL-2 (PeproTech) was added after each stimulation with PBL. After one month growing cultures were tested for specificity for IDO5 in a standard 51Cr-release assay. PBL from a specific culture were cloned by limiting dilution in the presence of 106/ml irradiated (25 Gy) IDO5 loaded PBL, and 120 U/ml IL-2 (PeproTech). Every 3-4 days 50 μl fresh media were added containing IL-2 to a final concentration of 120 U/ml. Growing clones were expanded using IDO5 loaded PBL (5×10$^4$ cells/well) and 120 U/ml IL-2. After expansion the clones were tested for specificity and cytotoxic potential in a standard $^{51}$Cr-release assay.

Cytotoxicity Assay

Conventional $^{51}$Cr-release assays for CTL-mediated cytotoxicity was carried out as described elsewhere[35]. Target cells were T2-cells, in vitro generated autologous immature and mature DC, allogeneic HLA-A2 positive immature and mature DC, autologous ex vivo isolated monocytes, T cells and B cells (isolated using CD14+, CD3+ or CD19+ microbeads (MACS)), the natural killer target cell line K562,ex vivo enriched HLA-A2 positive AML-blasts (isolated from the bone marrow of the AML patient using CD19+ and CD3+ microbeads (MACS)), the HLA-A2 positive breast cancer cell lines CAMA-1 and MDA-MB-231, the HLA-A2 positive colon cancer cell lines HCT-116 and SW480 (all available at the American Type Culture Collection (ATCC)), and the HLA-A2 positive melanoma cell line FM55M (from the IPD-ESTDAB database, available at www.ebi.ac.uk/cgi-bin/ipd/estdab/[36]). Lysis were blocked using the HLA specific mAb W6/32 (2 μg/100 μl)[37]. In some assays, cancer cells were treated with 100 U/ml IFN-γ for 2 days.

Enrichment of AML Blasts

We depleted B and T cells from the bone marrow of the AML patient using CD19+ and CD3+ microbeads (MACS), respectively. The highly enriched AML-blasts (CD3−, CD19−) were used as target cells in a standard $^{51}$Cr release assay.

Down-Regulation of IDO in Cancer Cells

Human SW480 were transfected with indicated short hairpin RNA (ShRNA) plasmids obtained from SuperArray using FuGene6 (Roche) according to manufacturers instructions. Cells were lysed directly in LSB buffer (Sigma). The LSB lysates were boiled for 5 min. and loaded on 10% precast protein gels (BioRad). Proteins were electro transferred to a PVDF membrane (Millipore Corporation) by a semidry transfer method and probed with indicated antibodies according to manufacturers instructions. Blots were developed with the ECL system obtained from Amersham and a CCD camera (LAS-1000, Fujifilm). Following antibodies were used: anti-Cdk7 (MO-1) (Santa Cruz) and anti-IDO (Millipore Corporation).

IDO-Derived HLA-A2-Restricted T-Cell Epitopes

Eleven IDO-derived peptides were selected using algorithms based on the main HLA-A2 specific anchor residues and subsequently synthesized[16]. Using the ELISPOT IFN-γ secretion assay, we then examined peripheral blood T cells from cancer patients and healthy individuals for the presence of specific T-cell responses against these IDO− derived peptides. This approach has previously proved to be highly effective for identifying tumor specific cytotoxic T-lymphocytes (CTL) in cancer patients[17-19]. Thus, peripheral blood lymphocytes (PBL) from HLA-A2 positive, late stage cancer patients (breast cancer, melanoma and renal cell carcinoma) were stimulated once with the different peptides in vitro before examination by ELISPOT. This procedure was chosen to extend the sensitivity of the ELISPOT as described[17,20]. ELISPOT responses were detected against IDO2 (IDO164-172; FLVSLLVEI (SEQ ID NO: 3)), IDO6 (IDO 320-328; VLSKGDGL (SEQ ID NO: 7)), and especially IDO5 (IDO199-207; ALLEIASCL (SEQ ID NO: 6)) (FIG. 1). As control, we examined PBL from healthy individuals for reactivity against these three IDO derived peptides. No spontaneous responses could be detected against any of the IDO derived peptides in any of the healthy controls. A BLAST search of the amino acid sequences of these peptides using the "NCBI database" showed that these motifs are only prevalent in the IDO protein.

Example 2

(Materials and Methods are as Described in Example 1)

Detection of IDO-Reactive HLA-A2-Restricted T Cells in Cancer Patients

Figure 1A:
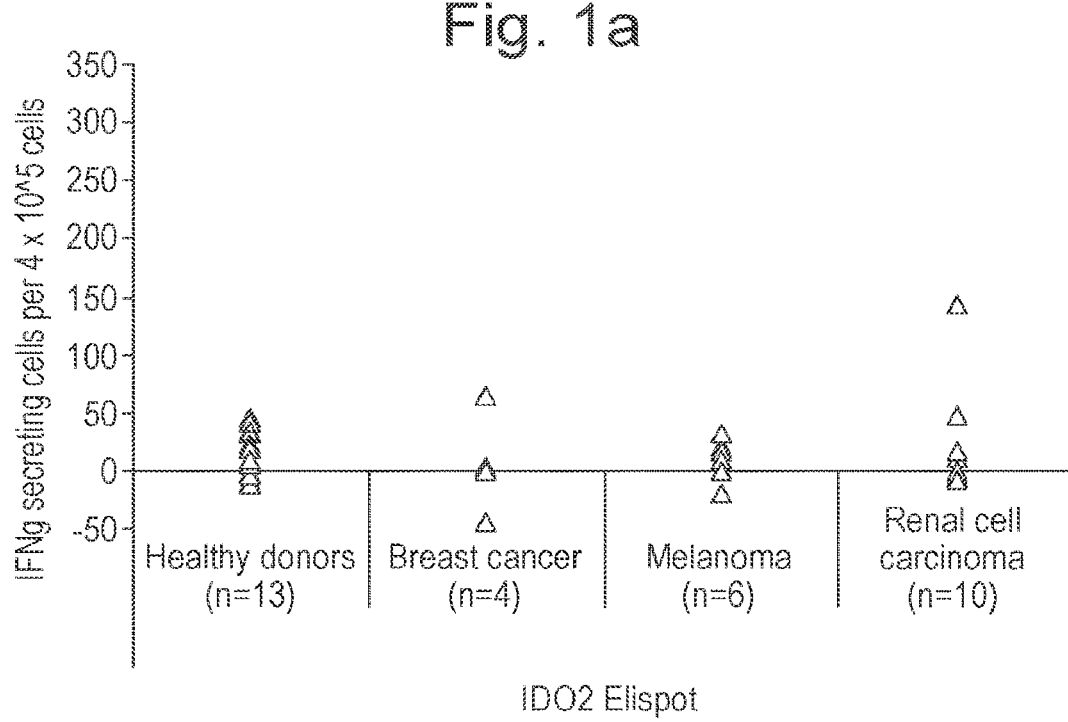
FIG. 1a shows HLA-A2-restricted T cell responses against IDO as measured by IFN-γ ELISPOT. PBL from 13 healthy individuals, 4 breast cancer patients, 6 melanoma patients, and 10 renal cell carcinoma patients were analyzed. All individuals were HLA-A2 positive. T lymphocytes were stimulated once with peptide IDO2 (FLVSLLVEI) (SEQ ID NO: 3) before being plated at $4 \times 10^5$ cells per well in duplicates either without or with the peptide. The average number of peptide-specific spots (after subtraction of spots without added peptide) was calculated for each patient using the ImmunoSpot Series 2.0 Analyzer (CTL Analyzers).
Figure 1B:
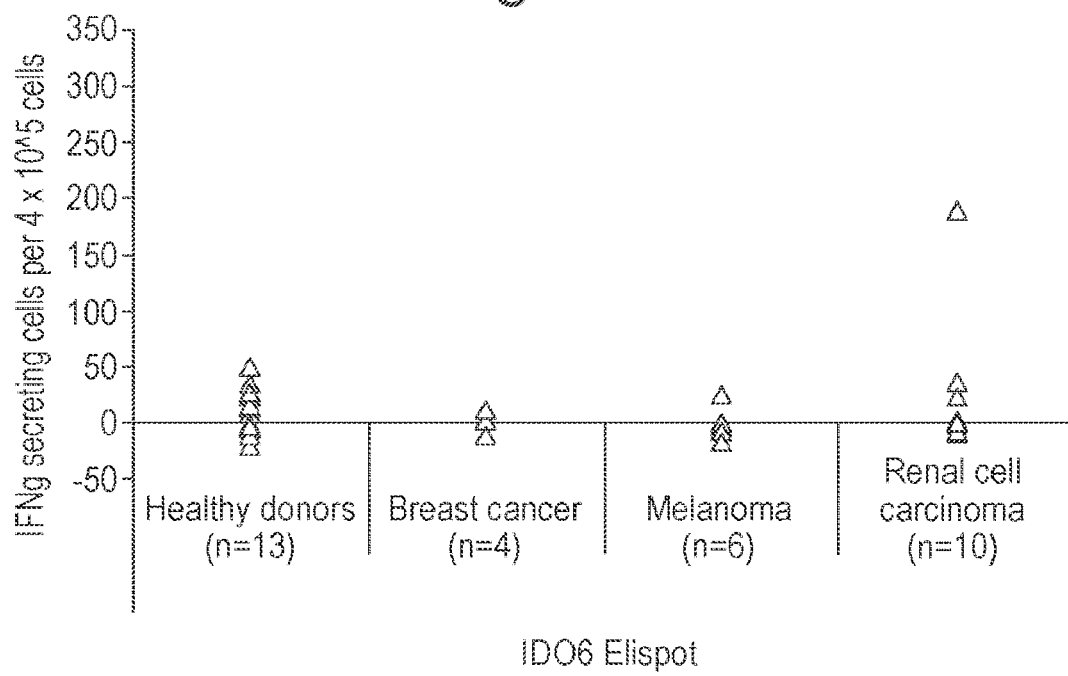
Figure 1C:
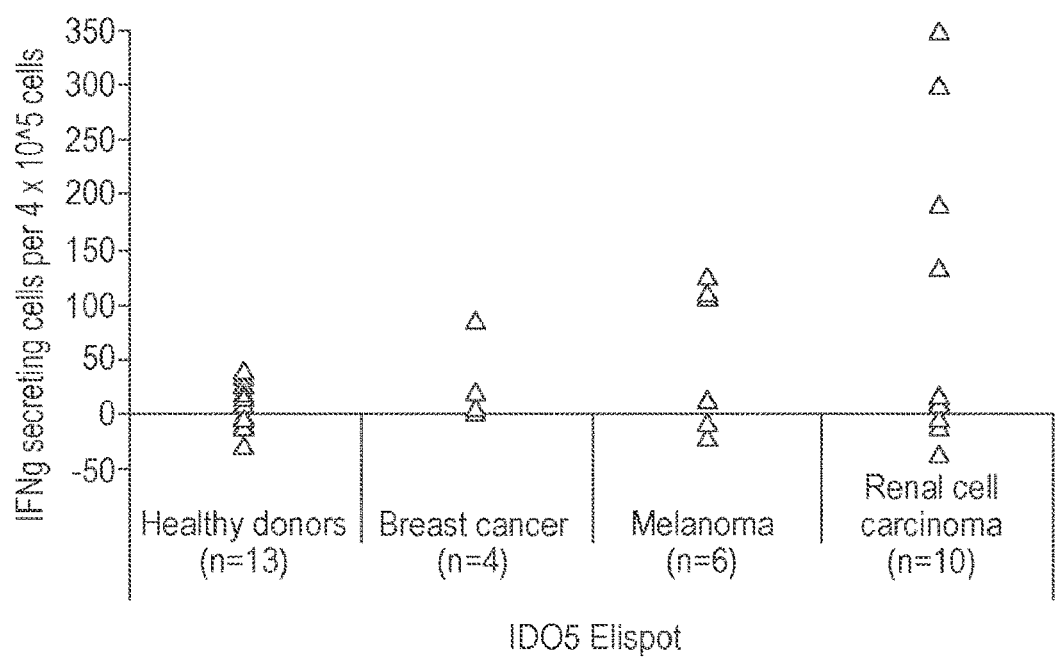
Figure 1D:
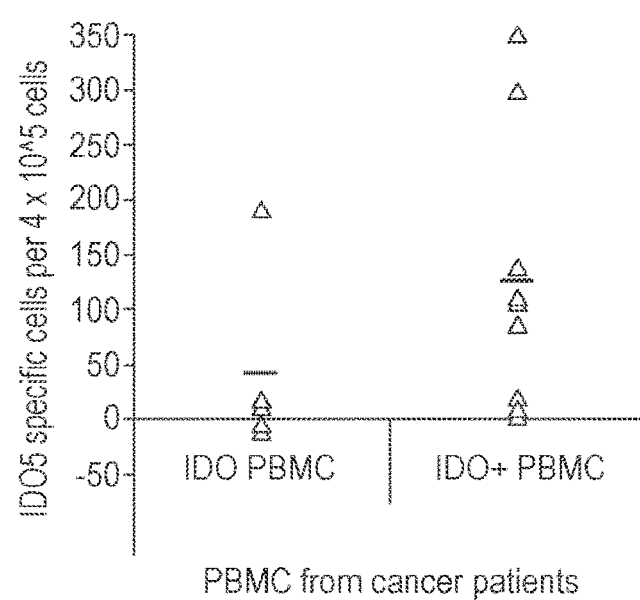
FIG. 1d shows the number of IDO5-specific cells in PBMC measured by IFN-γ ELISPOT in correlation to IDO expression in the PBMC measured by intracellular IDO stainings.
Figure 1E:
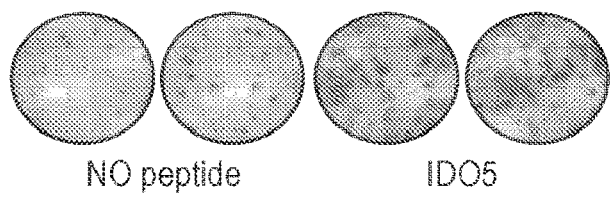
FIG. 1e shows an example of an ELISPOT response against IDO5 in PBMC from a breast cancer patient.
Figure 2A:
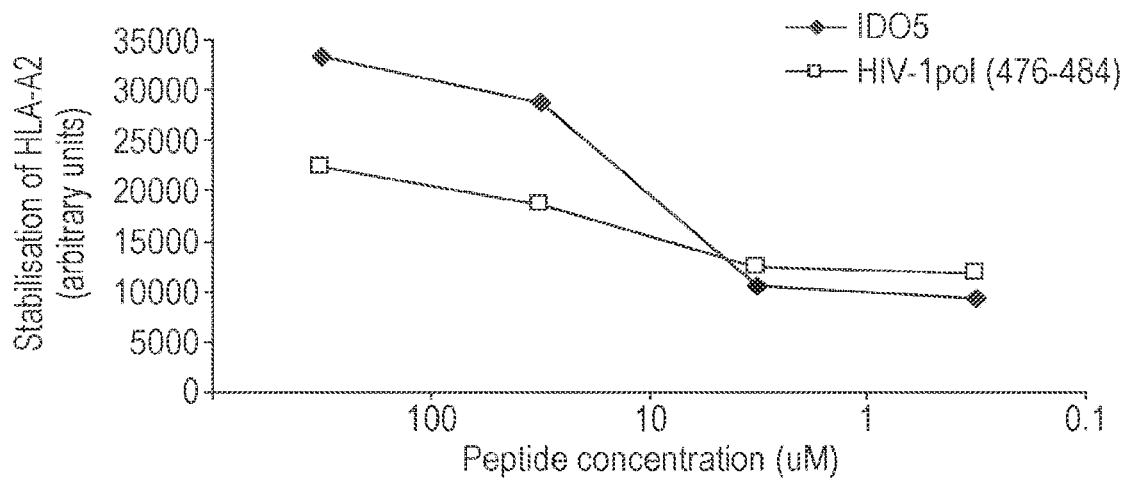
FIG. 2a shows the binding affinity of the peptide IDO5 (SEQ ID NO: 6) to HLA-A2 compared to the HLA-A2-restricted positive control peptide HIV-1 pol$_{476-484}$ (ILKEPVHGV) (SEQ ID NO: 18) by an assembly assay. Notably, IDO5 bound HLA-A2 even better than the high-affinity control epitope. The high binding affinity of IDO5 to HLA-A2 enabled preparation of stable HLA-A2/IDO5 tetramers, which were used to detect IDO-reactive CTL by flow cytometry as shown in FIG. 2b.
Figure 2B:
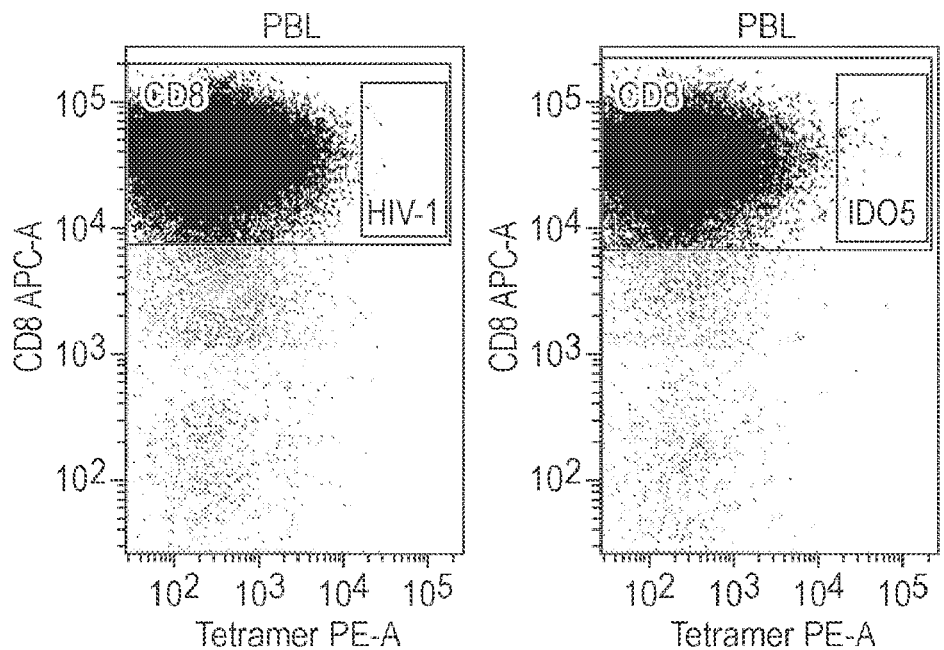
FIG. 2b shows flow cytometry of IDO5-specific CD8 T cells in PBL from a renal cell carcinoma patient after in vitro stimulation, with an HIV tetramer-complex used as control. This analysis clearly confirmed the presence of IDO5-reactive CD8 T cells in the blood of HLA-A2 positive cancer patients.

The apparently most immunogenic IDO-derived peptide, i.e. IDO5, was examined for its binding affinity to HLA-A2 by comparison with a HLA-A2 high affinity positive control epitope, i.e. HIV-1 pol476-484 (ILKEPVHGV (SEQ ID NO: 18), by the assembly assay (FIG. 2a). Notably, IDO5 bound HLA-A2 even better than the high-affinity control epitope. The high binding affinity of IDO5 to HLA-A2 enabled us to make stable HLA-A2/IDO5 tetramers, which were used to detect IDO-reactive CTL by flow cytometry. This analysis clearly confirmed the presence of IDO5-reactive CD8 T cells in the blood of HLA-A2 positive cancer patients (FIG. 2). FIG. 2b illustrates an example of an IDO5 specific T cell response after in vitro stimulation in a renal cell carcinoma patient with an HIV tetramer-complex used as control. While the frequency of IDO-reactive T cells are markedly increased by in vitro stimulation, IDO-reactive T cells were readily detectable ex vivo in selected patients (FIG. 2c): In the three patients with strongest responses after in vitro stimulation, a respective reactivity was also detected ex vivo. Overall, PBL from 7 HLA-A2 positive healthy individuals and 11 HLA-A2 positive patients were analyzed which revealed an average frequency of 0.03% IDO reactive cells of total CD8+ T cells after in vitro stimulation in cancer patients, compared to 0.001% in healthy donors (FIG. 2c).

Figure 2D:
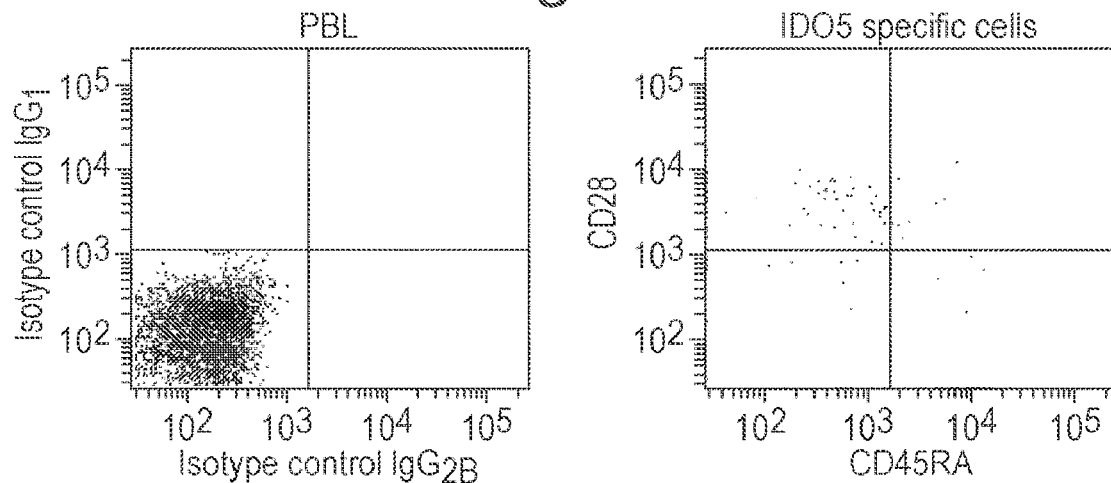
FIG. 2d shows tetramer analysis of IDO5-specific T cells by flow cytometry with ex vivo phenotype staining of IDO5 tetramer gated cells. The ex vivo stainings of IDO-reactive T cells showed that naturally occurring IDO5-specific T cells have a CD45RA-CD28+ central/effector memory phenotype. As a comparison the sample were stained with isotype matched controls.
Figure 2E:
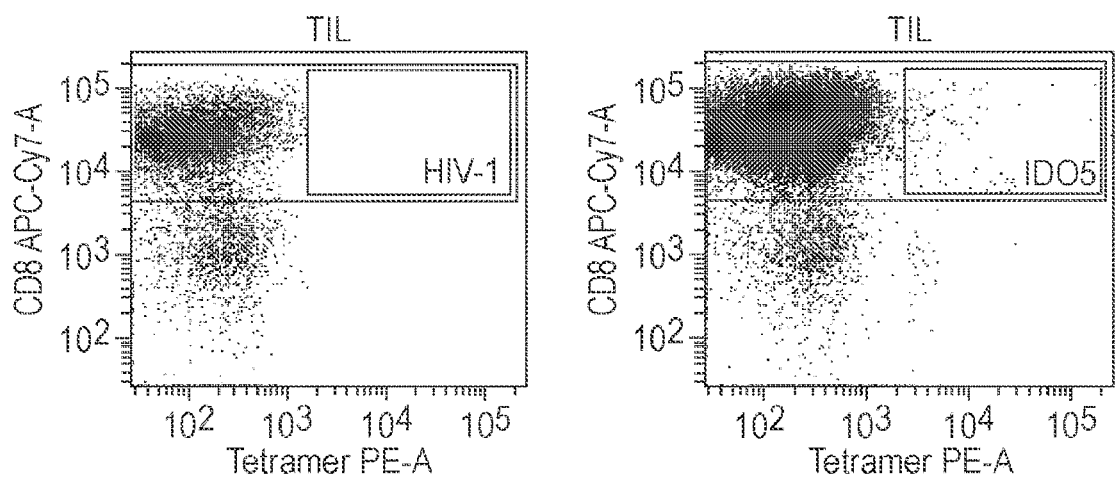
FIG. 2e shows tetramer analysis of IDO5-specific T cells by flow cytometry illustrating the presence of IDO5-specific T cells in IL-2 treated TIL cultures from HLA-A2+ melanoma and head and neck cancer patients by tetramer stainings. IDO5-specific T cells could readily be detected among the TIL. Overall, 4 of the 5 analyzed patients had detectable IDO5-specific T cells.
Figure 2F:
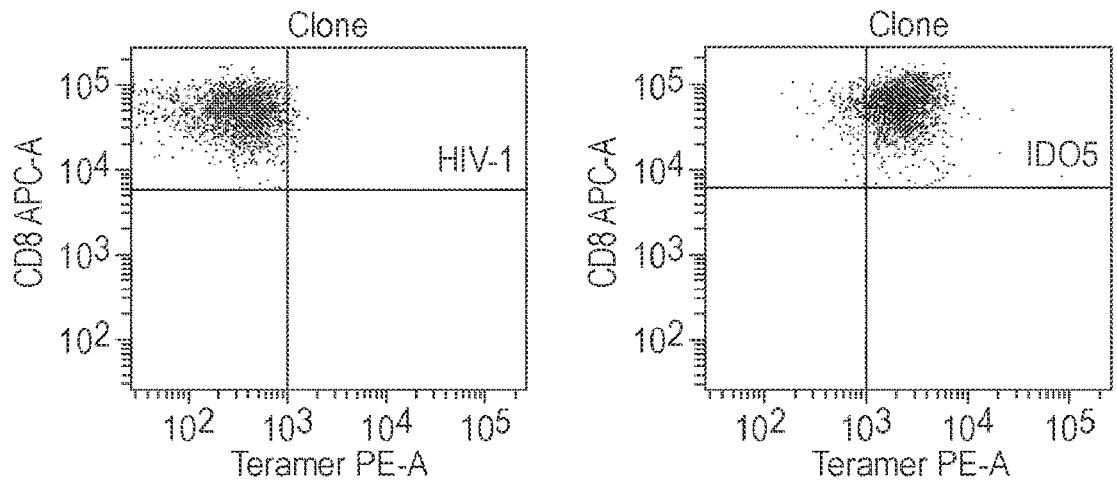
FIG. 2f shows tetramer analysis of IDO5-specific T cells by flow cytometry. To control the specificity of the HLA-A2/IDO5 tetramer we stained an IDO5-specific T-cell clone. The HLA-A2/IDO5 tetramer did efficiently stain the IDO5-specific T-cell clone, whereas the T-cell clone was not stained by the control HLAA2/HIV tetramer.

No IDO-reactive T cells could be detected in any of the healthy donors (FIG. 2b). The ex vivo stainings of IDO-reactive T cells showed that naturally occurring IDO5-specific T cells have a CD45RA-CD28+ central/effector memory phenotype[34]. An example of such an ex vivo phenotype staining of IDO5 tetramer gated cells is shown in FIG. 2d. As a comparison the sample were stained with isotype matched controls. Next, we examined the presence of IDO5- specific T cells in IL-2 treated TIL cultures from HLA-A2+ melanoma and head and neck cancer patients by tetramer stainings. As illustrated in FIG. 2e IDO5-specific T cells could readily be detected among the TIL. Overall, 4 of the 5 analyzed patients had detectable IDO5-specific T cells. Likewise, IDO5-specific T cells in TIL cultures from melanoma and head and neck cancer patients could be detected in ELISPOT (data not shown). To control the specificity of the HLA-A2/IDO5 tetramer we stained an IDO5-specific T-cell clone. The HLA-A2/IDO5 tetramer did efficiently stain the IDO5-specific T-cell clone, whereas the T-cell clone was not stained by the control HLAA2/HIV tetramer (FIG. 2f).

Example 3

(Materials and Methods are as Described in Example 1)

Functional Capacity of IDO Specific T-Cells

Figure 3A:
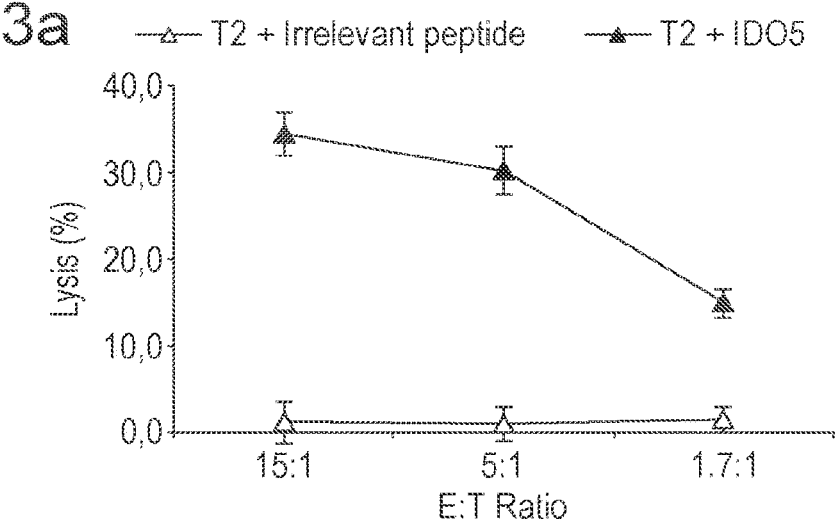
FIG. 3a shows specificity and functional capacity of an IDO5-specific T-cell clone (RBS35) assayed by $^{51}$Cr-release assay to detect lysis of T2-cells with no peptide or pulsed with IDO5 peptide. The T-cell clone RBS35 effectively killed IDO5-pulsed T2-cells whereas T2-cells without peptide were not lysed, as described in example 3.

Having identified patients hosting responses against the IDO5 peptide, we used PBL from such patients to generate CTL bulk cultures against this peptide in vitro. PBL were stimulated by autologous IDO5-pulsed DC. After four rounds of stimulation, the peptide specificity was tested in standard 51Cr release assays. Cells from these bulk cultures lysed TAP-deficient T2-cells pulsed with IDO5 peptides. To analyze the lytic capacity of IDO specific T-cells in more detail, CTL clones were established from these bulk cultures by limiting dilution cloning. After a short expansion period, the specificity of the growing clones was analyzed in standard 51Cr release assays. Of thirty three T-cell clones displaying an IDO specific lytic capacity, four clones were selected for further expansion due to a superior growth rate. A representative T-cell clone is depicted in FIG. 3a: the T-cell clone RBS35 effectively killed IDO5-pulsed T2-cells whereas T2-cells without peptide were not lysed (FIG. 3a).

Example 4

(Materials and Methods are as Described in Example 1)

Killing of Tumor Targets by IDO-Specific T Cells

A number of cancer cell lines and DC were examined for IDO expression by intracellular protein staining followed by FACS analysis[21]. To this end, the colon cancer cell line SW480, the melanoma cell line FM55M, the breast cancer cell lines CAMA-1 and MDA-MB231, directly enriched AML-blasts, and mature DC were IDO positive. Only the colon cancer cell line HCT-116 and immature DC were IDO negative. Furthermore, IFN-γ treatment of the cancer cell lines increased the IDO expression.

Representative examples of IDO stainings are illustrated in histograms in FIG. 4.

Figure 3B:
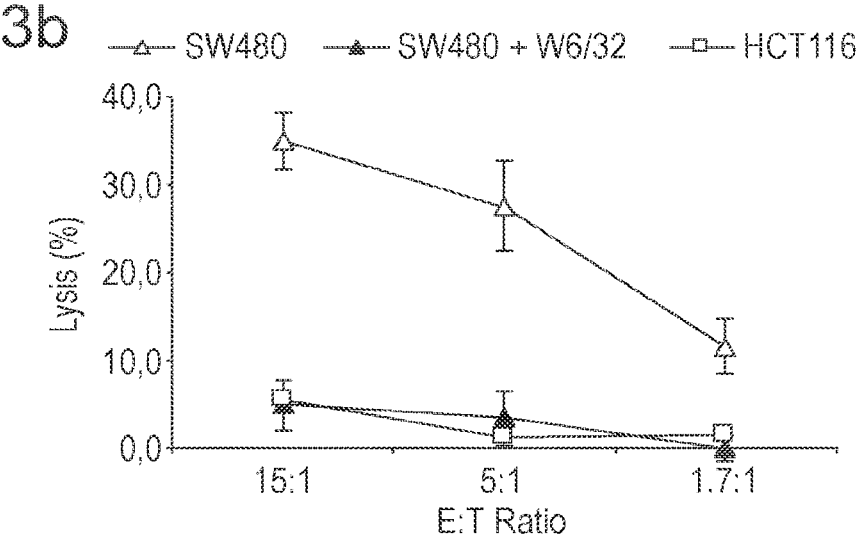
FIG. 3b shows specific lysis by IDO5-specific T-cell clone RBS35 which killed HLA-A2+, IDO+ colon cancer cell line SW480 with high efficacy. In contrast, RBS35 did not lyse the HLA-A2+/IDO– colon cancer cell line HCT-116, as described in example 4. HLA-restriction of RBS35 was confirmed by blocking HLA-class I using the HLA specific mAb W6/32, which completely abolished lysis of the SW480 target cells.
Figure 3C:
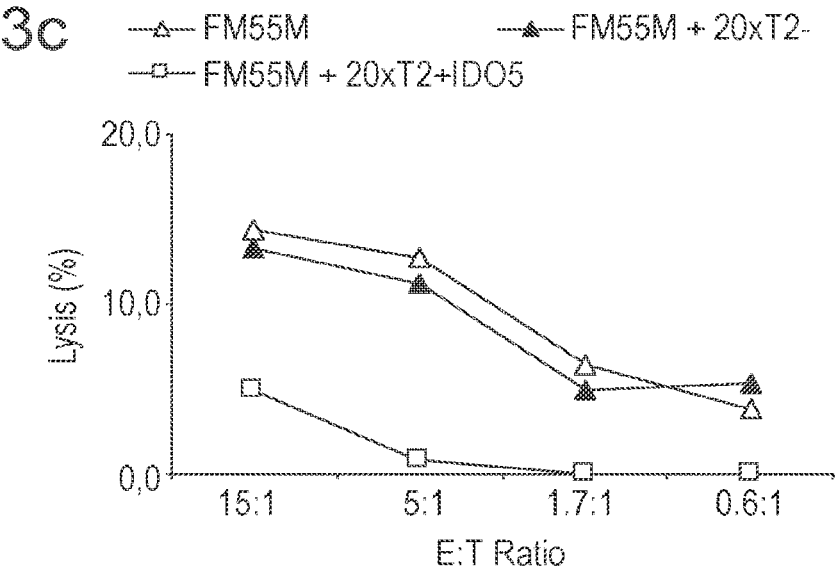
FIG. 3c shows specificity and functional capacity of an IDO5-specific T-cell clone (RBS35) assayed by $^{51}$Cr-release assay. Lysis of the IDO+, HLA-A2+ melanoma cell line FM55M without and with the addition of cold T2-cells pulsed with IDO5 or unpulsed (inhibitor to target ratio=20:1 is shown. The HLA-A2+/IDO+ melanoma cell line FM55M was killed by RBS35. Cold targeted inhibition assays using unlabeled T2-cells pulsed with the IDO5 (10 μM) peptide confirmed the HLA-A2/peptide-specificity of the killing: The addition of cold (unlabeled) IDO5-pulsed T2-cells completely abrogated the killing of FM55M melanoma cells, whereas the addition of cold T2-cells without peptide did not have an effect on the killing of FM55M.

Importantly, the T cell clone RBS35 killed not only peptide pulsed T2-cells but also the HLA-A2+, IDO+ colon cancer cell line SW480 (FIG. 3b) with high efficacy. In contrast, RBS35 did not lyse the HLA-A2+/IDO− colon cancer cell line HCT-116 (FIG. 3b). HLA-restriction of RBS35 was confirmed by blocking HLA-class I using the HLA specific mAb W6/32, which completely abolished lysis of the SW480 target cells (FIG. 3b). Similarly, the HLA-A2+/IDO+melanoma cell line FM55M was killed by RBS35 (FIG. 3c). Cold targeted inhibition assays using unlabeled T2-cells pulsed with the IDO5 (10 μM) peptide confirmed the HLA-A2/peptide-specificity of the killing: The addition of cold (unlabeled) IDO5-pulsed T2-cells completely abrogated the killing of FM55M melanoma cells, whereas the addition of cold T2-cells without peptide did not have an effect on the killing of FM55M (FIG. 3c). Neither did the addition of cold T2-cells pulsed with an irrelevant peptide (HIV-1 pol476-484) did not have an effect on the killing of FM55M (FIG. 7a). No cytotoxicity was observed against the NK-cell target cell line K562 (FIG. 7a).

Figure 3D:
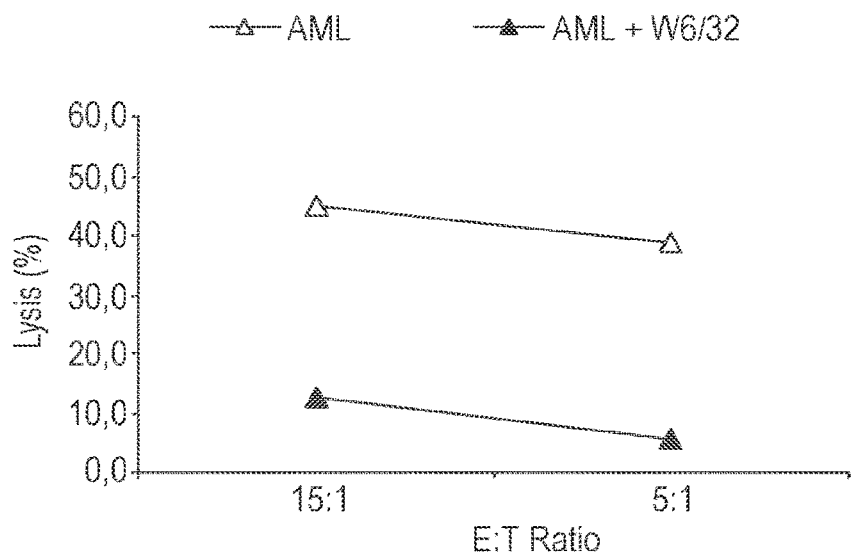
FIG. 3d shows specificity and functional capacity of an IDO5-specific T-cell clone (RBS35) assayed by $^{51}$Cr-release assay. The ability of RBS 35 to lyse human HLA-A2+ AML-blasts enriched directly ex vivo from the bone-marrow of AML patients was tested. T cells (CD3+) and B cells (CD19+) were depleted from the bone marrow of HLA-A2+ AML patients using CD19$^+$ and CD3$^+$ microbeads, respectively. The highly enriched AML-blasts (CD3–, CD19–) were subsequently used as target cells in a $^{51}$Cr release assay with or without the addition of the HLA-class I specific antibody W6/32. RBS35 efficiently lysed the leukemia cells in an HLA-dependent manner.
Figure 3E:
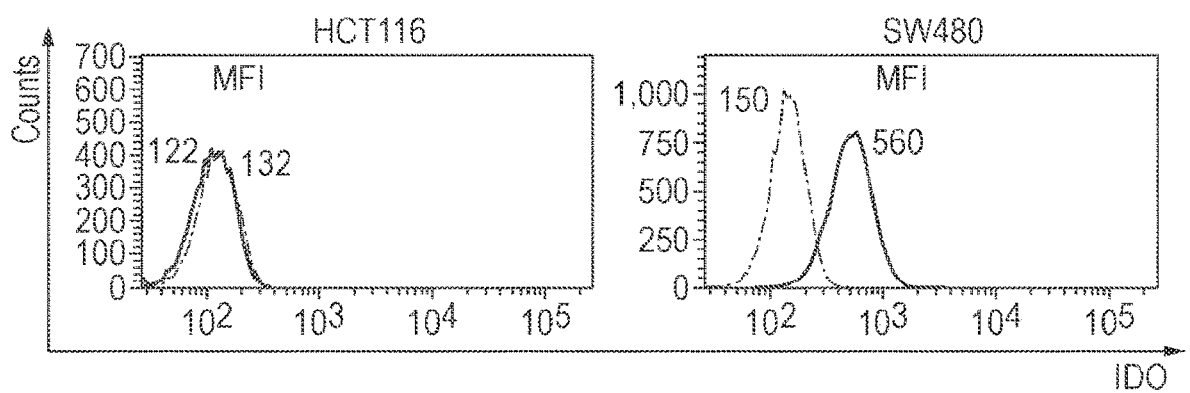
FIG. 3e shows histograms showing intracellular IDO expression in two colon cancer cell lines: HCT116 and SW480. Intracellular IDO expression was given by a one-tailed two sampled T-test comparing MFIIDO (dark histograms) and MFIIsotype control (light histograms), where MFI is the Mean Fluorescence Intensity. Left: HCT-116 (p=0.300). Right: SW480 (p=0.002).

Furthermore, we tested the ability of RBS35 to lyse human HLA-A2+ AML-blasts enriched directly ex vivo from the bone-marrow of AML patients. For this purpose, we depleted T cells (CD3+) and B cells (CD19+) from the bone marrow of HLA-A2+ AML patients; the highly enriched AML-blasts (CD3−, CD19−) were subsequently used as target cells in a $^{51}$Cr release assay. As shown in FIG. 3d; RBS35 efficiently lysed the leukemia cells in an HLA-dependent manner. We enriched AML blasts from six patients (5 HLA-A2+ patients and 1 HLA-A2− patient) and all these expressed IDO (data not shown). RBS35 efficiently lysed the HLA-A2+ leukemia cells in an HLA-dependent manner, while HLA-A2− leukemia cells were not lysed (FIG. 7b).

To illustrate the representative killing of tumor targets by RBS35 the killing of SW480 by a polyclonal, IDO5-specific bulk culture as well as three other T-cell clones (RBS26, RBS31, RBS46) are shown in FIG. 7c and FIG. 7d. Similar to RBS35, none of these clones (RBS26, RBS31, RBS46) lysed the HLA-A2+/IDO− colon cancer cell line HCT-116 (FIG. 7d).

Finally, we examined the killing of the HLA-A2+ breast cancer cell lines CAMA-1 and MDA-MB-231. The CAMA-1 cell line was killed by RBS35 (FIG. 5a), whereas MDA-MB-231 was not recognized by RBS35 (FIG. 5b). INF-γ treatment increased the expression of IDO in both cell lines. In agreement with this, INF-γ treatment increased the killing by RBS35 of CAMA-1 and introduced killing of the MDA-MB-231 cells (FIG. 5).

Additionally, we show that killing by a polyclonal IDOS-specific bulk culture and the RBS35 clone are indeed IDO-specific. Thus, using IDO shRNA we down-regulated IDO protein expression in the human SW480 colon cancer cell line and thereby rescue these tumor cells from being killed (FIG. 5d). This down-regulation was visualized by intracellular protein stainings. These stainings confirmed that the use of IDO ShRNA reduced the level of IDO protein expression in the cells (FIG. 5e). Subsequently, the transfected cells were used as target cells in a 51Cr-release assay. Cancer cells transfected with IDO ShRNA were not recognized by the polyclonal IDO-specific bulk culture, whereas cells transfected with irrelevant control ShRNA were killed as illustrated in FIG. 5d.

Example 5

(Materials and Methods are as Described in Example 1)

Killing of Immune Competent Cells by IDO-Specific T Cells

IDO expression is not restricted to tumor and tumor stroma cells, but can also be induced in immune cells. Thus, as the next and even more important step we addressed the question whether IDO-expressing DC would also be susceptible killing by IDO-reactive CTL. To test this notion, we generated autologous DC from the same donors from whom the CTL clones had been generated; the DC were matured by the addition of a standard maturation cocktail consisting of IL-1β, IL-6, TNF-α, and PGE2[22]. RBS35 effectively killed the matured DC. In contrast, autologous immature IDO– DC were not killed by RBS35 (FIG. 6a). Moreover, we examined the recognition of IDO+ mature DC as well as IDO– immature DC from an HLA-A2+ donor by RBS35. The allogenic matured DC were killed by RBS35 whereas the IDO– immature DC from the same donor (FIG. 6b).

In FIG. 6c it is illustrated that mDC express IDO in contrast to iDC. Next, we tested the ability of RBS35 to lyse autologous monocytes, T cells and B cells. For this purpose, we isolated CD14+ monocytes, CD3+ T cells and CD19+ B cells directly ex vivo from IDO+ PBMC. The isolated cells were subsequently used as target cells in a 51Cr-release assay. Autologous CD14+ monocytes, CD3+ T cells and CD19+ B cells were not lysed by RBS35 (FIG. 6d).

Finally, we sat up an in vitro model to examine if IDO-specific T cells enhance immune responses by depleting IDO-expressing suppressive cells. Hence, cultures of PBMC were treated with IFN-γ to increase the immune activity as well as IDO expression in the cultures with and without autologous IDO specific T cells. Five days later we examined the immune reactivity against the HLA-A2 restricted immunodominant epitope from EBV BMLF1280-288 (GLCTLVAML)(SEQ ID NO: 19) in the cultures. Although the overall cell number was the same in the cultures the reactivity against the EBV peptide was higher in the cultures with IDO-specific T cells (FIG. 6e). Next, we scrutinized if the addition of IDO specific T cells increased the immune reactivity to an extent that allowed detection of EBV responses in an ELISPOT with only 104 PBMC far below the normal detection limit. Indeed, we could detect a clear EBV response even at this low concentration of PBMC (FIG. 6e). As expected we could not detect any EBV response at this low cell concentration in the culture without IDO-specific T cells (FIG. 6e).

REFERENCE LIST

Popov & Schultze; J Mol Med. 2008 February; 86(2):145-60. Epub 2007 Sep. 18

Nicolette C A, Healey D, Tcherepanova I, Whelton P, Monesmith T, Coombs L, Finke L H, Whiteside T, Miesowicz F, (2007). Dendritic cells for active immunotherapy: optimizing design and manufacture in order to develop commercially and clinically viable products. Vaccine, September 27; 25 Suppl 2:B47-60. Epub 2007

Walter E A, Greenberg P D, Gilbert M J, Finch R J, Watanabe K S, Thomas E D, Riddell S R (1995). Reconstitution of cellular immunity against cytomegalovirus in recipients of allogeneic bone marrow by transfer of T-cell clones from the donor. N Engl J Med. 1995 Oct. 19; 333(16):1038-44

Morgan R A, Dudley M E, Wunderlich J R, Hughes M S, Yang J C, Sherry R M, Royal R E, Topalian S L, Kammula U S, Restifo N P, Zheng Z, Nahvi A, de Vries C R, Rogers-Freezer L J, Mavroukakis S A, Rosenberg S A. Cancer regression in patients after transfer of genetically engineered lymphocytes. Science. 2006 Oct. 6; 314 (5796):126-9. Epub 2006 Aug. 31.

Schaft N, Dorrie J, Müller I, Beck V, Baumann S, Schunder T, Kampgen E, Schuler G. A new way to generate cytolytic tumor-specific T cells: electroporation of RNA coding for a T cell receptor into T lymphocytes. Cancer Immunol Immunother. 2006 September; 55(9):1132-41. Epub 2005 Dec. 13

1. Morris E, Hart D, Gao L, et al: Generation of tumor-specific T-cell therapies. Blood Rev 20:61-69, 2006
3. Platten M, Ho P P, Youssef S, et al: Treatment of autoimmune neuroinflammation with a synthetic tryptophan metabolite. Science 310:850-855, 2005
4. Bauer T M, Jiga L P, Chuang J J, et al: Studying the immunosuppressive role of indoleamine 2,3-dioxygenase: tryptophan metabolites suppress rat allogeneic T-cell responses in vitro and in vivo. Transpl Int 18:95-100, 2005
7. Sharma M D, Baban B, Chandler P, et al: Plasmacytoid dendritic cells from mouse tumor-draining lymph nodes directly activate mature Tregs via indoleamine 2,3-dioxygenase. J Clin Invest 117:2570-2582, 2007
8. Munn D H, Sharma M D, Hou D, et al: Expression of indoleamine 2,3-dioxygenase by plasmacytoid dendritic cells in tumor-draining lymph nodes. J Clin Invest 114: 280-290, 2004
9. Thebault P, Condamine T, Heslan M, et al: Role of IFNgamma in allograft tolerance mediated by CD4+ CD25+ regulatory T cells by induction of IDO in endothelial cells. Am J Transplant 7:2472-2482, 2007
10. Baban B, Hansen A M, Chandler P R, et al: A minor population of splenic dendritic cells expressing CD19 mediates IDO-dependent T cell suppression via type I IFN signaling following B7 ligation. Int Immunol 17:909-919, 2005
11. Zou W: Immunosuppressive networks in the tumour environment and their therapeutic relevance. Nat Rev Cancer 5:263-274, 2005
12. Uyttenhove C, Pilotte L, Theate I, et al: Evidence for a tumoral immune resistance mechanism based on tryptophan degradation by indoleamine 2,3-dioxygenase. Nat Med 9:1269-1274, 2003
13. Okamoto A, Nikaido T, Ochiai K, et al: Indoleamine 2,3-dioxygenase serves as a marker of poor prognosis in gene expression profiles of serous ovarian cancer cells. Clin Cancer Res 11:6030-6039, 2005
14. Weinlich G, Murr C, Richardsen L, et al: Decreased serum tryptophan concentration predicts poor prognosis in malignant melanoma patients. Dermatology 214:8-14, 2007
15. Lob S, Konigsrainer A, Schafer R, et al: Levo but not dextro-1-methyl tryptophan abrogates the IDO activity of human dendritic cells. Blood: 2007
16. Andersen M H, Tan L, Sondergaard I, et al: Poor correspondence between predicted and experimental binding of peptides to class I MHC molecules. Tissue Antigens 55:519-531, 2000
17. Andersen M H, Pedersen L O, Becker J C, et al: Identification of a Cytotoxic T Lymphocyte Response to the Apoptose Inhibitor Protein Survivin in Cancer Patients. Cancer Res 61:869-872, 2001
18. Scheibenbogen C, Sun Y, Keilholz U, et al: Identification of known and novel immunogenic T-cell epitopes from tumor antigens recognized by peripheral blood T cells 18. from patients responding to IL-2-based treatment. Int J Cancer 20; 98:409-414, 2002
19. Herr W, Ranieri E, Gambotto A, et al: Identification of naturally processed and HLA-presented Epstein-Barr virus peptides recognized by CD4(+) or CD8(+) T lymphocytes from human blood. Proc Natl Acad Sci USA 96:12033-12038, 1999
20. Keilholz U, Weber J, Finke J H, et al: Immunologic monitoring of cancer vaccine therapy: results of a workshop sponsored by the Society for Biological Therapy. J Immunother 25:97-138, 2002
21. Maecker H T, Frey T, Nomura L E, et al: Selecting fluorochrome conjugates for maximum sensitivity. Cytometry A 62:169-173, 2004
22. Nguyen X D, Eichler H, Sucker A, et al: Collection of autologous monocytes for dendritic cell vaccination therapy in metastatic melanoma patients. Transfusion 42:428-432, 2002
23. Hwang S L, Chung N P, Chan J K, et al: Indoleamine 2,3-dioxygenase (IDO) is essential for dendritic cell activation and chemotactic responsiveness to chemokines. Cell Res 15:167-175, 2005
24. Boasso A, Herbeuval J P, Hardy A W, et al: HIV inhibits CD4+ T-cell proliferation by inducing indoleamine 2,3-dioxygenase in plasmacytoid dendritic cells. Blood 109:3351-3359, 2007
25. Wobser M, Voigt H, Houben R, et al: Dendritic cell based antitumor vaccination: impact of functional indoleamine 2,3-dioxygenase expression. Cancer Immunol Immunother 56:1017-1024, 2007
26. Popov A, Schultze J L: IDO-expressing regulatory dendritic cells in cancer and chronic infection. J Mol Med.: 2007
27. Scheler M, Wenzel J, Tuting T, et al: Indoleamine 2,3-dioxygenase (IDO): the antagonist of type I interferon-driven skin inflammation? Am J Pathol 171:1936-1943, 2007
28. Choi B K, Kim Y H, Kang W J, et al: Mechanisms involved in synergistic anticancer immunity of anti-4-1BB and anti-CD4 therapy. Cancer Res 67:8891-8899, 2007
29. Beck K E, Blansfield J A, Tran K Q, et al: Enterocolitis in patients with cancer after antibody blockade of cytotoxic T-lymphocyte-associated antigen 4. J Clin Oncol %20; 24:2283-2289, 2006
30. Sanderson K, Scotland R, Lee P, et al: Autoimmunity in a phase I trial of a fully human anti-cytotoxic T-lymphocyte antigen-4 monoclonal antibody with multiple melanoma peptides and Montanide ISA 51 for patients with resected stages III and IV melanoma. J Clin Oncol 23:741-750, 2005
31. Maker A V, Phan G Q, Attia P, et al: Tumor regression and autoimmunity in patients treated with cytotoxic T lymphocyte-associated antigen 4 blockade and interleukin 2: a phase I/II study. Ann Surg Oncol 12:1005-1016, 2005
32. Rammensee H G, Falk K, Roetzschke O: MHC molecules as peptide receptors. Curr Biol 5:35-44, 1995
33. Elvin J, Cerundolo V, Elliott T, et al: A quantitative assay of peptide-dependent class I assembly. Eur J Immunol 21:2025-2031, 1991
34. McCutcheon M, Wehner N, Wensky A, et al: A sensitive ELISPOT assay to detect low-frequency human T lymphocytes. J Immunol Methods 210:149-166, 1997
35. Andersen M H, Bonfill J E, Neisig A, et al: Phosphorylated Peptides Can Be Transported by TAP Molecules, Presented by Class I MHC Molecules, and Recognized by Phosphopeptide-Specific CTL. J Immunol 163:3812-3818, 1999
36. Pawelec G, Marsh S G: ESTDAB: a collection of immunologically characterised melanoma cell lines and searchable databank. Cancer Immunol Immunother 55:623-627, 2006
37. Schmidt S M, Schag K, Müller M R, et al: Survivin is a shared tumor-associated antigen expressed in a broad variety of malignancies and recognized by specific cytotoxic T cells. Blood 102:571-576, 2003

SEQUENCE LISTING

```
Sequence total quantity: 20
SEQ ID NO: 1            moltype = AA  length = 403
FEATURE                 Location/Qualifiers
source                  1..403
                        mol_type = protein
                        organism = Homo sapiens
SEQUENCE: 1
MAHAMENSWT ISKEYHIDEE VGFALPNPQE NLPDFYNDWM FIAKHLPDLI ESGQLRERVE 60
KLNMLSIDHL TDHKSQRLAR LVLGCITMAY VWGKGHGDVR KVLPRNIAVP YCQLSKKLEL 120
PPILVYADCV LANWKKKDPN KPLTYENMDV LFSFRDGDCS KGFFLVSLLV EIAAASAIKV 180
IPTVFKAMQM QERDTLLKAL LEIASCLEKA LQVFHQIHDH VNPKAFFSVL RIYLSGWKGN 240
PQLSDGLVYE GFWEDPKEFA GGSAGQSSVF QCFDVLLGIQ QTAGGGHAAQ FLQDMRRYMP 300
PAHRNFLCSL ESNPSVREFV LSKGDAGLRE AYDACVKALV SLRSYHLQIV TKYILIPASQ 360
QPKENKTSED PSKLEAKGTG GTDLMNFLKT VRSTTEKSLL KEG              403

SEQ ID NO: 2            moltype = AA  length = 9
FEATURE                 Location/Qualifiers
source                  1..9
                        mol_type = protein
                        organism = Homo sapiens
SEQUENCE: 2
QLRERVEKL                                                    9

SEQ ID NO: 3            moltype = AA  length = 9
FEATURE                 Location/Qualifiers
source                  1..9
                        mol_type = protein
                        organism = Homo sapiens
SEQUENCE: 3
FLVSLLVEI                                                    9
```

```
SEQ ID NO: 4              moltype = AA   length = 9
FEATURE                   Location/Qualifiers
source                    1..9
                          mol_type = protein
                          organism = Homo sapiens SEQUENCE: 4
TLLKALLEI                                                                  9

SEQ ID NO: 5              moltype = AA   length = 9
FEATURE                   Location/Qualifiers
source                    1..9
                          mol_type = protein
                          organism = Homo sapiens SEQUENCE: 5
FIAKHLPDL                                                                  9

SEQ ID NO: 6              moltype = AA   length = 9
FEATURE                   Location/Qualifiers
source                    1..9
                          mol_type = protein
                          organism = Homo sapiens SEQUENCE: 6
ALLEIASCL                                                                  9

SEQ ID NO: 7              moltype = AA   length = 9
FEATURE                   Location/Qualifiers
source                    1..9
                          mol_type = protein
                          organism = Homo sapiens SEQUENCE: 7
VLSKGDAGL                                                                  9

SEQ ID NO: 8              moltype = AA   length = 9
FEATURE                   Location/Qualifiers
source                    1..9
                          mol_type = protein
                          organism = Homo sapiens SEQUENCE: 8
DLMNFLKTV                                                                  9

SEQ ID NO: 9              moltype = AA   length = 9
FEATURE                   Location/Qualifiers
source                    1..9
                          mol_type = protein
                          organism = Homo sapiens SEQUENCE: 9
VLLGIQQTA                                                                  9

SEQ ID NO: 10             moltype = AA   length = 9
FEATURE                   Location/Qualifiers
source                    1..9
                          mol_type = protein
                          organism = Homo sapiens SEQUENCE: 10
KVLPRNIAV                                                                  9

SEQ ID NO: 11             moltype = AA   length = 10
FEATURE                   Location/Qualifiers
source                    1..10
                          mol_type = protein
                          organism = Homo sapiens SEQUENCE: 11
KLNMLSIDHL                                                                10

SEQ ID NO: 12             moltype = AA   length = 10
FEATURE                   Location/Qualifiers
source                    1..10
                          mol_type = protein
                          organism = Homo sapiens SEQUENCE: 12
SLRSYHLQIV                                                                10

SEQ ID NO: 13             moltype = AA   length = 256
FEATURE                   Location/Qualifiers
source                    1..256
                          mol_type = protein
                          organism = Homo sapiens
SEQUENCE: 13
```

```
MDVLFSFRDG DCSKGFFLVS LLVEIAAASA IKVIPTVFKA MQMQERDTLL KALLEIASCL    60
EKALQVFHQI HDHVNPKAFF SVLRIYLSGW KGNPQLSDGL VYEGFWEDPK EFAGGSAGQS   120
SVFQCFDVLL GIQQTAGGGH AAQFLQDMRR YMPPAHRNFL CSLESNPSVR EFVLSKGDAG   180
LREAYDACVK ALVSLRSYHL QIVTKYILIP ASQQPKENKT SEDPSKLEAK GTGGTDLMNF   240
LKTVRSTTEK SLLKEG                                                  256

SEQ ID NO: 14           moltype = AA  length = 405
FEATURE                 Location/Qualifiers
source                  1..405
                        mol_type = protein
                        organism = Homo sapiens
SEQUENCE: 14
MAHAMENSWT ISKEYHIDEE VGFALPNPQE NLPDFYNDWM FIAKHLPDLI ESGQLRERVE    60
KLNMLSIDHL TDHKSQRLAR LVLGCITMAY VWGKGHGDVR KVLPRNIAVP YCQLSKKLEL   120
PPILVYADCV LANWKKKDPN KPLTYENMDV LFSFRDGDCS KGFFLVSLLV EIAAASAIKV   180
IPTVFKAMQM QERDTLLKAL LEIASCLEKA LQVFHQIHGK YHVNPKAFFS VLRIYLSGWK   240
GNPQLSDGLV YEGFWEDPKE FAGGSAGQSS VFQCFDVLLG IQQTAGGGHA AQFLQDMRRY   300
MPPAHRNFLC SLESNPSVRE FVLSKGDAGL REAYDACVKA LVSLRSYHLQ IVTKYILIPA   360
SQQPKENKTS EDPSKLEAKG TGGTDLMNFL KTVRSTTEKS LLKEG                   405

SEQ ID NO: 15           moltype = AA  length = 258
FEATURE                 Location/Qualifiers
source                  1..258
                        mol_type = protein
                        organism = Homo sapiens
SEQUENCE: 15
MDVLFSFRDG DCSKGFFLVS LLVEIAAASA IKVIPTVFKA MQMQERDTLL KALLEIASCL    60
EKALQVFHQI HGKYHVNPKA FFSVLRIYLS GWKGNPQLSD GLVYEGFWED PKEFAGGSAG   120
QSSVFQCFDV LLGIQQTAGG GHAAQFLQDM RRYMPPAHRN FLCSLESNPS VREFVLSKGD   180
AGLREAYDAC VKALVSLRSY HLQIVTKYIL IPASQQPKEN KTSEDPSKLE AKGTGGTDLM   240
NFLKTVRSTT EKSLLKEG                                                258

SEQ ID NO: 16           moltype = AA  length = 402
FEATURE                 Location/Qualifiers
source                  1..402
                        mol_type = protein
                        organism = Homo sapiens
SEQUENCE: 16
MEPHRPNVKT AVPLSLESYH ISEEYGFLLP DSLKELPDHY RPWMEIANKL PQLIDAHQLQ    60
AHVDKMPLLS CQFLKGHREQ RLAHLVLSFL TMGYVWQEGE AQPAEVLPRN LALPFVEVSR   120
NLGLPPILVH SDLVLTNWTK KDPDGNLETI ISFPGGESLH GFILVTALVE KEAVPGIKAL   180
VQATNAILQP NQEALLQALQ RLRLSIQDIT KTLGQMHDYV DPDIFYAGIR IFLSGWKDNP   240
AMPAGLMYEG VSQEPLKYSG GSAAQSTVLH AFDEFLGIRH SKESGDFLYR MRDYMPPSHK   300
AFIEDIHSAP SLRDYILSSG QDHLLTAYNQ CVQALAELRS YHITMVTKYL ITAAAKAKHG   360
KPNHLPGPPQ ALKDRGTGGT AVMSFLKSVR DKTLESILHP RG                     402

SEQ ID NO: 17           moltype = DNA  length = 1572
FEATURE                 Location/Qualifiers
source                  1..1572
                        mol_type = genomic DNA
                        organism = Homo sapiens
SEQUENCE: 17
aatttctcac tgcccctgtg ataaactgtg gtcactggct gtggcagcaa ctattataag    60
atgctctgaa aactcttcag acactgaggg gcaccagagg agcagactac aagaatggca   120
cacgctatgg aaaactcctg gacaatcagt aaagagtacc atattgatga agaagtgggc   180
tttgctctgc caaatccaca ggaaaatcta cctgatttt ataatgactg gatgttcatt   240
gctaaacatc tgcctgatct catagagtct ggccagcttc gagaaagagt tgagaagtta   300
aacatgctca gcattgatca tctcacagac cacaagtcac agcgccttgc acgtctagtt   360
ctgggatgca tcaccatggc atatgtgtgt ggcaaaggtc atggagatgt ccgtaaggtc   420
ttgccaagaa atattgctgt tccttactgc caactctcca gaaaactgga actgcctcct   480
attttggttt atgcagactg tgtcttggca aactggaaga aaaaggatcc taataagccc   540
ctgacttatg agaacatgga cgttttgttc tcatttcgtg atggagactg cagtaaagga   600
ttcttcctgg tctctctatt ggtggaaata gcagctgctt ctgcaatcaa agtaattcct   660
actgtattca aggcaatgca aatgcaagaa cgggacactt tgctcaaggc gctgttggaa   720
atagcttctt gcttggagaa agcccttcaa gtgtttcacc aaatccacga tcatgtgaac   780
ccaaaagcat ttttcagtgt tcttcgcata tatttgtctg gctggaaagg caaccccag    840
ctatcagacg gtctggtgta tgaagggttc tgggaagacc caaaggagtt gcaggggggc   900
agtgcaggcc aaagcagcgt ctttcagtgc tttgacgtcc tgctgggcat ccagcagact   960
gctggtggag gacatgctgc tcagttcctc caggacatga gaagatatat gccaccagct  1020
cacaggaact tcctgtgctc attagagtca aatccctcag tccgtgagtt tgtcctttca  1080
aaaggtgatg ctggcctgcg ggaagcttat gacgcctgtg tgaaagctct ggtctccctg  1140
aggagctacc atctgcaaat cgtgactaag tacatcctga ttcctgcaag ccagcagcca  1200
aaggagaata agacctctga gacccttca aaactggaag ccaaaggaac tggaggcact  1260
gatttaatga atttcctgaa gactgtaaga gtcagcacca ctgaaaagaa tttgaaggaa  1320
ggttaatgta acccaacaag agcacatttt atcatagcag agacatctgt atgcattcct  1380
gtcattaccc attgtaacag agccacaaac taatactatg caatgtttta ccaataatgc  1440
aatacaaaag acctcaaaat acctgtgcat tccttgtagg aaaacaacaa aaggtaatta  1500
tgtgtaatta tactagaagt tttgtaatct gtatcttatc attggaataa aatgacattc  1560
aataaataaa aa                                                     1572
```

```
SEQ ID NO: 18          moltype = AA  length = 9
FEATURE                Location/Qualifiers
source                 1..9
                       mol_type = protein
                       organism = Homo sapiens
SEQUENCE: 18
ILKEPVHGV                                                                  9

SEQ ID NO: 19          moltype = AA  length = 9
FEATURE                Location/Qualifiers
source                 1..9
                       mol_type = protein
                       organism = Homo sapiens
SEQUENCE: 19
GLCTLVAML                                                                  9

SEQ ID NO: 20          moltype = AA  length = 9
FEATURE                Location/Qualifiers
source                 1..9
                       mol_type = protein
                       organism = Homo sapiens
SEQUENCE: 20
QLRERVEKL                                                                  9
```

The invention claimed is:

1. A method of treating a cancer in a subject in need thereof, the method comprising administering to the subject, a composition comprising:
   (i) a nucleic acid encoding a peptide fragment consisting of no more than 25 consecutive amino acids of indoleamine 2,3-dioxygenase (IDO) of SEQ ID NO: 1, wherein the consecutive amino acids comprise residues 199-207 of SEQ ID NO: 1 (SEQ ID NO: 6: Ala-Leu-Leu-Glu-Ile-Ala-Ser-Cys-Leu), wherein the peptide fragment is immunogenically active and is 13 to 25 amino acids in length.

2. The method of claim 1, wherein the composition further comprises an adjuvant.

3. The method of claim 1, comprising administering a second cancer therapy.

4. The method of claim 3, wherein the second cancer therapy comprises chemotherapy, radiotherapy, treatment with immunostimulating substances, gene therapy, treatment with antibodies, treatment using dendritic cells, or any combination thereof.

5. The method of claim 1, wherein the peptide fragment is 18 to 25 amino acids in length.

6. The method of claim 1, wherein the method results in an eliciting of an immune response against the cancer.

7. The method of claim 1, wherein the cancer is a solid tumor.

8. The method of claim 7, wherein the method elicits the production of INF-γ-producing cells in a peripheral blood lymphocyte (PBL) population of the subject at a frequency of at least 1 cell per $10^4$ PBLs as determined by an ELIPSOT assay.

9. The method of claim 1, wherein the peptide fragment is an MHC Class I-restricted peptide.

10. The method of claim 1, wherein the method elicits the production of INF-γ-producing cells in a peripheral blood lymphocyte (PBL) population of the subject.

11. The method of claim 1, wherein the peptide fragment is an MHC Class II-restricted peptide.

12. The method of claim 1, wherein an IDO-expressing cancer cell and/or an IDO expressing antigen presenting cell are present in the subject, and the method elicits the production of regulatory T-cells having a cytotoxic effect against the IDO-expressing cancer cell and/or the IDO expressing antigen presenting cell.

13. The method of claim 1, wherein the method results in a clinical response, wherein the clinical response is characterized by a stable disease, a partial response or complete remission.

14. The method of claim 1, further comprising administering to the subject a nucleic acid encoding a second immunogenically active protein or an immunogenically active peptide fragment thereof, wherein the second immunogenically active protein is not IDO.

15. The method of claim 1, wherein the nucleic acid is a deoxyribonucleic acid (DNA), a ribonucleic acid (RNA), a locked nucleic acid (LNA), a hexitol nucleic acid (HNA), or a peptide nucleic acid (PNA).

16. The method of claim 1, wherein the cancer is colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangeosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinoma, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder epithelial carcinoma, carcinoma, glioblastoma, neuronoma, craniopharingioma, schwannoma, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemia, lymphoma, acute lymphocytic leukemia, acute myelocytic polycythemia vera, multiple myeloma, Waldenstrom's macroglobulinemia, heavy chain disease, acute nonlymphocytic leukemias, chronic lymphocytic leukemia, chronic myelogenous leukemia, Hodgkin's Disease, non-Hodgkin's lymphoma, rectum cancer, urinary cancer, uterine cancer, oral cancer, skin cancer, stomach cancer, brain tumor, liver cancer, laryngeal cancer, esophageal cancer, mammary tumor, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumor, endometrial cancer, gastric cancer, cancer of the head and neck, chronic lymphoid leukemia, hairy cell leukemia, thyroid cancer, or any combination thereof.

17. The method of claim 1, wherein the cancer is melanoma, breast cancer, ovarian cancer, lung cancer, pancreatic cancer, hematologic cancer, leukemia, colon cancer, renal cell cancer, or any combination thereof.

18. The method of claim 1, wherein the cancer is a benign tumor.

19. The method of claim 1, wherein the cancer is a metastatic cancer.

\* \* \* \* \*

UNITED STATES PATENT AND TRADEMARK OFFICE
CERTIFICATE OF CORRECTION

PATENT NO. : 12,233,103 B2
APPLICATION NO. : 18/298263
DATED : February 25, 2025
INVENTOR(S) : Mads Hald Andersen et al.

It is certified that error appears in the above-identified patent and that said Letters Patent is hereby corrected as shown below:

In the Claims

At Column 60, Claim number 16, Lines 54-55:
"bladder epithelial carcinoma, carcinoma," should read --bladder carcinoma, epithelial carcinoma,--

Signed and Sealed this
Twenty-second Day of April, 2025

Coke Morgan Stewart
*Acting Director of the United States Patent and Trademark Office*